(12) United States Patent
Warren

(10) Patent No.: US 8,895,781 B2
(45) Date of Patent: Nov. 25, 2014

(54) TRANSITION METAL-CATALYZED C—H AMINATION USING UNACTIVATED AMINES

(75) Inventor: Timothy H. Warren, McLean, VA (US)

(73) Assignee: Georgetown University, Washington, DC (US)

(*) Notice: Subject to any disclaimer, the term of this patent is extended or adjusted under 35 U.S.C. 154(b) by 525 days.

(21) Appl. No.: 13/061,021

(22) PCT Filed: Sep. 3, 2009

(86) PCT No.: PCT/US2009/055902
§ 371 (c)(1),
(2), (4) Date: May 16, 2011

(87) PCT Pub. No.: WO2010/028159
PCT Pub. Date: Mar. 11, 2010

(65) Prior Publication Data
US 2011/0213146 A1  Sep. 1, 2011

Related U.S. Application Data

(60) Provisional application No. 61/094,289, filed on Sep. 4, 2008, provisional application No. 61/110,580, filed on Nov. 2, 2008.

(51) Int. Cl.
C07C 213/00 (2006.01)
C07C 215/00 (2006.01)
C07C 221/00 (2006.01)
C07C 223/00 (2006.01)
C07C 225/00 (2006.01)
C07C 211/00 (2006.01)
C07D 263/14 (2006.01)
C07D 263/52 (2006.01)
C07D 521/00 (2006.01)

(52) U.S. Cl.
CPC ............ *C07D 263/52* (2013.01); *C07D 263/14* (2013.01); *C07D 521/00* (2013.01)
USPC .......................................... 564/339; 564/336

(58) Field of Classification Search
None
See application file for complete search history.

(56) References Cited

FOREIGN PATENT DOCUMENTS

WO    WO-2005/007659 A2    1/2005
WO    WO-2008/073781 A2    6/2008

OTHER PUBLICATIONS

Fu et al. Org. Lett. 2007, 9(19), 3813-3816.*
Clark et al. Chem. Commun. 2005, 5175-5177.*
Fu et al. J. Am. Chem. Soc. 2006, 128, 13064.*
Juhl et al. Angew. Chem. Int. Ed. 2001, 40(16) 2995-2997.*
Fraile et al. Org. Lett. 2007, 9(4), 731-733.*
Jacobsen et al. J. Am. Chem. Soc. 1995, 117, 5889-5890.*
Fernandez et al. Catalyst Communications 2 (2001) 165-170.*

(Continued)

Primary Examiner — Clinton Brooks
(74) Attorney, Agent, or Firm — Alan W. Steele; Foley Hoag LLP

(57) ABSTRACT

One aspect of the invention relates to a method of animation or amidation, comprising the step of combining a substrate, comprising a reactive C—H bond, and an amine or amide, comprising a reactive N—H bond, in the presence of an oxidizing agent and a metal-containing catalyst, thereby forming a product with a covalent bond between the carbon of the reactive C—H bond and the nitrogen of the reactive N—H bond.

18 Claims, 26 Drawing Sheets

(56) References Cited

OTHER PUBLICATIONS

Olson, D. E. et al., "Catalytic C—H Amination for the Preparation of Substituted 1,2-Diamines", *J. Am. Chem. Soc.*, 130(34):11248-11249 (American Chemical Society, USA, Aug. 27, 2008).

Yu, X.-Q. et al., "Amidation of Saturated C—H Bonds Catalyzed by Electron-Deficient Ruthenium and Managanese Porphyrins. A Highly Catalytic Nitrogen Atom Transfer Process", *Organic Letters*, 2(15):2233-2236 (American Chemical Society, USA, 2000).

International Search Report and Written Opinion of the International Searching Authority from parent application PCT/US2009/055902 dated Apr. 26, 2010.

* cited by examiner

Figure 1
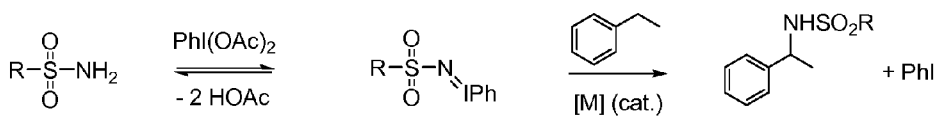
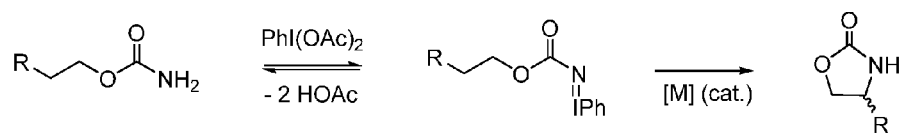
[A]
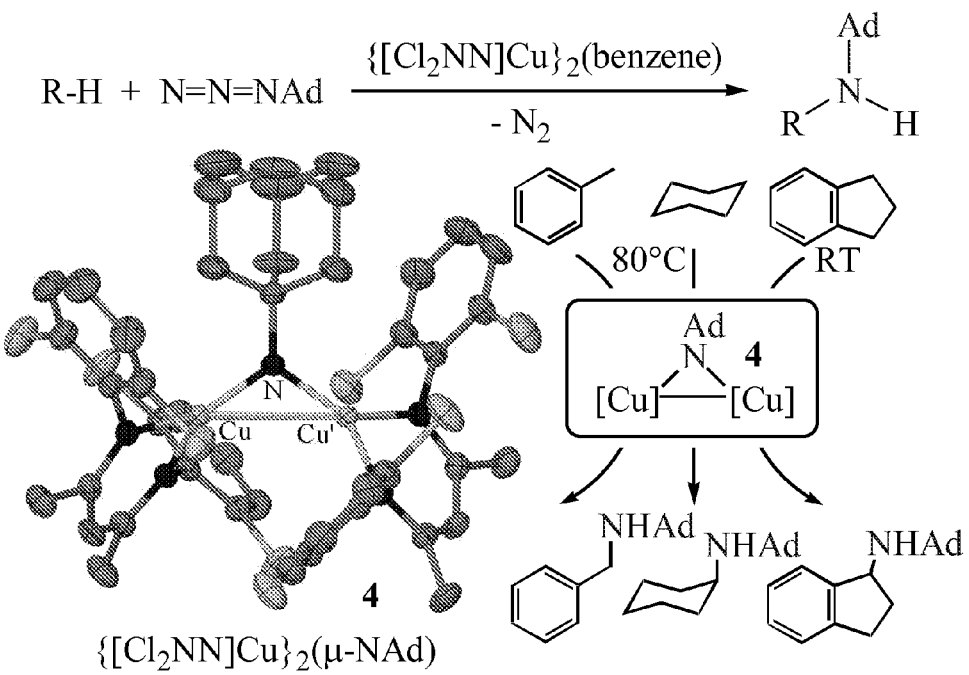
[B]

| Entry | substrate | product | isolated yield (%) | t / hr | 1 eq. substrate yield (%) |
|---|---|---|---|---|---|
| 1 | (toluene) | PhCH₂-NHAd | 92 | 4 | 31 |
| 2 | (ethylbenzene) | PhCH(CH₃)-NHAd | 90 | 5 | 82 |
| 3 | (cumene) | PhC(CH₃)₂-NHAd | 80 | 24 | 50 |
| 4 | (indane) | 1-indanyl-NHAd | 93 | 1 | 80 |
| 5 | (cyclohexane) | cyclohexyl-NHAd | 90 | 48 (1.5)[a] | 32 |
| 6 | PhCHO | PhC(O)NHAd | | 16 | 91 |

(a) microwave radiation at T - 120 C.

Figure 3
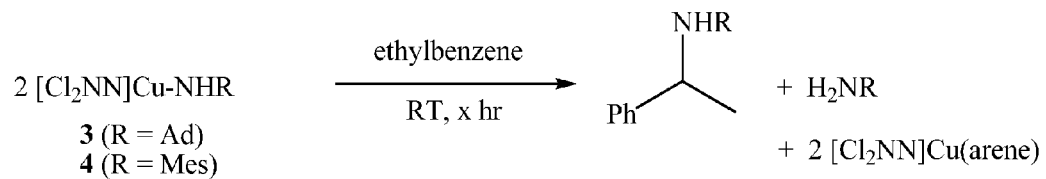
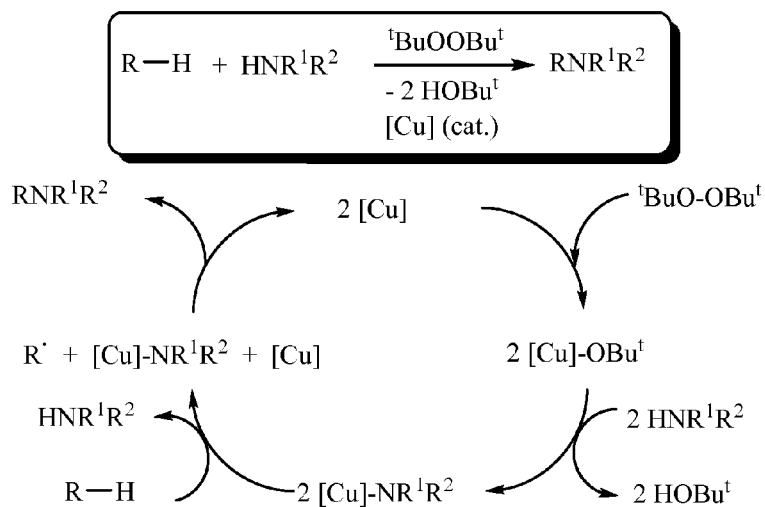
[Cl$_2$NN]Cu-OBu$^t$
(X-ray)
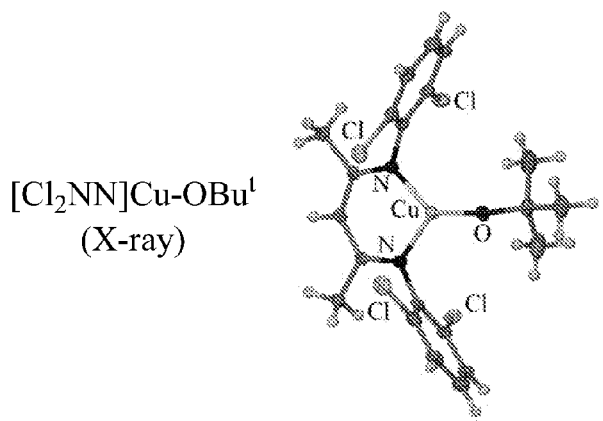

Figure 6
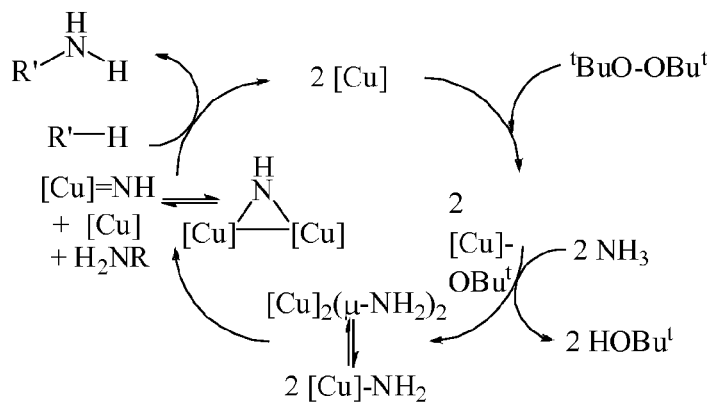
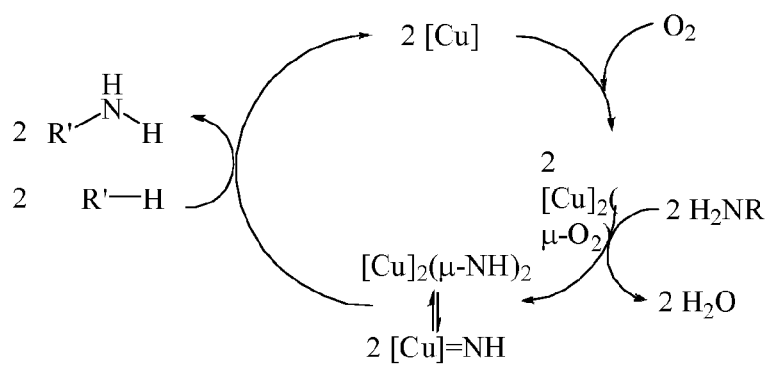
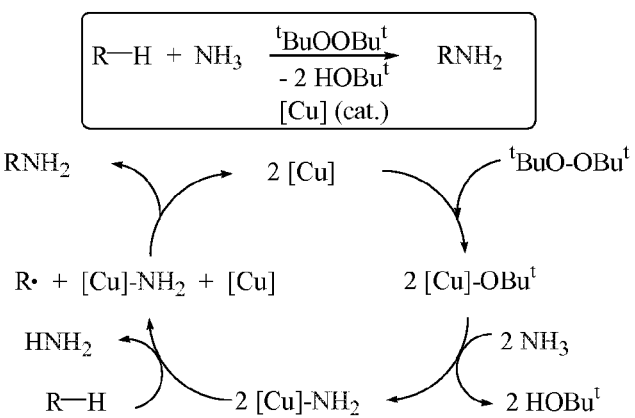

Figure 13
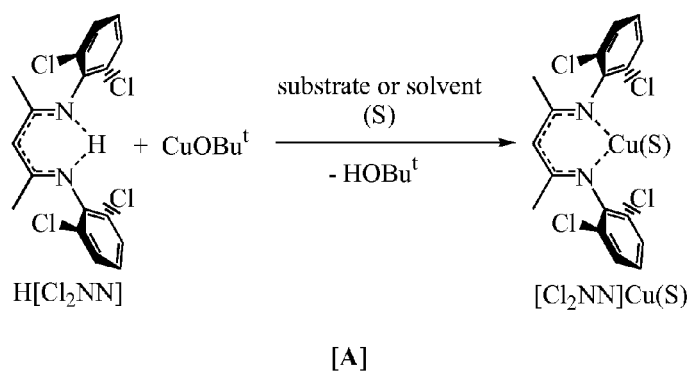
[A]
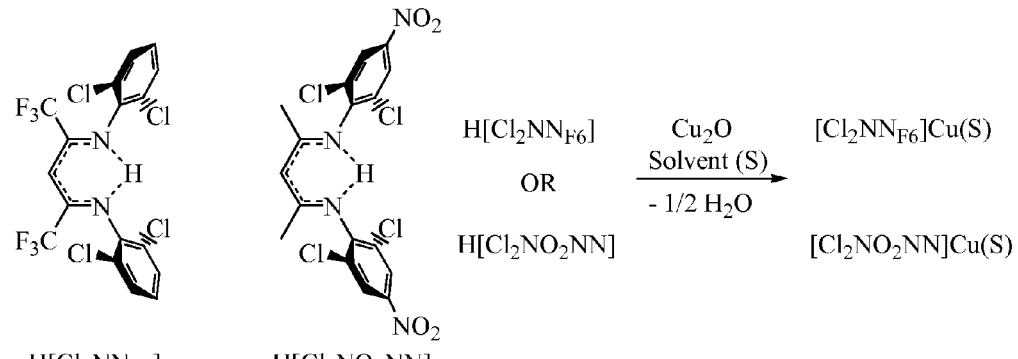
[B]

Figure 14

*H-atom abstraction from ethylbenzene: electronic energies only*

$$[Cu^{II}]\text{-}NR^1R^2 + PhCH_2Me \xrightarrow{\Delta E} [Cu^{I}]\text{-}NHR^1R^2 + Ph\overset{\bullet}{C}HMe$$

| [Cu]-NR$^1$R$^2$ | N$_{amide}$ e$^-$ spin | Cu e$^-$ spin | ΔE for ethylbenzene C-H abstraction (kcal/mol) |
|---|---|---|---|
| [Cl$_2$NN]Cu-NHPh | 0.31 | 0.29 | +23.1 |
| [Cl$_2$NN$_{F6}$]Cu-NHPh | 0.34 | 0.26 | +20.5 |
| [Cl$_2$NN]Cu-NHAd | 0.49 | 0.30 | +11.0 |
| [Cl$_2$NN$_{F6}$]Cu-NHAd | 0.53 | 0.28 | +7.0 |
| [Cl$_2$NN]Cu-Nmorph | 0.48 | 0.28 | +12.1 |
| [Cl$_2$NN$_{F6}$]Cu-Nmorph | 0.52 | 0.26 | +9.5 |
| [Cl$_2$NN]Cu-NH$_2$ | 0.45 | 0.35 | +7.2 |
| [Cl$_2$NN$_{F6}$]Cu-NH$_2$ | 0.48 | 0.33 | +3.5 |
| [Cl$_2$NN]Cu-OBu$^t$ | 0.32 | 0.40 | +19.9 |
| [Cl$_2$NN$_{F6}$]Cu-OBu$^t$ | 0.35 | 0.38 | +15.9 |

*Calculated properties of copper amido intermediates (ADF 2007.1 BP-ZORA/TZ2P(+))*

[Cu]-NMorph = [Cu]—N(morpholine ring)O

Figure 15
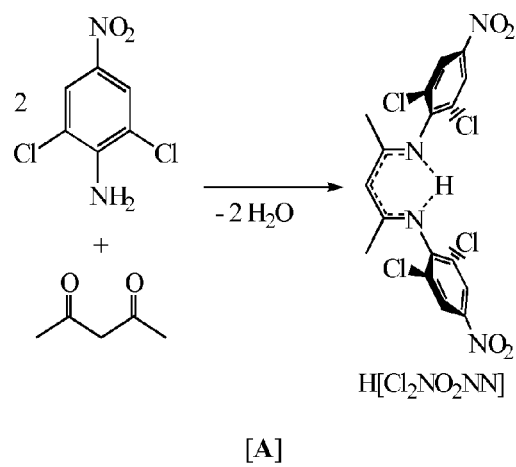
[A]
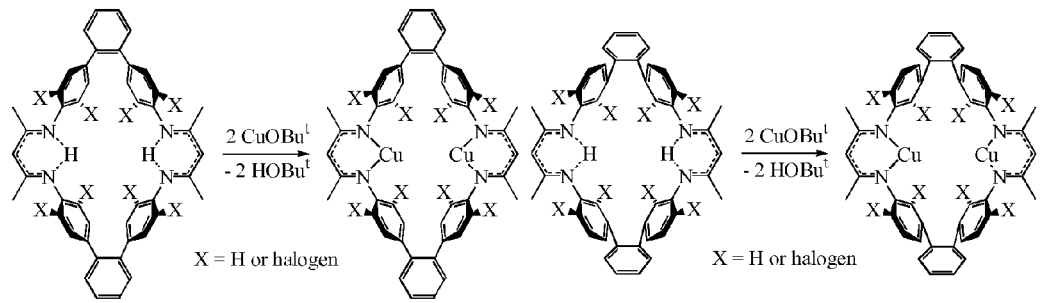
Lee et al. Organometallics 2004, 23, 5328-5385.
(X = H)
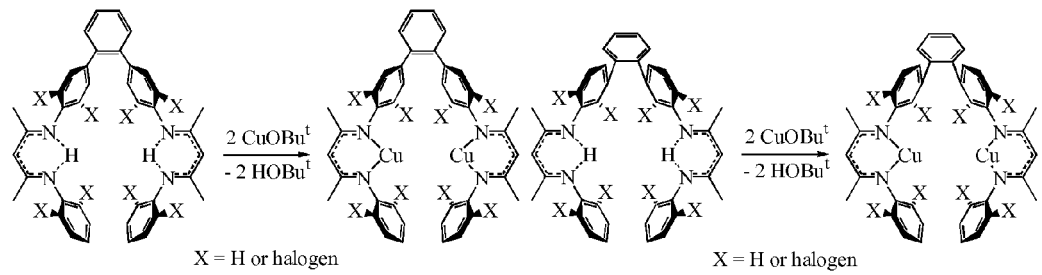
[B]

| Amine | Yield | Amine | Yield |
|---|---|---|---|
| H₂N-Ph (aniline) | 30%, NMR | PhNH-Me (N-methylaniline) | 55%, NMR |
| 2,4,6-trimethylaniline | 20%, NMR | morpholine | 20%, NMR |
| 3,5-bis(trifluoromethyl)aniline | 60%, NMR | | |

| R-H | Amide | Product/ NMR Yield |
|---|---|---|
| PhCH₂CH₃ | PhC(O)NH₂ | Ph-C(O)-NH-CH(CH₃)Ph  61 % |
| PhCH₂CH₃ | pyrrolidinone | N-(1-phenylethyl)pyrrolidinone  87 % |
| PhCH₂CH₃ | tBuC(O)NH₂ | tBu-C(O)-NH-CH(CH₃)Ph  21 % |
| cyclohexane | PhC(O)NH₂ | Ph-C(O)-NH-Cy  48 % |
| cyclohexane | pyrrolidinone | N-Cy-pyrrolidinone  58 % |

Figure 25

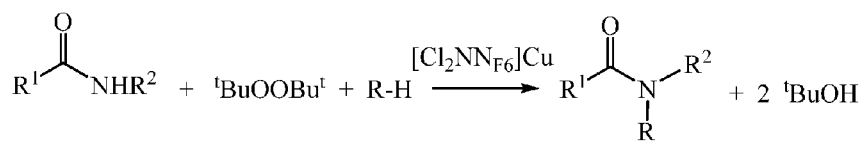

| R-H | Amide | Catalyst Loading | Reaction temp/time | Product/ NMR Yield |
|---|---|---|---|---|
| PhCH2CH3 (ethylbenzene) | benzamide (PhC(O)NH2) | 10 % [Cl2NNF6]Cu | 80°C 16 hrs | PhC(O)NH-CH(CH3)Ph 93 % (GCMS) |
| PhCH2CH3 (ethylbenzene) | 2-pyrrolidinone | 10 % [Cl2NNF6]Cu | 80°C 16 hrs | N-(1-phenylethyl)-2-pyrrolidinone 97 % |
| cyclohexane | benzamide | 10 % [Cl2NNF6]Cu | R.T. 7 hrs | PhC(O)NH-Cy 58 % |
| 3,4-dihydro-2H-pyran | 2-pyrrolidinone | 5 % [Cl2NNF6]Cu | 80°C 16 hrs | N-(3,4-dihydro-2H-pyran-4-yl)-2-pyrrolidinone ~ 20 % |

Figure 26
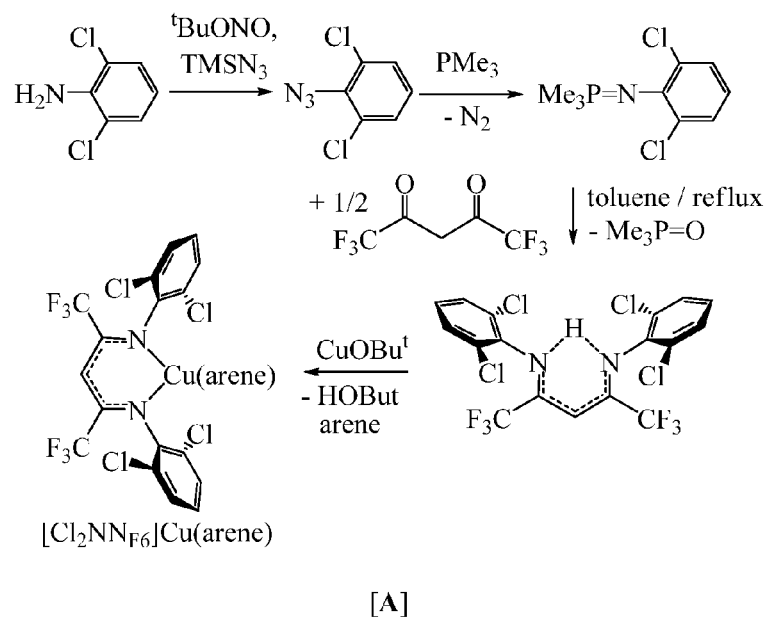
[A]
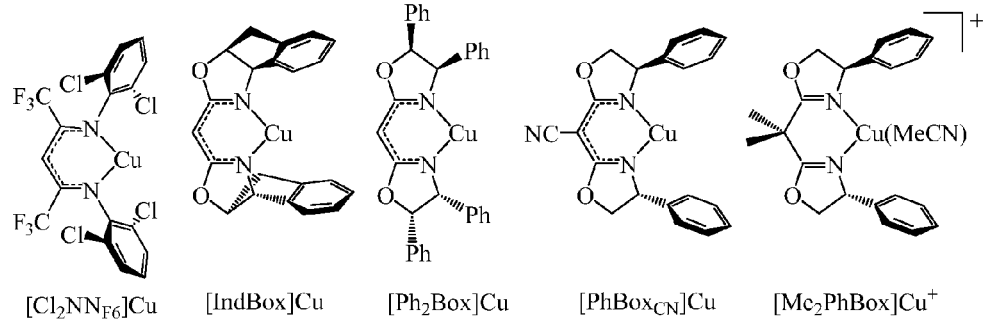
[B]

TRANSITION METAL-CATALYZED C—H AMINATION USING UNACTIVATED AMINES

RELATED APPLICATIONS

This application is the United States national phase of International Application No. PCT/US2009/055902, filed Sep. 3, 2009, and claims the benefit of priority to U.S. Provisional Patent Application Ser. No. 61/094,289, filed Sep. 4, 2008, and U.S. Provisional Patent Application Ser. No. 61/110,580, filed Nov. 2, 2008; the contents of each of which are hereby incorporated by reference.

GOVERNMENT SUPPORT

The invention was made using support provided by the National Science Foundation (Grant CHE-0716304); therefore, the government has certain rights in the invention.

BACKGROUND

Catalytic C—H amination has proven to be a successful strategy to prepare new C—H bonds without the need for a pre-functionalized site. As compared to more traditional means of C—N bond formation involving functional group manipulations (e.g., "hydroxyl to amine"), C—H amination offers the promise to cut out synthetic steps and potentially decrease the amount of by-products formed to affect a new C—N bond. Several catalytic protocols based on Rh, Ru, Ag, Cu, and other metals for amination of benzylic or allylic C—H bonds with iminoiodanes bearing electron-deficient N-substituents represent a useful methodology for the transformation of C—H to C—N bonds. C. Liang, F. Collet, F. Robert-Peillard, P. Muller, R. H. Dodd, P. Dauban, *J. Am. Chem. Soc.* 2008, 130, 343; K. W. Fiori, J. Du Bois, *J. Am. Chem. Soc.* 2007, 129, 562; R. P. Reddy, H. M. L. Davies, *Org. Lett.* 2006, 8, 5013; J.-L. Liang, S.-X. Yuan, J.-S. Huang, W.-Y. Yu, C.-M. Che, *Angew. Chem. Int. Ed.* 2002, 41, 3465; X.-Q. Yu, J.-S. Huang, X.-G. Zhou, C.-M. Che, *Org. Lett.* 2000, 2, 2233; Z. Li, D. A. Capretto, Rahaman, C. He, *Angew. Chem. Int. Ed.* 2007, 46, 5184; Y. Cui, C. He, *Angew. Chem. Int. Ed.* 2004, 43, 4210; M. R. Fructos, S. Trofimenko, M. M. Días-Requejo, P. J. Pérez, *J. Am. Chem. Soc.* 2006, 128, 11784; M. M. Díaz-Requejo, T. R. Belderraín, M. C. Nicasio, S. Trofimenko, P. J. Pérez, *J. Am. Chem. Soc.* 2003, 125, 12078; H. M. L. Davies, J. R. Manning, *Nature* 2008, 451, 417; P. Dauban, R. H. Dodd, in *Amino Group Chemistry* (Ed.: A. Ricci), Wiley-VCH, Weinheim, 2008, pp. 55; and P. Müller, C. Fruit, *Chem. Rev.* 2003, 103, 2905. Studies by Du Bois and other have shown its compatibility in the synthesis of more elaborate product. Importantly, retention of stereochemistry is commonly observed in these transformations.

A disadvantage of this promising methodology is that highly functionalized, electron-deficient nitrene precursors such as sulfonylamines must be used in conjunction with expensive and environmentally unfriendly oxidants, such as PhI(OAc)$_2$. See FIG. 1A. The resulting amines must be deprotected to give the more synthetically useful primary amines. Moreover, expensive rhodium based catalysts Rh$_2$L$_4$ are typically used in 2-5 mol % in the most successful systems.

In addition to iminoiodane nitrene precursors PhI═NSO$_2$R (M. R. Fructos, S. Trofimenko, M. M. Días-Requejo, P. J. Pérez, *J. Am. Chem. Soc.* 2006, 128, 11784; M. M. Díaz-Requejo, T. R. Belderraín, M. C. Nicasio, S. Trofimenko, P. J. Pérez, *J. Am. Chem. Soc.* 2003, 125, 12078), some copper systems allow for the amination of benzylic and allylic C—H bonds employing activated secondary amines such as MeNHSO$_2$Ph and t-butylperacetate. Use of 5 mol % copper(II) triflate and 1,10-phenanthroline as catalyst results in good yields for benzyling and allylic amination of a number of substrates (G. Pelletier D. A. Powell, *Org. Lett* 2006, 8, 6031.) The use of secondary amines suggests that some mechanism that does not involve metal-nitrene intermediates [Cu]═NR is likely operative, as shown below.

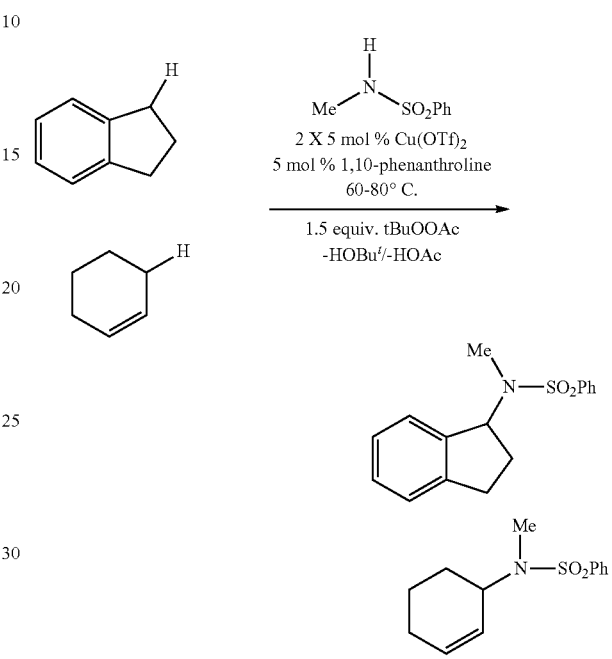

Nonetheless, a strong electron-withdrawing group such as sulfonyl on the secondary amine is required to enable this C—H amination reaction. This sulfonyl group would generally be deprotected in a in further synthetic elaboration of the C—H amination product, detracting from the atom economy of this transformation.

Recently, a new copper-based catalyst system for C—H amination with organoazides was disclosed. See FIG. 1B. Copper is a particularly attractive metal for catalysis, approximately 10,000-25,000 times less expensive than rhodium. Using an inexpensive, easy-to-prepare β-diketiminate supporting ligand, dicopper nitrenes [Cu]$_2$(μ-NR) have been identified as meta-stable isolable intermediates in C—H amination reactions. T. H. Warren (Georgetown University), PCT Int. Appl. WO 2008073781, 2008; and Y. M. Badiei, A. Krishnaswamy, M. M. Melzer, T. H. Warren, *J. Am. Chem. Soc.* 2006, 128, 15056. These species, initially prepared by organoazides, can be isolated, crystallized, spectroscopically characterized. Presumably via a dissociation reaction to give a terminal nitrene [Cu]═NR and [Cu], they participate in C—H amination reactions. Dissolution of {[Cl$_2$NN]Cu}$_2$(μ-NAd) in toluene, indane, or cyclohexane at room temperature or with heating to 80° C. resulted in adamantylnitrene transfer to give the corresponding amination products.

Importantly, this valuable C—H functionalization reaction is amendable to catalytic protocols. Heating a number of neat substrates with N$_3$Ad in the presence of 2.5 mol % {[Cl$_2$NN]Cu}$_2$(benzene) gives rise to high amination yields. See FIG. 2. The use of only one equivalent of substrate in benzene solvent also leads to 80+% yields for secondary benzylic substrates such as ethylbenzene and indane as well as amidation of benzaldehyde in 91% yield. The rate of C—H amination is strongly correlated with strength of the reacting C—H bond, allowing means for selectivity.

The amination of aldehydes has also been reported. However, these reactions are limited to the use of primary organic amines (H₂NR), their hydrochloride salts (see W.-J. Yoo, C.-J. Li *J. Am. Chem. Soc.* 2006, 128, 13064, as discussed below), or primary sulfonylamines (H₂NSO₂R; see J. Chan, K. D. Baucom, J. A. Murry *J. Am. Chem. Soc.* 2007, 129, 14106-14107). For example, in the report by Yoo and Li (W.-J. Yoo, C.-J. Li *J. Am. Chem. Soc.* 2006, 128, 13064), simple copper salts are used in conjunction with AgIO₃ as co-catalyst along with t-butyl hydroperoxide or T-HYDRO (69-70% tBuOOH in water) as oxidant, as shown below with a proposed mechanism:

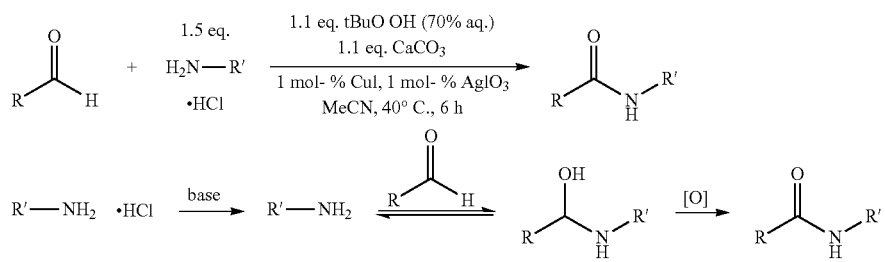

In addition, Fu has reported the use of copper catalysts for the amidation of C—H bonds. N-bromosuccinimide (NBS) and N-chlorosuccinimide (NCS) were used as oxidants coupled with primary amides such as benzamide (H₂NC(O)Ph) and tosylamine (H₂NSO₂(p-MeC₆H₄)) (see Liu, X.; Zhang, Y.; Wang, L.; Fu, H.; Jiang, Y.; Zhao, Y. *J. Org. Chem.* 2008, 73, 6207-6212; Wang, Z.; Zhang, Y.; Fu, H.; Jiang, Y.; Zhao, Y. *Org. Lett.* 2008, 10, 1863-1866; and Zhang, Y.; Fu, H.; Jiang, Y.; Zhao, Y. *Org. Lett.* 2007, 9, 3813-3816). For instance, a benzylic C—H bond in ethylbenzene is amidated with these two reagents using NBS and CuBr (20 mol %) in 50 and 65% yield. FeCl₂ at 10 mol % catalyst loadings also serves as an inexpensive catalyst for similar reactions with NBS.

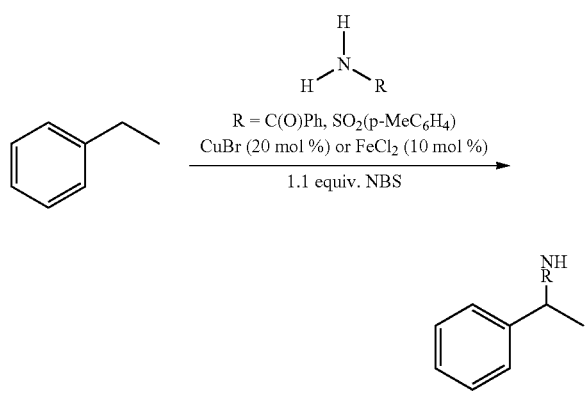

Both primary and secondary amides could be employed in the amidation of N,N-dimethylaniline derivates using NCS and ᵗBuOOH as oxidants under CuBr catalysis (20 mol % and 5 mol %, respectively).

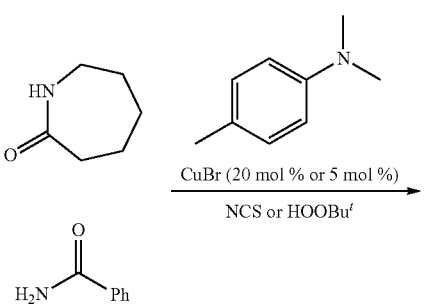

-continued

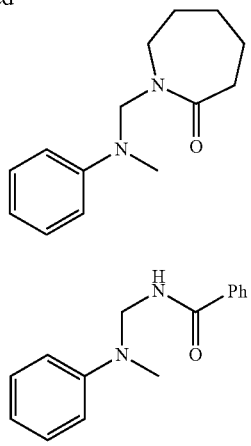

However, there remains a need for amination methods which avoid the need for more highly functionalized precursors, such as alcohols, aldehydes, ketones as well as organoazides. In addition, there remains a need for a method of amination of aldehydes which is not limited to primary amines, and their hydrochoride salts, and primary sulfonamides. Further, an amination method for unactivated substrates, and one which uses an easy-to-remove oxidant, is also desirable.

SUMMARY

One aspect of the invention relates to a method of amination or amidation, comprising the step of reacting a substrate, comprising a reactive C—H bond, with an amine or amide, comprising a reactive N—H bond, in the presence of an oxidizing agent and a metal-containing catalyst, thereby forming a product with a covalent bond between the carbon of the reactive C—H bond and the nitrogen of the reactive N—H bond.

BRIEF DESCRIPTION OF THE FIGURES

FIG. 1 depicts [A] known C—H amination via electron-deficient iminoidanes; and [B] a known copper-catalyzed C—H amination via organoazides.

FIG. 3 depicts a scheme showing stoichiometric C—H amination with organic amines, and a proposed catalytic mechanism thereof.

FIG. 6 depicts proposed mechanisms for amination using ammonia as the amine and peroxide or oxygen as the oxidant.

FIG. 13 depicts [A] in situ formation of a amination catalyst; and [B] a reaction scheme showing use of a in situ formed catalyst.

FIG. 14 depicts the results of DFT calculations which demonstrate that the incorporation of electron-withdrawing groups into certain ligands generate metal-amide intermediates which are more potent towards C—H bond abstraction than a comparable catalyst structure without such substitution.

FIG. 15 depicts [A] a route to [Cl$_2$NO$_2$NN]; and [B] selected linked complexes which may be useful for intramolecular cyclization reactions.

FIG. 25 depicts selected results of amidations with [Cl$_2$NN$_{F6}$]Cu as the catalyst.

FIG. 26 depicts [A] a scheme showing a synthetic route to β-diketiminates and β-diketiminato copper(I) complexes; and [B] selected bis(oxazolines) copper catalysts.

DETAILED DESCRIPTION

Figure 2:
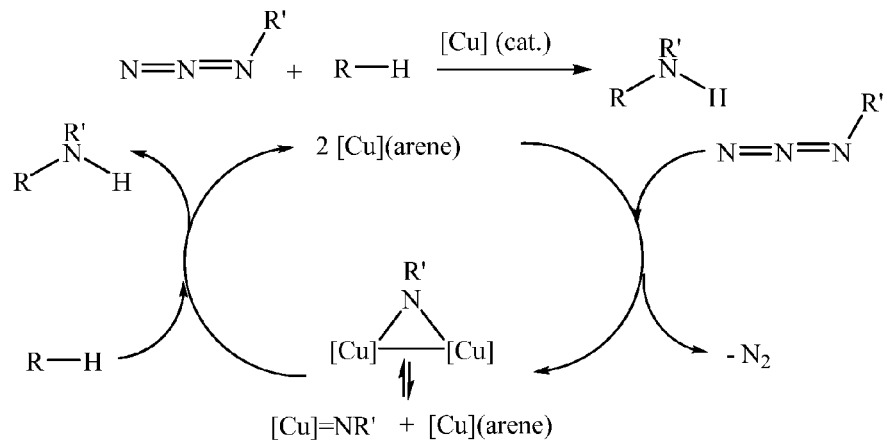
FIG. 2 depicts a proposed mechanism for copper-catalyzed C—H amination via organoazides, and a table of results for several such reactions.

One aspect of the invention relates to metal-catalyzed C—H amination reactions. In certain embodiments, the C—H amination reactions utilize primary or secondary amines, oxidants (such as peroxides), and metal-containing catalysts (such as copper). Remarkably, the amination methodology described herein avoids the need to use highly functionalized precursors and/or organoazides. In addition, the disclosed transformations are environmentally attractive since they avoid traditional functional group transformations in the formation of C—N bonds and they generate only an alcohol (or water, if hydrogen peroxide is used as the oxidant) as the sole stoichiometric by-product.

I. OVERVIEW

It was recently demonstrated that {[Me$_2$NN]Cu}$_2$(μ-benzene) reacts with $^t$BuOOBu$^t$ to give the copper(II)-alkoxide [Me$_2$NN]Cu—OBu$^t$, which then reacts with a secondary amine (HNRR') to give the crystallographically characterized aminated product (such as [Me$_2$NN]Cu—NRR'). Given the ability of [Cu]—OBu$^t$ intermediates to form new [Cu]—NRR' species through this formal acid-base reaction, reactions with primary amines were attempted. Remarkably, [Cu]—NHMes complexes are formed upon the addition of H$_2$NMes to [Cu]—OBu$^t$. The species generated are the same as those generated by a more traditional synthesis of [Cu]—NHMes via the reaction of [Cu]—Cl with LiNHMes. Moreover, the resulting primary amides decompose in ethylbenzene to give amination products, as shown in FIG. 3 (top).

A proposed catalytic mechanism for amination is provided in FIG. 3 (bottom). Importantly, this catalytic cycle does not involve nitrene intermediates, but rather an abstraction of a substrate hydrogen by a [Cu]—NR$^1$R$^2$ intermediate to give an organic radical (R.) which can then combine with a [Cu]—NR$^1$R$^2$ intermediate to yield an amine.

Combination of the stoichiometric observations discussed above into one reaction vessel resulted in a new catalytic protocol for C—H amination with amines and peroxides. For example, heating one equivalent of H$_2$NMes in ethylbenzene at 80° C. for 16 h with {[Cl$_2$NN]Cu}$_2$(benzene) resulted in about 75% conversion of H$_2$NMes to a mixture of the insertion product PhCH(NHMes)Me (58% yield) and MesN=NMes (17% yield). In addition, use of the electron-poor H$_2$NAr$^F$ (Ar$^F$=(CF$_3$)$_2$C$_6$H$_3$) under similar conditions resulted in clean formation of the new secondary amine PhCH(NHAr$^F$)Me in 92% yield without the corresponding diazene Ar$^F$N=NAr$^F$ by-product. Remarkably, these are the first examples employing "normal" primary amines possessing N-aryl or N-alkyl substituents with simple oxidants in C—H amination into sp$^3$-hybridized C—H bonds.

Secondary amines can also be used in the C—H amination reaction. For instance, amination of ethylbenzene with HNMePh takes place with 2.5 mol % {[Cl₂NN]Cu}₂(μ-benzene) and one equivalent of ᵗBuOOBuᵗ. In addition, the amination of ethylbenzene with a cyclic secondary amine, morpholine, takes place with 2.5 mol % of {[Cl₂NN]Cu}₂(μ-benzene) and one equivalent of ᵗBuOOBuᵗ. Moreover, diazene byproducts (RN═NR), one of the shortcomings of known methodologies, are not be expected to be problematic when secondary amines are used since their formation would require the cleavage of kinetically robust N—C bonds. Additional reaction details, and further examples for amination with primary or secondary amines, are provided in the Exemplification below.

Figure 4:
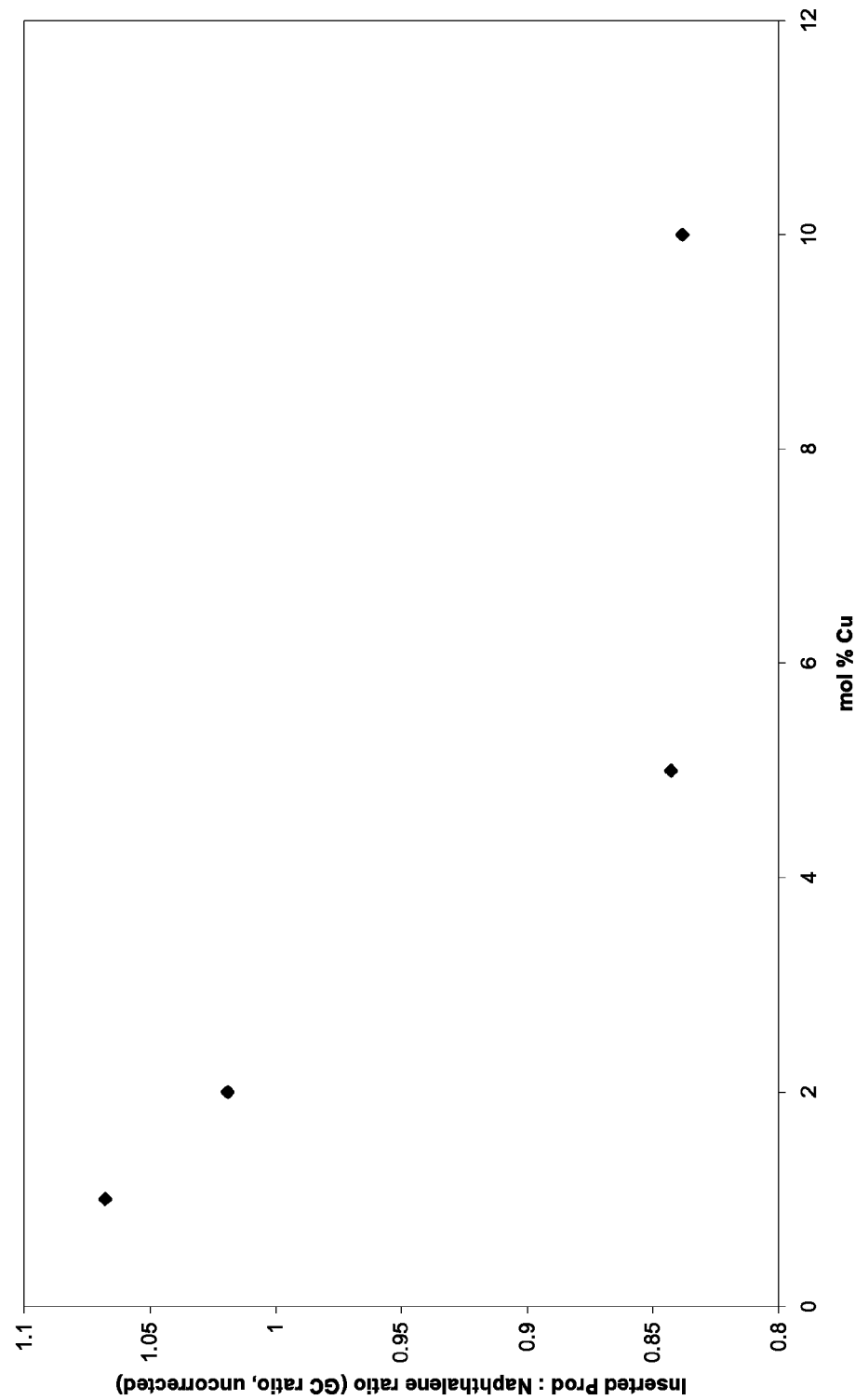
FIG. 4 depicts a graph showing the effects of catalyst loading on the ratio of desired secondary amine PhCH(NHMes)Me compared to the undesirable diazene MesN=NMes.
Figure 5:
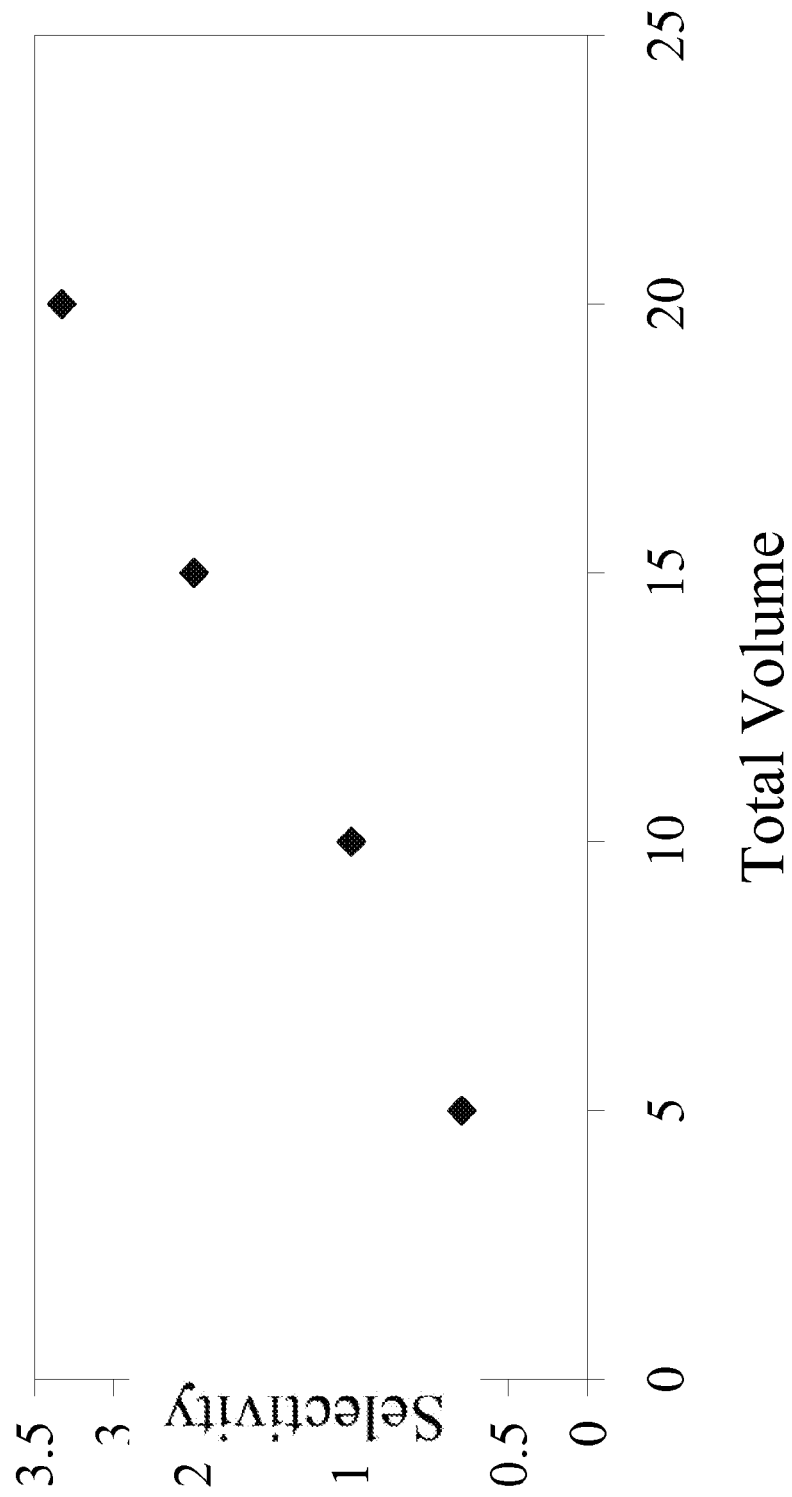
FIG. 5 depicts a graph showing "Selectivity"; "Selectivity" is the uncorrected PhCH(NHMes)Me/MesN=NMes GC signal.

In certain embodiments, lower catalyst loadings give a better ratio of desired secondary amine PhCH(NHMes)Me compared to the undesirable diazene MesN═NMes (FIG. 4). In certain embodiments, the primary byproduct in these reactions with anilines (ArNH₂) is the diazene (ArN═Nar). In optimization reactions employing MesNH₂ in ethylbenzene, it was found that the diazene byproduct (MesN═NMes) can be minimized with (1) low catalyst loadings, (2) dilute conditions, and (3) higher temperatures (FIG. 5).

In some cases, direct conversion to an imine is possible. For example, as shown below, use of about one equivalent 2,6-F₂C₆H₃NH₂ with about one equivalent ᵗBuOOBuᵗ gave the imine PhC(═N(2,6-F₂C₆H₃))Me as the primary product in about 40% yield (GC estimation) with only a small amount of the secondary amine PhC(NH(2,6-F₂C₆H₃))Me detectable. This is consistent with rapid oxidation of the secondary amine under some conditions.

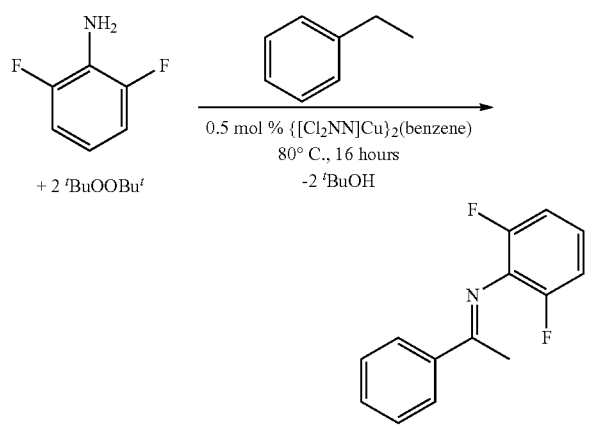

In addition, primary aliphatic amines such as H₂NCH₂CH₂Ph can also be used to give amination product, as shown below. Unoptimized yields indicate that this is a more sluggish reaction than with anilines, resulting in lower conversions (about 20%) at comparable times.

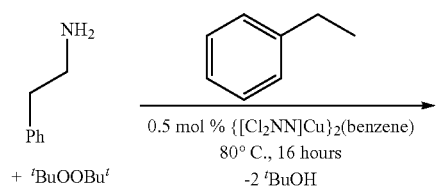

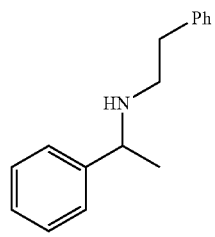

Further, under related conditions, certain amines such as PhCH(Me)NH₂ are even more sluggish, and result new secondary amines along with oxidized imine products.

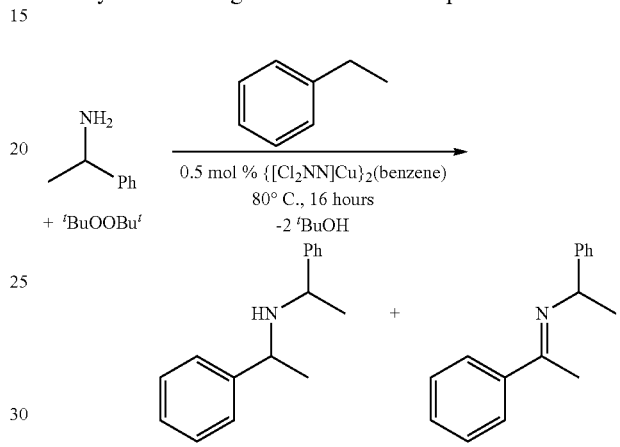

Also attractive is the use of ammonia, NH₃, which would enable the direct conversion of a hydrocarbon into a primary amine RNH₂, as shown below:

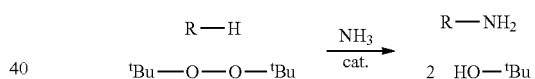

In yet another embodiment of the invention, when the amination substrate is an aldehyde, one may envision preparing amides, as depicted in the scheme below:

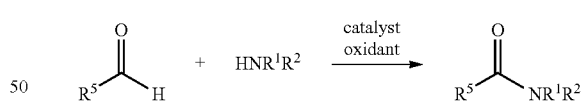

Organic peroxides ROOR should be appropriate oxidants by a related catalytic cycle; oxygen could also be used as an oxidant. Proposed catalytic cycles for the reaction with peroxide and with oxygen are shown in FIG. 6.

II. AMINES AND AMIDES

Figure 7:
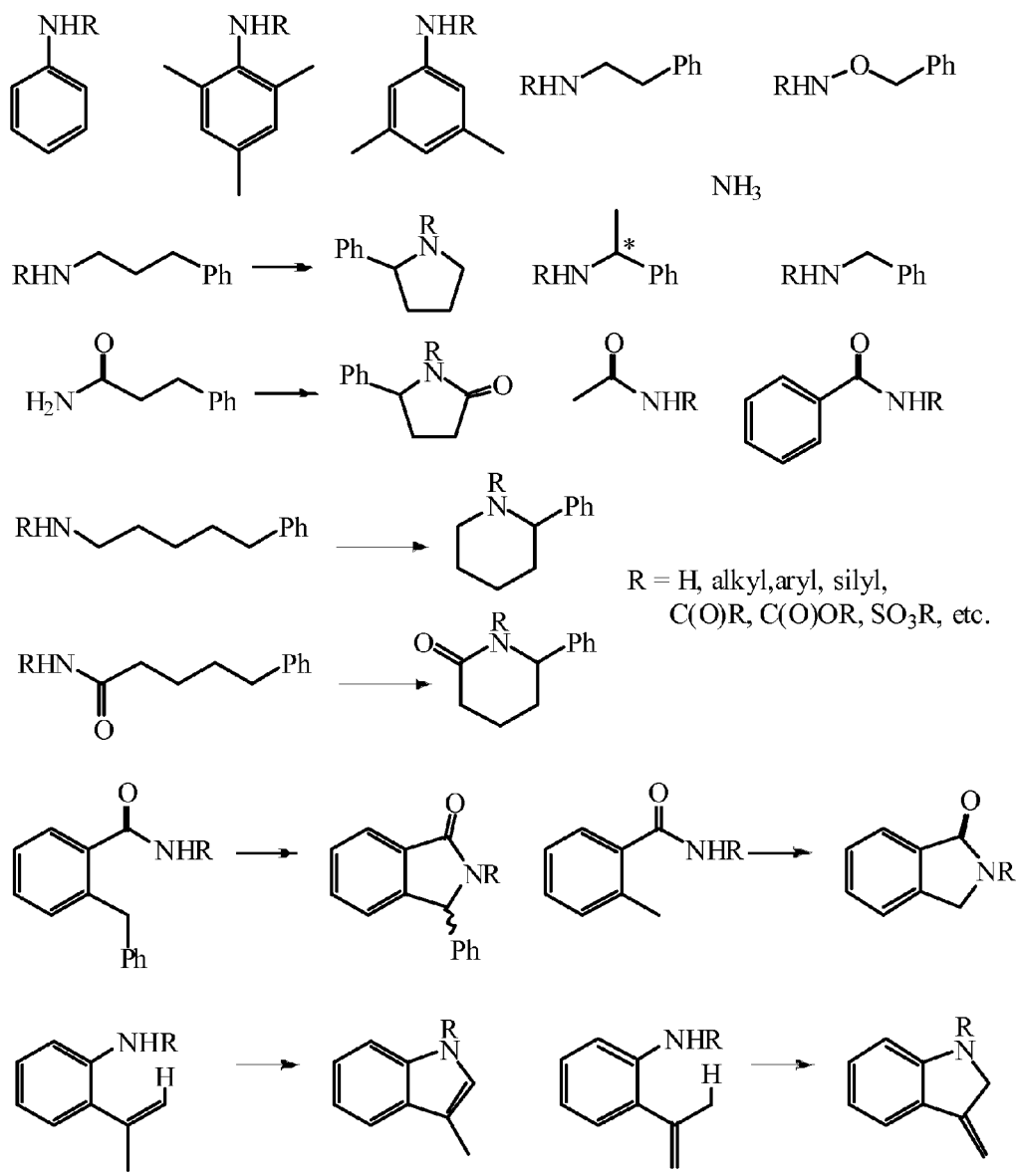
FIG. 7 depicts examples of primary and secondary amines (and in some cases the C—H amination products formed therefrom) which may be useful in the disclosed inter- and intramolecular C—H amination reactions.

In addition to ammonia, a wide number of primary and secondary amines, and amides, could be amenable to this new methodology. In certain embodiments, the amine is an alkyl amine, a cycloalkyl amine, a N-containing heterocycle, an alkenyl amine, an alkynyl amine, an aryl amine, a heteroaryl amine, an aralklyl amine, a heteroaralkyl amine. Similarly substituted amides may also be used (e.g., alkyl amides and aryl amides). For example, primary and secondary amines and amides amenable to intermolecular or intramolecular C—H amination (and their resulting products) include those shown in FIG. 7.

In certain embodiments, the amine or amide is represented by:

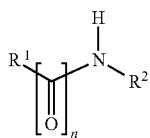

wherein, $R^1$ is hydrogen, alkyl, alkenyl, alkynyl, aryl, heteroaryl, aralkyl or heteroaralkyl; $R^2$ is hydrogen, alkyl, alkenyl, alkynyl, aryl, heteroaryl, aralkyl or heteroaralkyl; or $R^1$ and $R^2$ taken together with the atoms to which they are bound, form a five, six or seven membered ring which contains 0-2 heteroatoms and is optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano; and n is 0 or 1.

In certain embodiments, hydroxyamines (such as

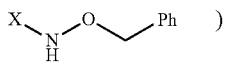 )

be used. For some hydroxyamines, it may not be necessary to add an oxidant to the reaction.

In certain embodiments, chiral amines, such

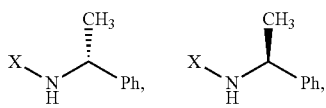

as can be used. It is expected that chiral amines will retain their stereochemistry.

In certain embodiments, when the amine contains two N—H functionalities, double C—H aminiation is possible.

In certain embodiments, the amine is selected from the group consisting of

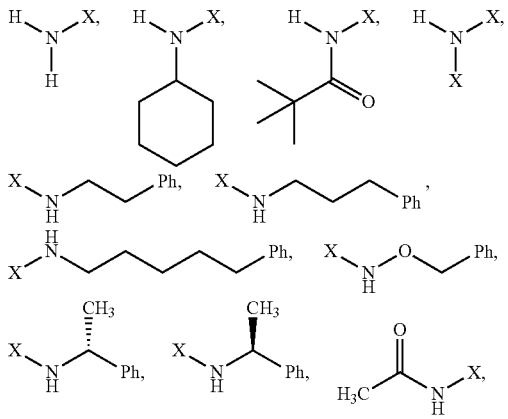

-continued

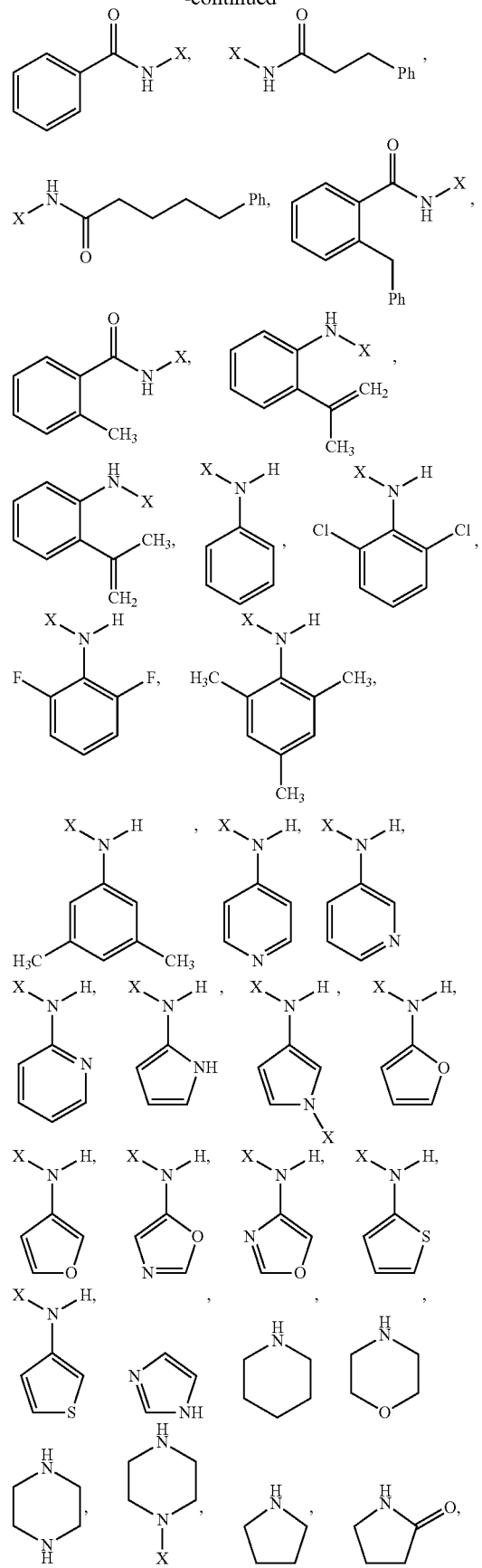

-continued

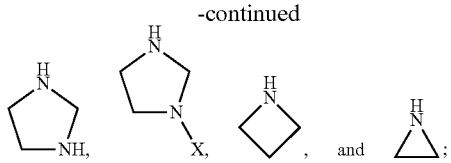

wherein X is hydrogen, alkyl, fluoroalkyl, aryl, aralkyl, heteroaryl, heteroaralkyl, silyl, carbonyl, ester, thioester, sulfonyl, sulfonate, or amide.

III. SUBSTRATES

Figure 8:
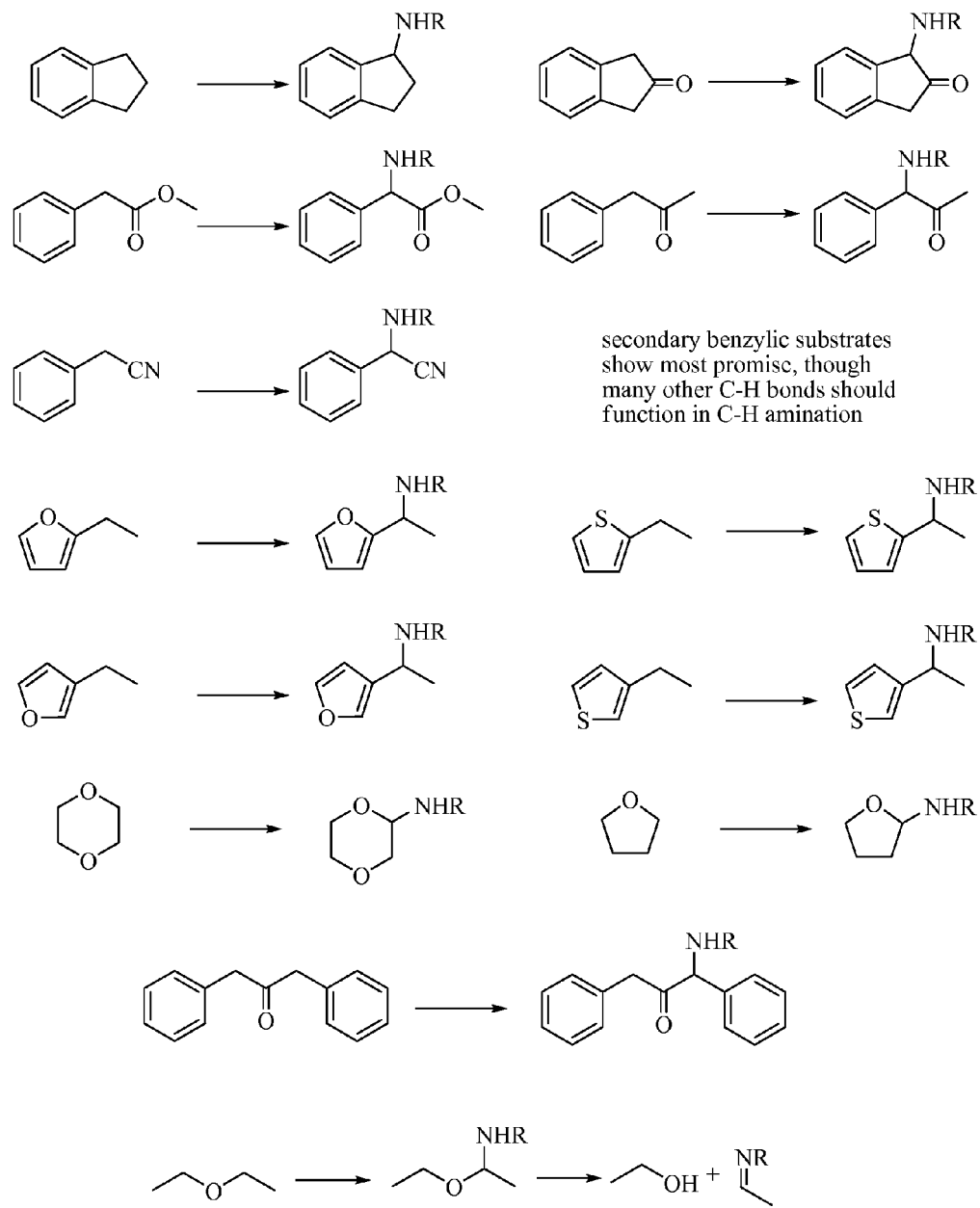
FIG. 8 depicts examples of substrates with reactive C—H bonds (and in some cases the C—H amination products formed therefrom) which may be useful in the disclosed C—H amination reactions.

A wide range of C—H bonds should be amenable to the C—H amination reactions described herein, with selectivity likely to follow trends in C—H bond strength (weaker C—H bond resulting in faster reaction time). For instance, substrates which are amenable to amination reactions described herein (and their resulting aminated products) are shown in FIG. 8.

In certain embodiments, the substrate comprising a reactive C—H bond is represented by:

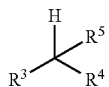

wherein, $R^3$ is alkyl, alkenyl, alkynyl, aryl, heteroaryl, aralkyl, heteroaralkyl, carbocycyl, heterocycyl, polycycyl, carbonyl, ester or ether; $R^4$ is hydrogen, alkyl, alkenyl, alkynyl, aryl, heteroaryl, aralkyl, heteroaralkyl, carbocycyl, heterocycyl, polycycyl, carbonyl, ester or ether; or $R^3$ and $R^4$ taken together are oxo (i.e., the substrate is an aldehdye: $HC(=O)R^5$); $R^5$ is hydrogen, alkyl, alkenyl, alkynyl, aryl, heteroaryl, aralkyl, heteroaralkyl, carbocycyl, heterocycyl, polycycyl, carbonyl, ester or ether; and the substrate is optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

In other embodiments, the substrate is a cyclopropane, cyclobutane, cyclopentane, cyclohexane, indane, 2-oxoindane, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactone, lactam, azetidinone, pyrrolidinone, sultam, or sultone; and the substrate is optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

In certain embodiments, the substrate is selected from the group consisting of

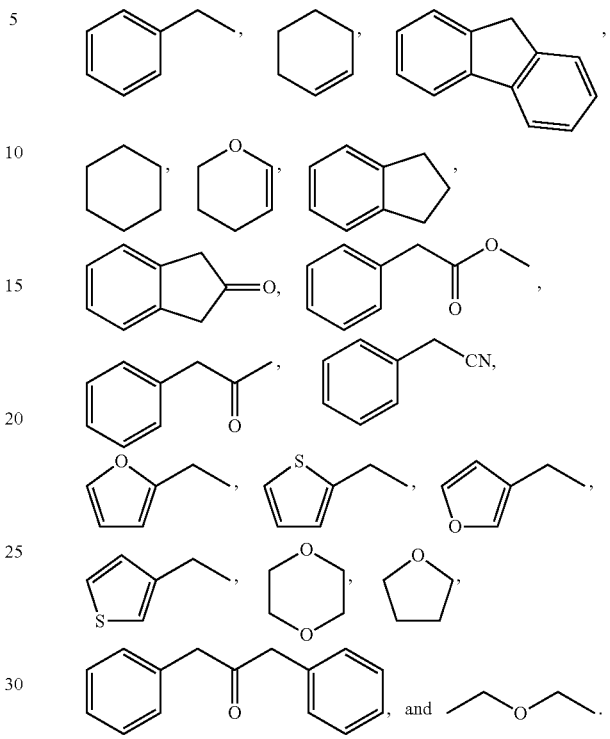

Aldehyde-Containing Substrates. As noted above, when $R^3$ and $R^4$ are oxo, the substate is an aldehyde ($HC(=O)R^5$). The product of the amination of an aldehyde is an amide ($R^1R^2NC(=O)R^5$). In certain embodiments, the substate may be an alkyl aldehyde, an aryl aldehyde, a heteroaryl aldehyde, an aralkyl aldehyde or a heteroaralkyl aldehyde.

Figure 10:
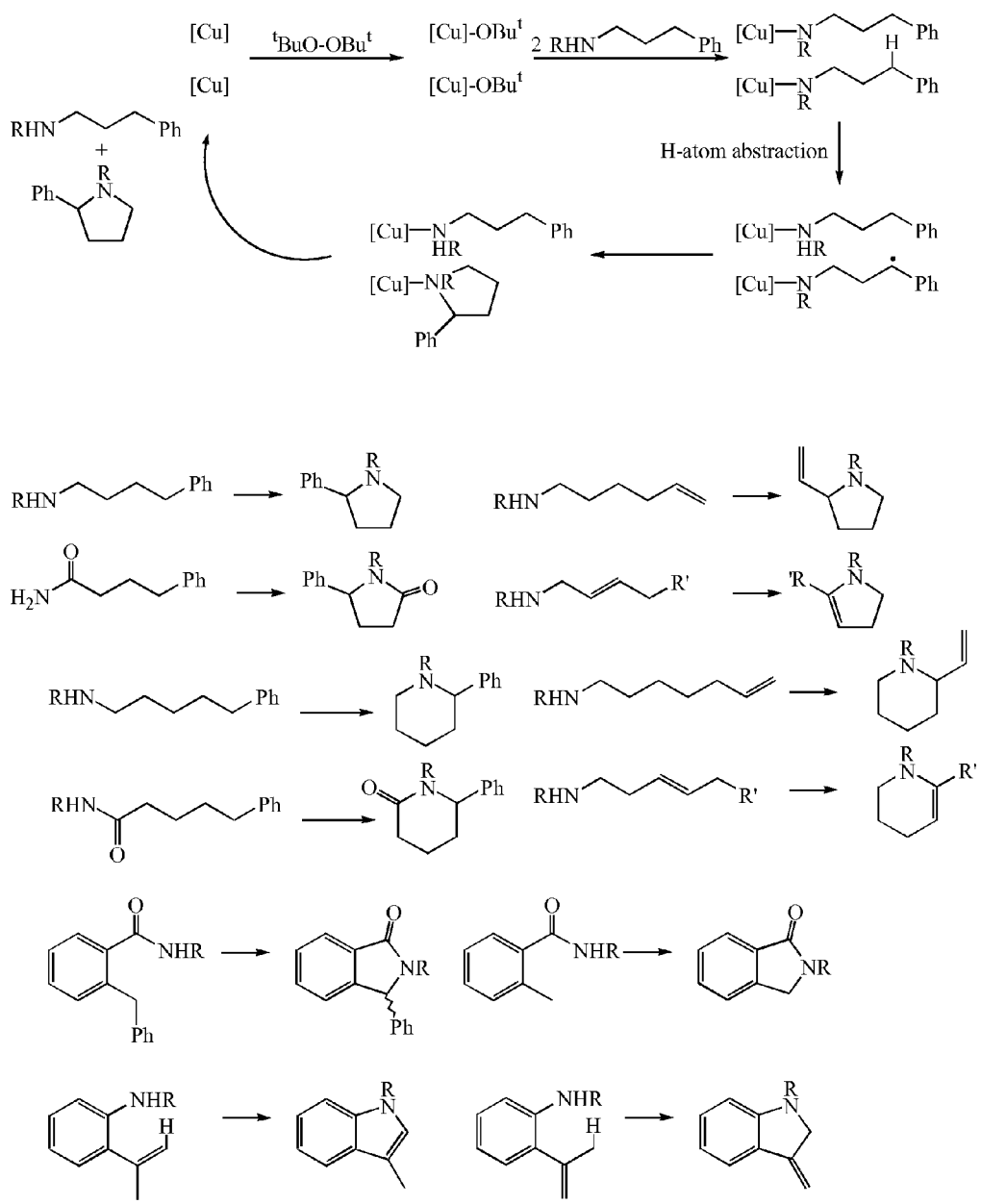
FIG. 10 depicts a proposed mechanism for intramolecular aminations; and examples of substrates aminable thereto.

Amine-Containing Substrates. When the substrate with the reactive C—H bond also contains an amine, cyclizations may be envisioned (especially at dilute concentrations and higher catalyst loadings, perhaps under slow addition of the amine-containing substrate). Maximizing the proportion of the amine bound to the copper catalyst as a copper amide will favor abstraction of a C—H bond from the copper-bound amide, allowing for cyclization (FIG. 10). Representative substrates amenable to intramolecular cyclization are shown in FIG. 10.

Figure 11:
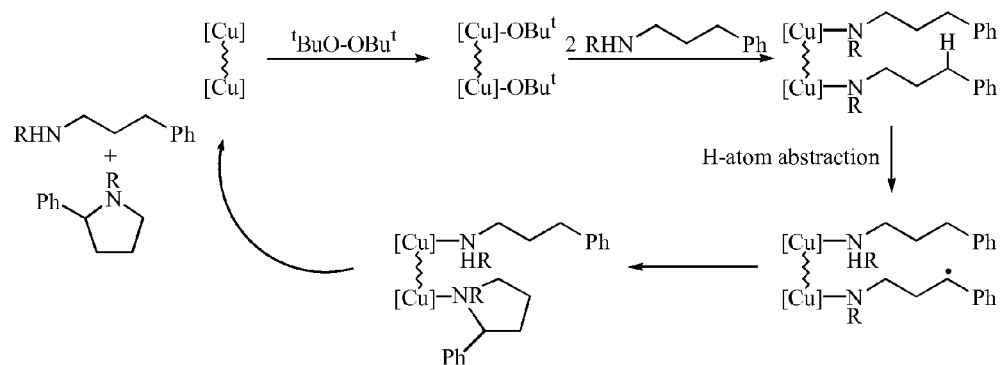
FIG. 11 depicts a proposed mechanism for intermolecular amination using a class of catalysts in which two metal centers are tethered together.

Owing to the C—H abstraction/rebound mechanism that is likely operative in this C—H amination reaction, a class of catalysts in which two copper centers are tethered together would be particularly promising for these cyclization reactions. For the most efficient intramolecular reactions, a C—H bond would need to be abstracted from an amine already bound to the catalyst as an amide (e.g., $[Cu]-NR^1R^2$) so that the radical formed may efficiently cyclize with the copper-amide (FIG. 11). Suitable catalysts are tethered together in some fashion as to keep two copper centers in close vicinity (ca. 4-5 Å), as discussed in the Catalyst section below.

Substrates for Preparing Polyamines. Polyamine materials have been widely used in many areas ranging from commodity industry applications to home-and-personal care and pharmaceutical uses largely due to their cationic and hydrogen bonding properties. The cationic and the hydrogen bonding characteristics are given by the amine functionality and are modulated by the amine content, which also dictates the charge density on the material. In many applications, higher amine content leads to higher efficacy.

In a system not optimized for intramolecular ring closure (as discussed above), oligomerization or polymerization may take place when the amine substrate possesses a C—H bond easily amenable to functionalization.

IV. LIGANDS AND CATALYSTS

As noted above, the catalysts employed are thought to involve complexes which can provide a [transition metal]-$NR^1R^2$ intermediate to give an organic radical (R.) which can then combine with the [transition metal]-$NR^1R^2$ intermediate to yield an amine. The following are some important aspects of catalysts contemplated by certain embodiments of the present invention.

1. N-Aryl β-Diketiminate Catalysts

The entire family of N-aryl β-diketiminate catalysts, such as those represented by Formula I (below) may be used. With reference to the structure of Formula I, it is important in certain embodiments that the substituents $X^1$-$X^4$ should not contain benzylic C—H bonds; however, aryl C—H bonds are not problematic. $R^{17}$-$R^{19}$ may have H atoms; sample $R^{17}$-$R^{19}$ substituents include, but are not limited to, hydrogen, methyl, trifluoromethyl, phenyl and t-butyl. M is a transition metal and L is a Lewis base, such as copper(benzene). As discussed below, the catalyst may be manipulated via electronic tuning to make it more or less electron-rich.

In addition, it has been observed that the N-aryl β-diketiminate catalysts aggregate upon isolation under certain preparation conditions. It is also proposed that certain aggregates are stable and may be used directly in amination reactions. A procedure for preparing and isolating one such aggregate, $\{[Cl_2NN]Cu\}_2(benzene)_{0.8}$, is provided herein. While the following catalysts of formula I are presented as monomers, the present invention also encompases the use of such catalysts as aggregates (such as dimers). The same is true for the other catalyst types (such as those of formula II or III) discussed below.

One aspect of the present invention relates to a catalyst represented by Formula I or its enantiomer:

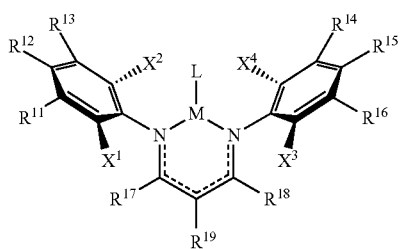

I wherein, $R^{11}$ to $R^{19}$ are independently selected from the group consisting of hydrogen, alkyl, aryl, aralkyl, halogen, cyano, nitro, and trifluoromethyl; $X^1$ to $X^4$ are independently selected from the group consisting of hydrogen, halogen or perhaloalkyl; L is absent or a Lewis base; and M is a transition metal.

In certain embodiments, the present invention relates to the aforementioned compound and any attendant definitions, wherein M is copper.

In certain embodiments, the present invention relates to the aforementioned compound and any attendant definitions, wherein M is copper(I).

In certain embodiments, the present invention relates to the aforementioned compound and any attendant definitions, wherein M is copper(II).

In certain embodiments, the present invention relates to the aforementioned compound and any attendant definitions, wherein $R^{17}$-$R^{19}$ represents independently for each occurrence hydrogen, methyl, trifluoromethyl, phenyl, or t-butyl.

In certain embodiments, the present invention relates to the aforementioned compound and any attendant definitions, wherein $R^{17}$ and $R^{18}$ represent t-butyl.

In certain embodiments, the present invention relates to the aforementioned compound and any attendant definitions, wherein $R^{17}$ and $R^{18}$ represent trifluoromethyl.

In certain embodiments, the present invention relates to the aforementioned compound and any attendant definitions, wherein $R^{19}$ is hydrogen.

In certain embodiments, the present invention relates to the aforementioned compound and any attendant definitions, wherein $X^1$-$X^4$ are independently for each occurrence halogen or perfluoroalkyl.

In certain embodiments, the present invention relates to the aforementioned compound and any attendant definitions, wherein $X^1$-$X^4$ are independently for each occurrence Cl, I, Br, or $CF_3$.

In certain embodiments, the present invention relates to the aforementioned compound and any attendant definitions, wherein $X^1$-$X^4$ are Cl.

In certain embodiments, the present invention relates to the aforementioned compound and any attendant definitions, wherein $X^1$-$X^4$ are $CF_3$.

In certain embodiments, the present invention relates to the aforementioned compound and any attendant definitions, wherein M is Cu, and $X^1$-$X^4$ are Cl.

In certain embodiments, the present invention relates to the aforementioned compound and any attendant definitions, wherein M is Cu, and $X^1$-$X^4$ are $CF_3$.

In certain embodiments, the present invention relates to the aforementioned compound and any attendant definitions, wherein L is absent.

In certain embodiments, the present invention relates to the aforementioned compound and any attendant definitions, wherein L is solvent.

In certain embodiments, the present invention relates to the aforementioned compound and any attendant definitions, wherein L is aromatic.

In certain embodiments, the present invention relates to the aforementioned compound and any attendant definitions, wherein L is an olefin.

In certain embodiments, the present invention relates to the aforementioned compound and any attendant definitions, wherein L is benzene.

In certain embodiments, the present invention relates to the aforementioned compound and any attendant definitions, wherein M is Cu, $X^1$-$X^4$ are Cl, and L is benzene.

In certain embodiments, the present invention relates to the aforementioned compound and any attendant definitions, wherein M is Cu, $X^1$-$X^4$ are $CF_3$, and L is benzene.

In certain embodiments, the present invention relates to the aforementioned compound and any attendant definitions, wherein the catalyst is selected from the group consisting of

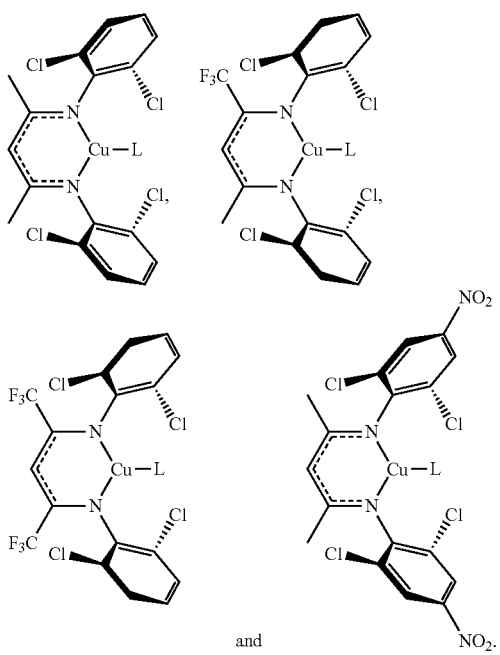

2. Anionic β-Diketiminate-like Catalysts

In certain embodiments, the catalysts of the present invention may also be represented by Formula IIa or IIb (below).

One aspect of the present invention relates to a catalyst represented by Formula IIa or its enantiomer:

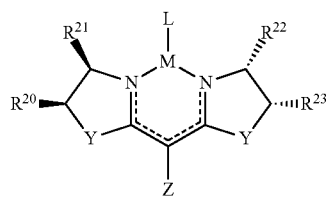

IIa wherein, $R^{20}$ is hydrogen, alkyl, aryl or heteroaryl; $R^{21}$ is alkyl, aryl or heteroaryl; $R^{22}$ is hydrogen, alkyl, aryl or heteroaryl; $R^{23}$ is alkyl, aryl or heteroaryl; Y is O, S, $CH_2$ or $CH_2CH_2$; Z is hydrogen or cyano; L is absent or a Lewis base; and M is a transition metal.

In certain embodiments, the present invention relates to the aforementioned compound and any attendant definitions, wherein $R^{20}$ is hydrogen.

In certain embodiments, the present invention relates to the aforementioned compound and any attendant definitions, wherein $R^{20}$ is phenyl.

In certain embodiments, the present invention relates to the aforementioned compound and any attendant definitions, wherein $R^{21}$ is phenyl.

In certain embodiments, the present invention relates to the aforementioned compound and any attendant definitions, wherein $R^{22}$ is phenyl.

In certain embodiments, the present invention relates to the aforementioned compound and any attendant definitions, wherein $R^{23}$ is hydrogen.

In certain embodiments, the present invention relates to the aforementioned compound and any attendant definitions, wherein $R^{23}$ is phenyl.

In certain embodiments, the present invention relates to the aforementioned compound and any attendant definitions, wherein Y is O.

In certain embodiments, the present invention relates to the aforementioned compound and any attendant definitions, wherein Z is hydrogen.

In certain embodiments, the present invention relates to the aforementioned compound and any attendant definitions, wherein Z is cyano.

In certain embodiments, the present invention relates to the aforementioned compound and any attendant definitions, wherein M is copper.

In certain embodiments, the present invention relates to the aforementioned compound and any attendant definitions, wherein M is copper(I).

In certain embodiments, the present invention relates to the aforementioned compound and any attendant definitions, wherein M is copper(II).

In certain embodiments, the present invention relates to the aforementioned compound and any attendant definitions, wherein L is absent.

In certain embodiments, the present invention relates to the aforementioned compound and any attendant definitions, wherein L is solvent.

In certain embodiments, the present invention relates to the aforementioned compound and any attendant definitions, wherein L is aromatic.

In certain embodiments, the present invention relates to the aforementioned compound and any attendant definitions, wherein L is an olefin.

In certain embodiments, the present invention relates to the aforementioned compound and any attendant definitions, wherein L is benzene.

In certain embodiments, the present invention relates to the aforementioned compound and any attendant definitions, wherein the catalyst is selected from the group consisting of

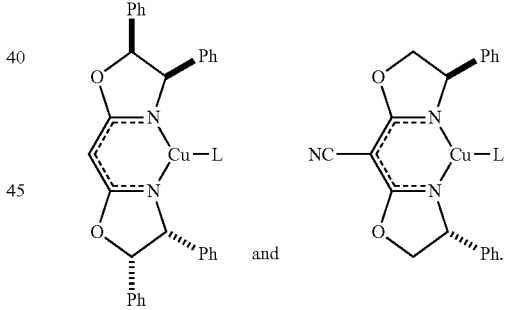

One aspect of the present invention relates to a catalyst represented by Formula IIb or its enantiomer:

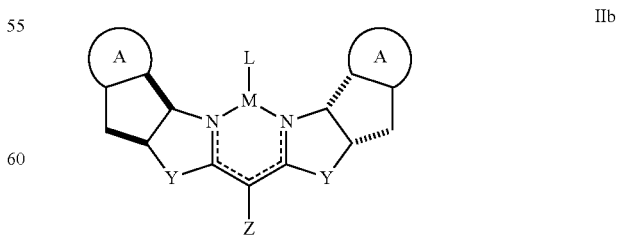

IIb wherein, A is aryl or heteroaryl; Y is O, S, $CH_2$ or $CH_2CH_2$; Z is hydrogen or cyano; L is absent or a Lewis base; and M is a transition metal.

In certain embodiments, the present invention relates to the aforementioned compound and any attendant definitions, wherein A is phenyl.

In certain embodiments, the present invention relates to the aforementioned compound and any attendant definitions, wherein Y is O.

In certain embodiments, the present invention relates to the aforementioned compound and any attendant definitions, wherein Z is hydrogen.

In certain embodiments, the present invention relates to the aforementioned compound and any attendant definitions, wherein M is copper.

In certain embodiments, the present invention relates to the aforementioned compound and any attendant definitions, wherein M is copper(I).

In certain embodiments, the present invention relates to the aforementioned compound and any attendant definitions, wherein M is copper(II).

In certain embodiments, the present invention relates to the aforementioned compound and any attendant definitions, wherein L is absent.

In certain embodiments, the present invention relates to the aforementioned compound and any attendant definitions, wherein L is solvent.

In certain embodiments, the present invention relates to the aforementioned compound and any attendant definitions, wherein L is aromatic.

In certain embodiments, the present invention relates to the aforementioned compound and any attendant definitions, wherein L is an olefin.

In certain embodiments, the present invention relates to the aforementioned compound and any attendant definitions, wherein L is alkyoxy.

In certain embodiments, the present invention relates to the aforementioned compound and any attendant definitions, wherein L is t-butoxy.

In certain embodiments, the present invention relates to the aforementioned compound and any attendant definitions, wherein the catalyst is

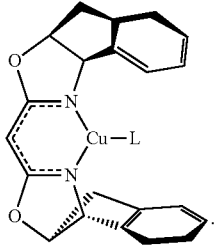

3. Catalysts Containing Neutral Ligands and Cationic Metal Sources

Neutral ligands when combined with cationic copper sources may also form active catalysts for C—H amination. For instance, phenyl- and t-butyl-substituted bis(oxazoline) ligands (see III below) when combined in-situ with [Cu(NCMe)$_4$]BF$_4$ result in active catalysts for C—H amination (See Exemplificaiton: ligands 8 and 9). Since both bis(oxazolines) form active catalysts, it is anticipated that a broad class of poly(amines) and poly(imines) may work. Chiral bis(oxazolines) may also be used; the use of chiral ligands in general is discussed below.

One aspect of the present invention relates to a catalyst represented by Formula III or its enantiomer:

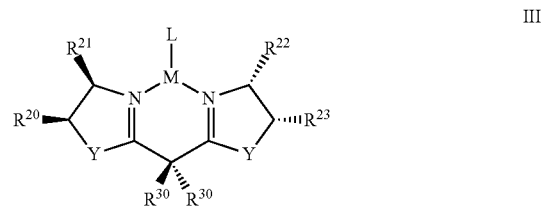

wherein, $R^{20}$ is hydrogen, alkyl, aryl or heteroaryl; $R^{21}$ is alkyl, aryl or heteroaryl; $R^{22}$ is hydrogen, alkyl, aryl or heteroaryl; $R^{23}$ is alkyl, aryl or heteroaryl; $R^{30}$ is alkyl or both $R^{30}$ taken together are a cycloakyl ring; Y is O, S, CH$_2$ or CH$_2$CH$_2$; L is a Lewis base; and M is a transition metal.

In certain embodiments, the present invention relates to the aforementioned compound and any attendant definitions, wherein $R^{20}$ is hydrogen.

In certain embodiments, the present invention relates to the aforementioned compound and any attendant definitions, wherein $R^{21}$ is phenyl.

In certain embodiments, the present invention relates to the aforementioned compound and any attendant definitions, wherein $R^{21}$ is t-butyl.

In certain embodiments, the present invention relates to the aforementioned compound and any attendant definitions, wherein $R^{22}$ is phenyl.

In certain embodiments, the present invention relates to the aforementioned compound and any attendant definitions, wherein $R^{22}$ is t-butyl.

In certain embodiments, the present invention relates to the aforementioned compound and any attendant definitions, wherein $R^{23}$ is hydrogen.

In certain embodiments, the present invention relates to the aforementioned compound and any attendant definitions, wherein $R^{30}$ is alkyl.

In certain embodiments, the present invention relates to the aforementioned compound and any attendant definitions, wherein $R^{30}$ is methyl.

In certain embodiments, the present invention relates to the aforementioned compound and any attendant definitions, wherein Y is O.

In certain embodiments, the present invention relates to the aforementioned compound and any attendant definitions, wherein M is copper.

In certain embodiments, the present invention relates to the aforementioned compound and any attendant definitions, wherein M is copper(I).

In certain embodiments, the present invention relates to the aforementioned compound and any attendant definitions, wherein M is copper(II).

In certain embodiments, the present invention relates to the aforementioned compound and any attendant definitions, wherein L is absent.

In certain embodiments, the present invention relates to the aforementioned compound and any attendant definitions, wherein L is solvent.

In certain embodiments, the present invention relates to the aforementioned compound and any attendant definitions, wherein L is aromatic.

In certain embodiments, the present invention relates to the aforementioned compound and any attendant definitions, wherein L is an olefin.

In certain embodiments, the present invention relates to the aforementioned compound and any attendant definitions, wherein L is NC(alkyl).

In certain embodiments, the present invention relates to the aforementioned compound and any attendant definitions, wherein L is NC(methyl).

In certain embodiments, the present invention relates to the aforementioned compound and any attendant definitions, wherein the catalyst is selected from the group consisting of

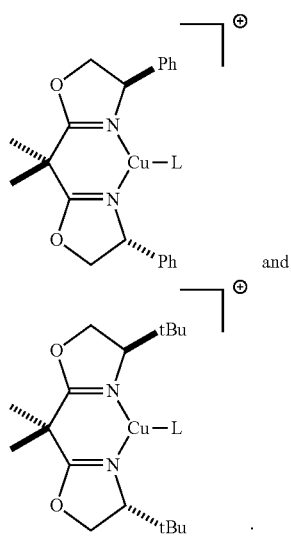

and

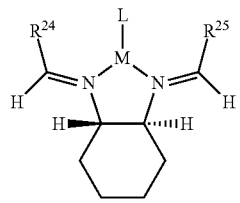

One aspect of the present invention relates to a catalyst represented by Formula IV or its enantiomer:

$$\text{IV}$$

wherein $R^{24}$ is aryl or heteroaryl; $R^{25}$ is aryl or heteroaryl; L is a Lewis base; and M is a transition metal.

In certain embodiments, the present invention relates to the aforementioned compound and any attendant definitions, wherein $R^{24}$ is phenyl optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

In certain embodiments, the present invention relates to the aforementioned compound and any attendant definitions, wherein $R^{24}$ is a 2,6-disubstituted phenyl; and the substituents are selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

In certain embodiments, the present invention relates to the aforementioned compound and any attendant definitions, wherein $R^{24}$ is a 2,6-dihalophenyl.

In certain embodiments, the present invention relates to the aforementioned compound and any attendant definitions, wherein $R^{25}$ is phenyl optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

In certain embodiments, the present invention relates to the aforementioned compound and any attendant definitions, wherein $R^{25}$ is a 2,6-disubstituted phenyl; and the substituents are selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

In certain embodiments, the present invention relates to the aforementioned compound and any attendant definitions, wherein $R^{25}$ is a 2,6-dihalo phenyl.

In certain embodiments, the present invention relates to the aforementioned compound and any attendant definitions, wherein M is copper.

In certain embodiments, the present invention relates to the aforementioned compound and any attendant definitions, wherein M is copper(I).

In certain embodiments, the present invention relates to the aforementioned compound and any attendant definitions, wherein M is copper(II).

In certain embodiments, the present invention relates to the aforementioned compound and any attendant definitions, wherein L is absent.

In certain embodiments, the present invention relates to the aforementioned compound and any attendant definitions, wherein L is solvent.

In certain embodiments, the present invention relates to the aforementioned compound and any attendant definitions, wherein L is aromatic.

In certain embodiments, the present invention relates to the aforementioned compound and any attendant definitions, wherein L is an olefin.

In certain embodiments, the present invention relates to the aforementioned compound and any attendant definitions, wherein L is NC(alkyl).

In certain embodiments, the present invention relates to the aforementioned compound and any attendant definitions, wherein L is NC(methyl).

In certain embodiments, the present invention relates to the aforementioned compound and any attendant definitions, wherein the catalyst is

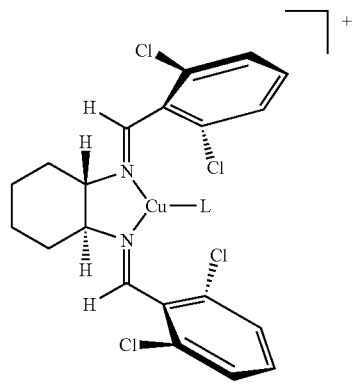

4. Catalysts Containing Non-Anionic Neutral Ligands

Figure 12:
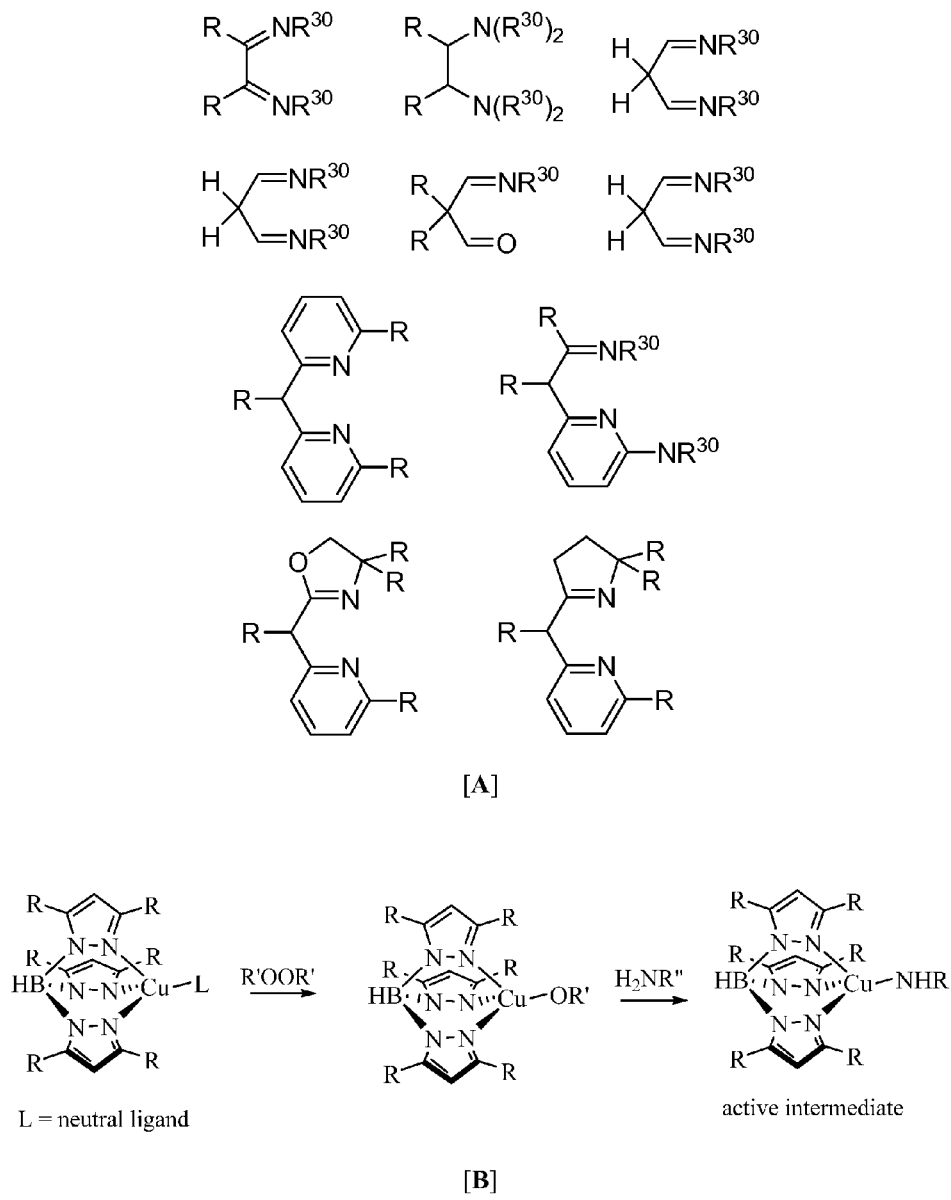
FIG. 12 depicts [A] selected neutral ligands which might be useful in amination reactions (wherein, independently for each occurrence, R is hydrogen, alkyl, fluoroalkyl, aryl, silyl, carbonyl, ester, thioester, sulfonyl, sulfonate, or amide; and $R^{30}$ is halogen, alkyl, alkenyl, alkynyl, hydroxyl, amino, nitro, thiol, imino, amido, carbonyl, silyl, ether, thioether, sulfonyl, selenoether, ketone, aldehyde, ester, fluoroalkyl, trifluoromethyl, or cyano); and [B] tris(pyrazoyl)borate complexes which might also be useful in amination reactions.

A number of neutral ligands which may or may not be converted to anionic ligands may function as amination catalysts. The catalysts must possess at least two arms that may simultaneously coordinate to a metal ion; they may possess more (e.g., tridendate ligands). Importantly, the catalysts should not possess $sp^3$-C—H bonds that may extend into the vicinity of the catalyst complex. Some representative ligand structures which meet these features are shown in FIG. 12A. In addition, a family of tris(pyrazolyl)borate complexes may conceivably work for the process (see FIG. 12B). For example, Peréz's work with brominate Tp complexes (3 Br on each pyrazolyl ring) creates systems active for C—H functionalization with PhI=NSO$_3$R. M. R. Fructos, S. Trofimenko, M. M. Días-Requejo, P. J. Pérez, *J. Am. Chem. Soc.* 2006, 128, 11784; and M. M. Díaz-Requejo, T. R. Belderraín, M. C. Nicasio, S. Trofimenko, P. J. Pérez, *J. Am. Chem. Soc.* 2003, 125, 12078.

"Linked" Catalysts. Linked complexes may be especially useful in intramolecular cyclization reactions (see FIG. 15B). Positioning the linker group distant from the metal binding site lessens the chemical demands as to the nature of the linking group. The catalysts in FIG. 15 show rigid o-phenylene linkers, though others with $sp^3$-hybridized bonds should not be ruled out since bis(oxazoline) catalyst 8 possesses benzylic C—H bonds but still catalyzes the C—H amination of ethylbenzene with $H_2NAr^F$ ($Ar^F$=3,5-(CF$_3$)$_2$C$_6$H$_3$).

5. Catalysts Prepared In Situ

Importantly, it is not necessary to use a pre-formed metal-containing catalyst consisting of one or more ligands and a metal ion. While the results provided herein relate to the direct use of the pre-synthesized β-diketiminato catalyst [Cl$_2$NN]Cu}$_2$(μ-benzene), active catalysts have also been prepared by mixting the β-diketimine ligand (H[Cl$_2$NN]) with CuOBut or other suitable sources of copper (FIG. 13A)

Optimized systems that employ more electron-withdrawing β-diketimine ligands such as [Cl$_2$NN$_{F6}$] or [Cl$_2$NO$_2$NN] can likely be combined with Cu$_2$O (copper(I) oxide, which is inexpensive and not air-sensitive) to generate the active catalyst [Cl$_2$NN$_{F6}$]Cu or [Cl$_2$NO$_2$NN]Cu (FIG. 13B).

6. Metals

While many of catalysts shown herein are bound to copper, any transition metal may be used to form the catalyst, e.g., a metal selected from one of Groups 3-12 of the Periodic Table or from the lanthanide series. However, in preferred embodiments, the metal will be selected from the group of late transition metals, e.g., preferably from Groups 5-12, in order to provide metal centers which are coordinatively unsaturated and not in their highest oxidation state. For example, suitable metals include Cu, Ag, Au, Pd, Co and Rh. In certain embodiments, particularly preferred metals include Cu and Ag.

Many related silver(I) complexes may be ammenable to this C—H functionalization reaction using related anionic and neutral complexes. For instance it has been shown that several Ag(I) salts work in the amination of C—H bonds with PhI=NTs. Z. Li, D. A. Capretto, R. Rahaman, C. He, *Angew. Chem.* 2007, 119, 5276; *Angew. Chem. Int. Ed.* 2007, 46, 5184; and Y. Cui, C. He, *Angew. Chem.* 2004, 116, 4306; *Angew. Chem. Int. Ed.* 2004, 43, 4210.

In addition, it is possible that an active catalyst may be formed from an air-stable copper(II) complex bearing the desired ligand such as {[Cl$_2$NN]Cu}$_2$(μ-OH)$_2$. Many copper (II) complexes exhibit greater air-stability than their copper (I) counterparts, making copper(II) an attractive metal for the storage and use of the catalysts.

7. Catalyst Optimization

A possible limitation to some of the amination reactions described herein is that the reactivity of some of the copper intermediates is a bit low and requires the use of neat hydrocarbon to achieve high yields. One way to address this problem is by altering the catalyst ligand substituents. In otherwords, ligand substituents should be chosen to optimize the reactivity of the catalyst and the catalyst's stability; the catalyst should be tuned. In general, "tuning" refers to both altering the steric bulk of the ligand to limit the approach of the substrate, utilizing steric repulsions between the substrate and ligand substituents, and altering the electronic characteristics of the ligand to influence electronic interactions between the substrate and the ligand, as well as the rate and mechanism of the catalyzed reaction.

In addition, the choice of substituent may also effect catalyst stability; in general, bulkier substituents are found to provide higher catalyst turnover numbers. Furthermore, the choice of substituent on the ligand can also be used to influence the solubility of the catalyst in a particular solvent system.

As mentioned briefly above, the choice of ligand substituents can also effect the electronic properties of the catalyst. Substitution of the ligand with electron-rich (electron-donating) moieties (including, for example, alkoxy or amino groups) increases the electron density of the ligand and at the metal center. Conversely, electron-withdrawing moieties (for example, chloro or trifluoromethyl groups) on the ligand result in lower electron density of the ligand and metal center. Choice of appropriate substituents thus makes possible the "tuning" of the reaction rate.

Figure 9:
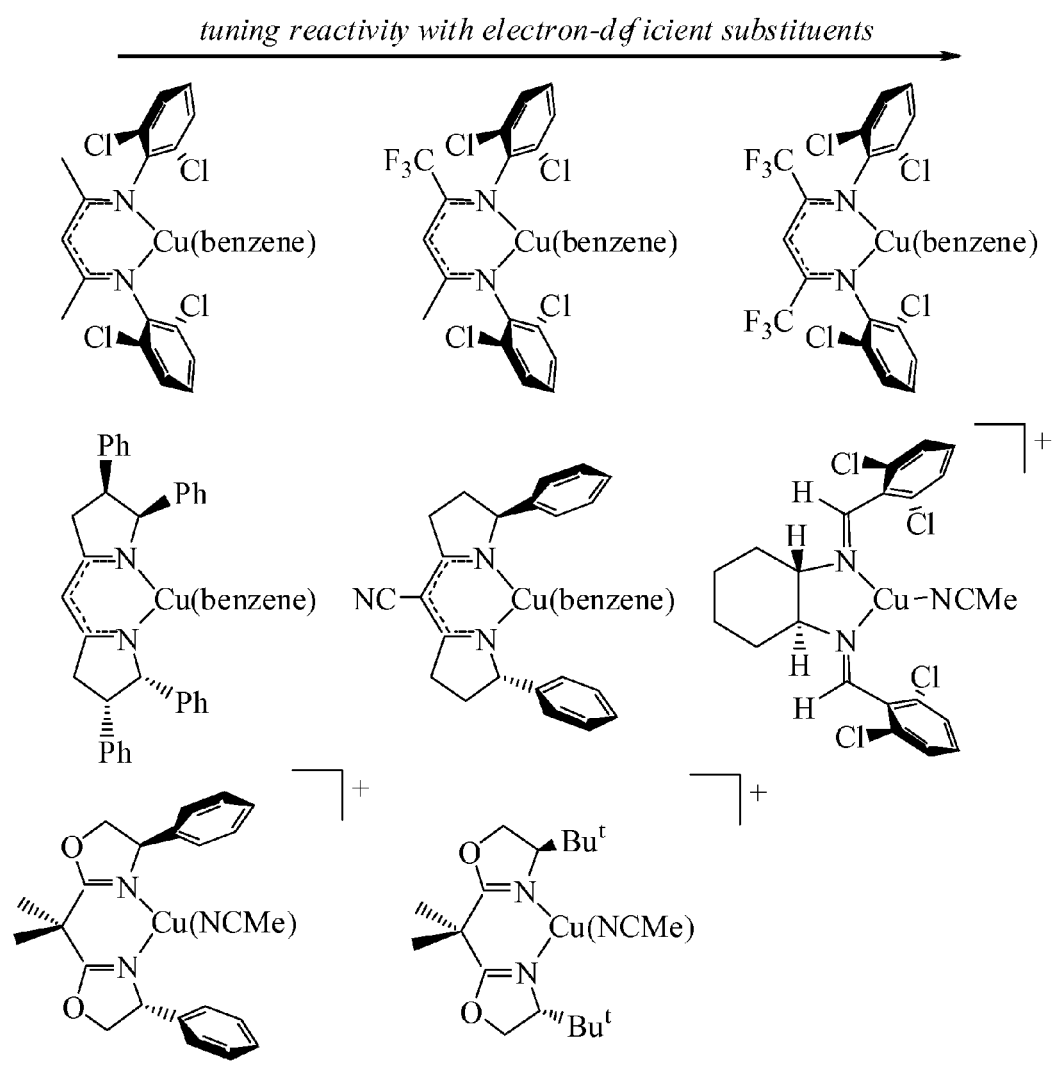
FIG. 9 depicts examples of Cu(I)-containing catalysts which may be useful in the disclosed C—H amination reactions.

For example, since the presence of electron-withdrawing substituents has been shown to increase the reactivity of many C—H amination catalysts, adding CF$_3$ groups to the backbone of the catalyst may yield improved catalysts. Literature procedures have been used to prepare the corresponding o-Me$_2$Ph derivatives with these fluorinated backbones. Examples of catalysts are shown in FIG. 9.

In certain embodiments, the presence of electron-withdrawing substituents on the ligand in the catalyst are highly desirable. DFT calculations demonstrate that the incorporation of electron-withdrawing groups into the ligand generate copper-amide intermediates [Cu]—NR$^1$R$^2$ which are more potent towards C—H bond abstraction than a comparable catalyst structure without (see FIG. 14).

A desirable ligand that results in similar energies for C—H abstraction as the [Cl$_2$NNF$_6$] is [Cl$_2$NO$_2$NN], conceivably prepared from the commercially available 2,6-dichloro-4-nitroaniline and 2,4-pentanedione (see FIG. 15A). The added expected reactivity of the copper-nitrene or copper-amide intermediates should allow one to both lower the substrate loading as well as the catalyst loading helps to prevent diazene formation. In a complementary approach, neutral diimines (and perhaps diamines) coupled with copper(I) salts should provide electrophilic complexes amenable to this C—H amination protocol. In fact, use of bis(oxazolines)

(ligands 8 and 9, see Exemplification below) with a copper(I) salt gave reasonable yields of C—H amination products.

8. Chiral Ligands

Numerous chiral ligands exist for a host of established asymmetric transformations catalyzed by copper salts. In particular, many of these ligands are $C_2$-symmetric diamines or diiminates bearing strong similarity to the successful β-diketiminates described herein. As described in the Exemplification, the commercially available bis(oxazoline) ligand 8 with [Cu(MeCN)$_4$]PF$_6$ (10 mol % each) can be used to catalyze the C—H amination of ethylbenzene using the anilines described in 50-60% yield (unoptimized) employing a similar protocol. Similar to the β-diketiminato system, no diazene byproduct was observed with the electron-poor aniline $H_2NAr^F$. Other diamines also work, such as the commercially available diimine 9. These results demonstrates the exceptional promise of this approach owing to the wide number of successful chiral ligands available for copper.

It should be noted that the use of the same and related bis(oxazoline) ligands in conjunction with copper salts have induced good to excellent (up to 99%) enantiomeric excess in the amination and oxidation of allylic substrates such as cyclopentene and cyclohexene using activated amines (ArSO$_2$NHC(O)O$_2$Bu$^t$) or perbenzoates (ArC(O)OOBu$^t$), respectively (J. S. Clark, C. Roche, *Chem. Commun.* 2005, 5175; and M. B. Andrus, Z Zhou *J. Am. Chem. Soc.* 2002, 124, 8806.).

V. OXIDIZING AGENTS

The amination reactions of the present invention may utilize a wide variety of oxidants. For example, the oxidant may be selected from the group consisting of peroxides, oxygen, halogens (e.g., $I_2$), pseudo-halogen compounds (e.g., ClSCN, ISCN, INCO, (SCN)$_2$, IN$_3$, INO$_3$, and BrN$_3$), hypervalent iodide compounds (e.g., $IO_4^-$, PhI=O, PhI(O$_2$CR)$_2$ and PhI=NR, wherein R is an electron-withdrawing group), benzoquinones, and inorganic oxidation couples (such as Cu$^+$/O$_2$).

Peroxides as Oxidants. In certain embodiments the oxidant used is a peroxide. In certain embodiment, the oxidant is a peroxide represented by R$^6$—O—O—R$^6$, wherein R$^6$ is hydrogen, alkyl, alkenyl, alkynyl, aralkyl, aryl or heteroaryl. In certain embodiment, the oxidant is a peroxide represented by H—O—O—R$^6$, wherein R$^6$ is hydrogen, alkyl, alkenyl, alkynyl, aralkyl, aryl or heteroaryl. In certain embodiments, the oxidant is tert-butyl peroxide ($^t$Bu—O—O—Bu$^t$). In certain embodiments, the oxidant is hydrogen peroxide (H—O—O—H).

Figure 16:
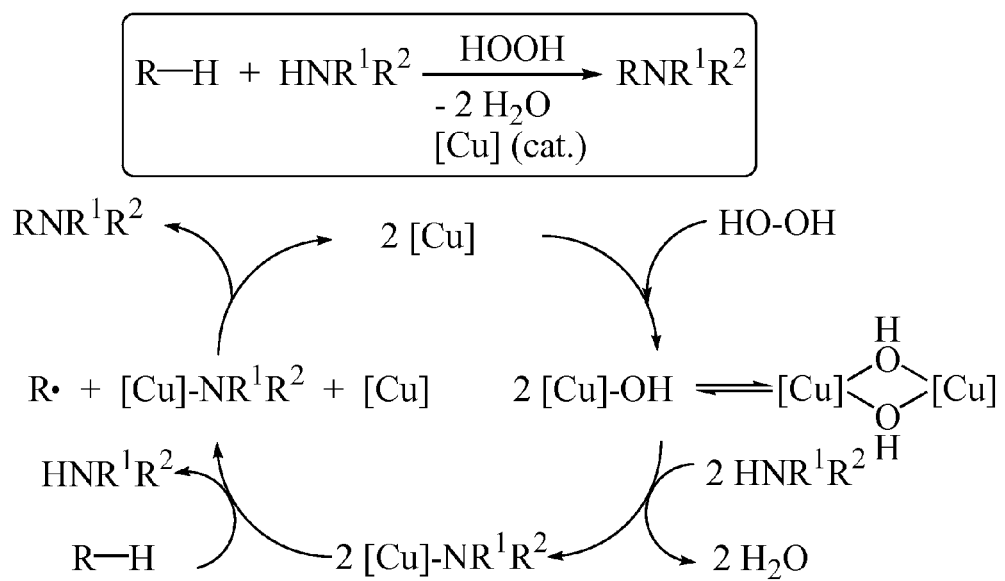
FIG. 16 depicts a proposed catalytic cycle for copper-catalyzed C—H amination with hydrogen peroxide.
Figure 17:
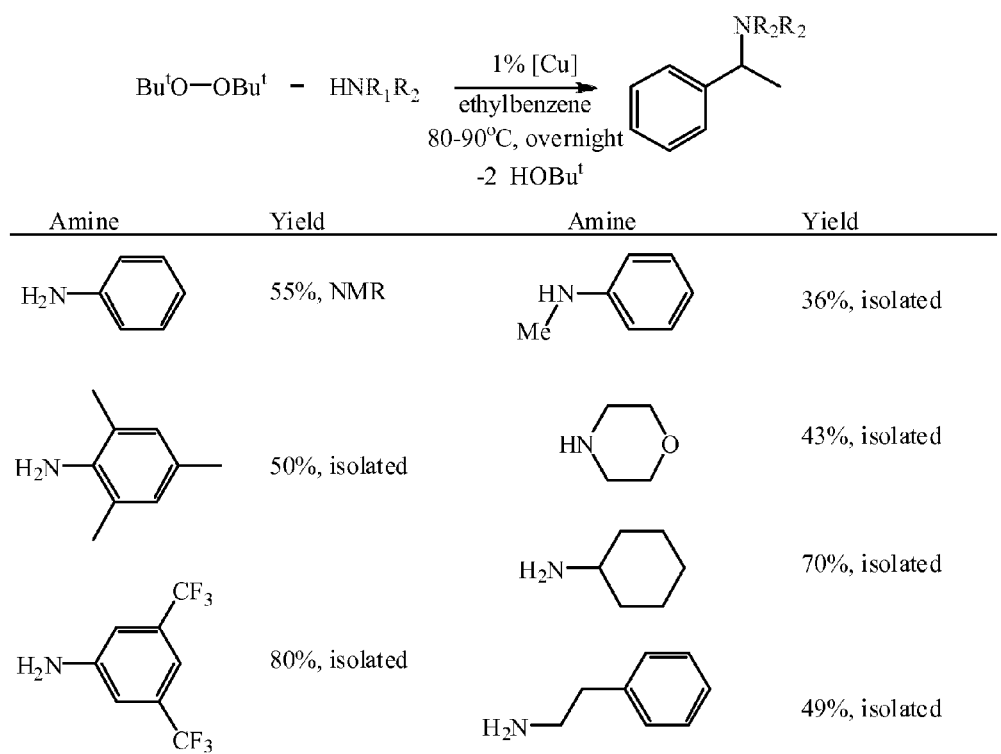
FIGS. 17, 18 and 19 depict selected results of aminations using the [Cl$_2$NN]Cu catalyst, which were typically run with 1 mmol of amine substrate. In the case of neat ethylbenzene solvent, 20 mL was typically employed. When heptane was used as a solvent, ca. 4 mL was used.
Figure 18:
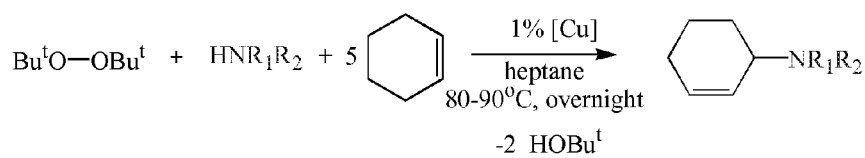
Figure 19:
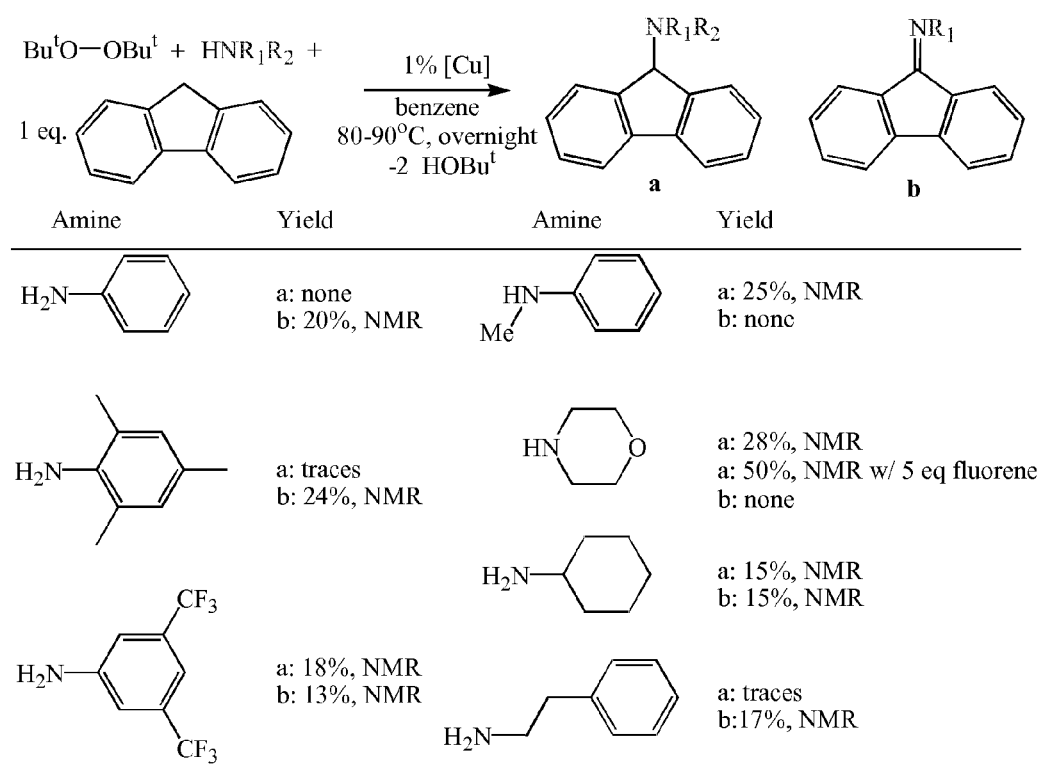

Hydrogen Peroxide as Oxidant. The incorporation of electron-withdrawing substituents into the backbone of β-diketiminato-like ligand complexes described above also accomplishes another goal: it makes the complex less susceptible to protonation by water. Considering the proposed catalytic cycle, this should enable the use of the environmentally friendly $H_2O_2$ as an oxidant. Rather than proceeding through [Cu]—OBu$^t$ intermediates, [Cu]—OH intermediates instead would be formed, releasing $H_2O$ upon reaction with amine. DFT modeling demonstrates that Cu—N bond formation via the reaction between [Cu]—OH and $H_2NPh$ is even more thermodynamically favored than with the corresponding [Cu]—OBu$^t$ intermediates. A proposed mechanism is provided in FIG. 16.

VI. SELECTED AMINATION REACTIONS

One aspect of the invention relates to a method of amination or amidation, comprising the step of: combining a substrate, comprising a reactive C—H bond, and an amine or amide, comprising a reactive N—H bond, in the presence of an oxidizing agent and a metal-containing catalyst, thereby forming a product with a covalent bond between the carbon of the reactive C—H bond and the nitrogen of the reactive N—H bond.

In certain embodiments, the present invention relates to any of the aforementioned methods and attendant definitions, wherein the substrate comprising a reactive C—H bond is represented by:

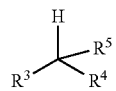

wherein, R$^3$ is alkyl, alkenyl, alkynyl, aryl, heteroaryl, aralkyl, heteroaralkyl, carbocycyl, heterocycyl, polycycyl, carbonyl, ester or ether; R$^4$ is hydrogen, alkyl, alkenyl, alkynyl, aryl, heteroaryl, aralkyl, heteroaralkyl, carbocycyl, heterocycyl, polycycyl, carbonyl, ester or ether; or R$^3$ and R$^4$ taken together are oxo; R$^5$ is hydrogen, alkyl, alkenyl, alkynyl, aryl, heteroaryl, aralkyl, heteroaralkyl, carbocycyl, heterocycyl, polycycyl, carbonyl, ester or ether; and the substrate is optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

In certain embodiments, the present invention relates to any of the aforementioned methods and attendant definitions, wherein R$^3$ is alkenyl.

In certain embodiments, the present invention relates to any of the aforementioned methods and attendant definitions, wherein R$^3$ is aryl or heteroaryl.

In certain embodiments, the present invention relates to any of the aforementioned methods and attendant definitions, wherein R$^4$ is hydrogen.

In certain embodiments, R$^3$ and R$^4$ taken together are oxo.

In certain embodiments, the present invention relates to any of the aforementioned methods and attendant definitions, wherein R$^5$ is hydrogen.

In certain embodiments, the present invention relates to any of the aforementioned methods and attendant definitions, wherein the substrate is carbocylic, heterocyclic, or polycyclic compound.

In certain embodiments, the present invention relates to any of the aforementioned methods and attendant definitions, wherein the substrate is a cyclopropane, cyclobutane, cyclopentane, cyclohexane, indane, 2-oxoindane, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactone, lactam, azetidinone, pyrrolidinone, sultam, or sultone; and the substrate is optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

In certain embodiments, the present invention relates to any of the aforementioned methods and attendant definitions, wherein the substrate is selected from the group consisting of

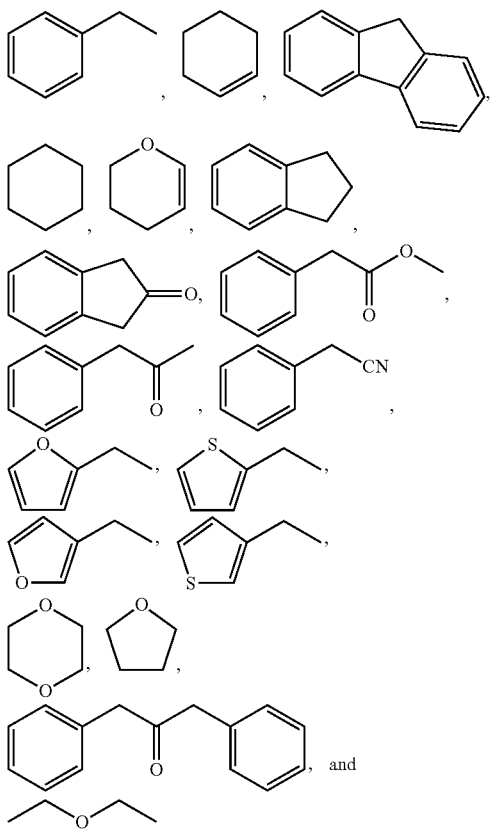

In certain embodiments, the present invention relates to any of the aforementioned methods and attendant definitions, wherein the amine or amide is represented by:

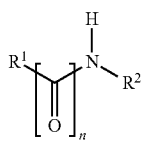

wherein, $R^1$ is hydrogen, alkyl, alkenyl, alkynyl, aryl, heteroaryl, aralkyl or heteroaralkyl; $R^2$ is hydrogen, alkyl, alkenyl, alkynyl, aryl, heteroaryl, aralkyl or heteroaralkyl; or $R^1$ and $R^2$ taken together with the atoms to which they are bound, form a five, six or seven membered ring which contains 0-2 heteroatoms and is optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano; and n is 0 or 1.

In certain embodiments, the present invention relates to any of the aforementioned methods and attendant definitions, wherein $R^1$ is hydrogen, alkyl, alkenyl, alkynyl, aryl, heteroaryl, aralkyl or heteroaralkyl; and $R^2$ is hydrogen, alkyl, alkenyl, alkynyl, aryl, heteroaryl, aralkyl or heteroaralkyl.

In certain embodiments, the present invention relates to any of the aforementioned methods and attendant definitions, wherein $R^1$ is alkyl, aryl, heteroaryl or aralkyl.

In certain embodiments, the present invention relates to any of the aforementioned methods and attendant definitions, wherein $R^2$ is alkyl, aryl, heteroaryl or aralkyl.

In certain embodiments, the present invention relates to any of the aforementioned methods and attendant definitions, wherein $R^1$ and $R^2$ taken together with the atoms to which they are bound, form a five, six or seven membered ring which contains 0-2 heteroatoms.

In certain embodiments, the present invention relates to any of the aforementioned methods and attendant definitions, wherein $R^1$ and $R^2$ taken together form a nitrogen-containing heterocycle.

In certain embodiments, the present invention relates to any of the aforementioned methods and attendant definitions, wherein n is 0.

In certain embodiments, the present invention relates to any of the aforementioned methods and attendant definitions, wherein n is 1.

In certain embodiments, the present invention relates to any of the aforementioned methods and attendant definitions, wherein the amine or amide is selected from the group consisting of

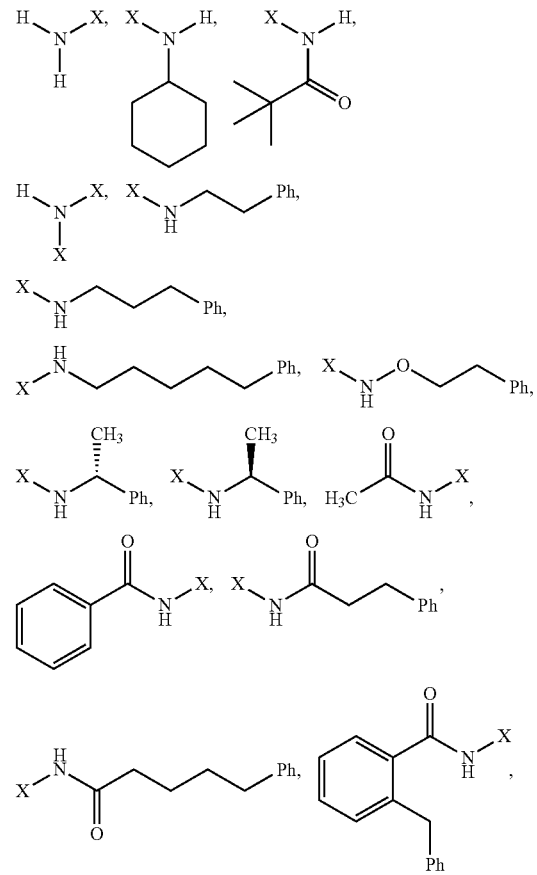

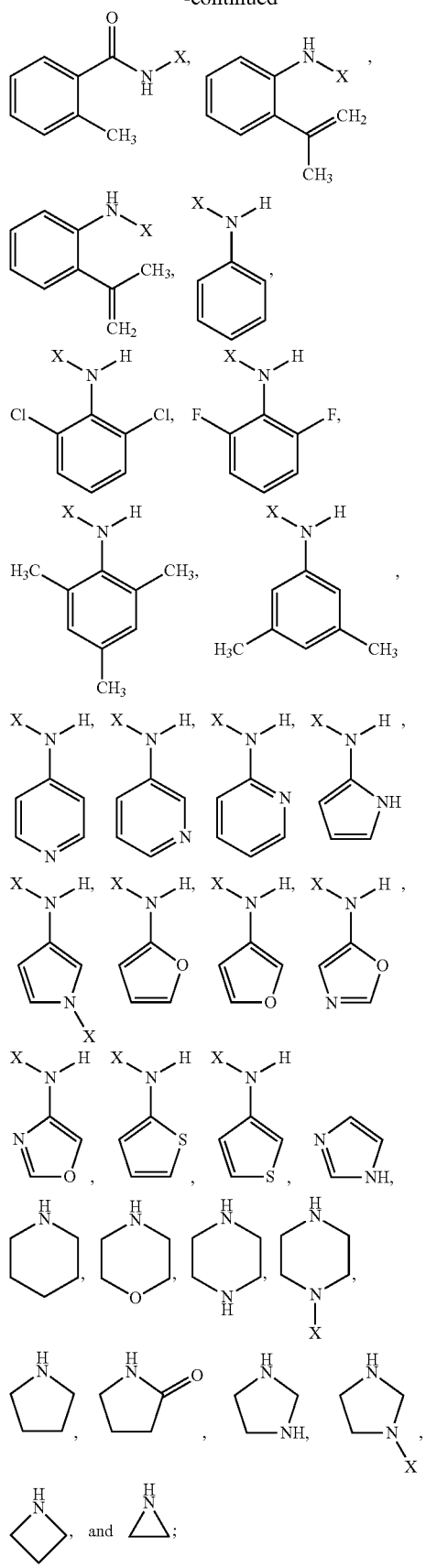

wherein X is hydrogen, alkyl, fluoroalkyl, aryl, aralkyl, heteroaryl, heteroaralkyl, silyl, carbonyl, ester, thioester, sulfonyl, sulfonate, or amide.

In certain embodiments, the present invention relates to any of the aforementioned methods and attendant definitions, wherein the amine or amide is part of the substrate, thereby resulting in a cyclic product.

In certain embodiments, the present invention relates to any of the aforementioned methods and attendant definitions, wherein the oxidant is selected from the group consisting of peroxides, oxygen, halogens, pseudo-halogen compounds, hypervalent iodide compounds, benzoquinones, and inorganic oxidation couples In certain embodiments, the present invention relates to any of the aforementioned methods and attendant definitions, wherein the oxidizing agent is a peroxide represented by:

$$R^6-O-O-R^6$$

wherein, $R^6$ is hydrogen, alkyl, alkenyl, alkynyl, aryl, heteroaryl, aralkyl or heteroaralkyl.

In certain embodiments, the present invention relates to any of the aforementioned methods and attendant definitions, wherein $R^6$ is alkyl.

In certain embodiments, the present invention relates to any of the aforementioned methods and attendant definitions, wherein $R^6$ is tert-butyl.

In certain embodiments, the present invention relates to any of the aforementioned methods and attendant definitions, wherein the metal-containing catalyst is a transition metal-containing catalyst.

In certain embodiments, the present invention relates to any of the aforementioned methods and attendant definitions, wherein the transition metal is Cu, Ag, Au, Pd, Co and Rh.

In certain embodiments, the present invention relates to any of the aforementioned methods and attendant definitions, wherein the transition metal is Cu(I) or Cu(II).

In certain embodiments, the present invention relates to any of the aforementioned methods and attendant definitions, wherein the transition metal is Ag(I).

In certain embodiments, the present invention relates to any of the aforementioned methods and attendant definitions, wherein the metal-containing catalyst is represented by Formula I or its enantiomer:

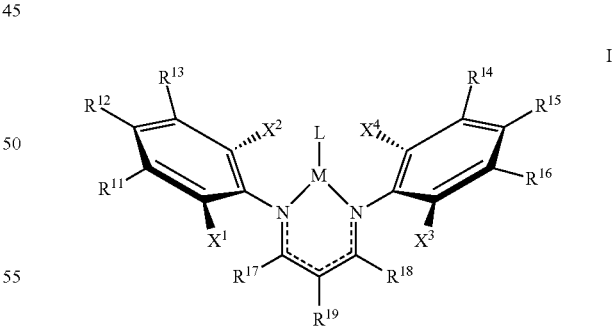

wherein, $R^{11}$ to $R^{19}$ are independently selected from the group consisting of hydrogen, alkyl, aryl, aralkyl, halogen, cyano, nitro, and trifluoromethyl; $X^1$ to $X^4$ are independently selected from the group consisting of hydrogen, halogen or perhaloalkyl; L is absent or a Lewis base; and M is a transition metal.

In certain embodiments, the present invention relates to any of the aforementioned methods and attendant definitions, wherein M is copper.

In certain embodiments, the present invention relates to any of the aforementioned methods and attendant definitions, wherein $R^{17}$-$R^{19}$ represents independently for each occurrence hydrogen, methyl, trifluoromethyl, phenyl, or t-butyl.

In certain embodiments, the present invention relates to any of the aforementioned methods and attendant definitions, wherein $R^{17}$ and $R^{18}$ represent t-butyl.

In certain embodiments, the present invention relates to any of the aforementioned methods and attendant definitions, wherein $R^{17}$ and $R^{18}$ represent trifluoromethyl.

In certain embodiments, the present invention relates to any of the aforementioned methods and attendant definitions, wherein $R^{19}$ is hydrogen.

In certain embodiments, the present invention relates to any of the aforementioned methods and attendant definitions, wherein $X^1$-$X^4$ are independently for each occurrence halogen or perfluoroalkyl.

In certain embodiments, the present invention relates to any of the aforementioned methods and attendant definitions, wherein $X^1$-$X^4$ are independently for each occurrence Cl, I, Br, or $CF_3$.

In certain embodiments, the present invention relates to any of the aforementioned methods and attendant definitions, wherein $X^1$-$X^4$ are Cl.

In certain embodiments, the present invention relates to any of the aforementioned methods and attendant definitions, wherein $X^1$-$X^4$ are $CF_3$.

In certain embodiments, the present invention relates to any of the aforementioned methods and attendant definitions, wherein L is absent.

In certain embodiments, the present invention relates to any of the aforementioned methods and attendant definitions, wherein L is solvent.

In certain embodiments, the present invention relates to any of the aforementioned methods and attendant definitions, wherein L is aromatic.

In certain embodiments, the present invention relates to any of the aforementioned methods and attendant definitions, wherein L is an olefin.

In certain embodiments, the present invention relates to any of the aforementioned methods and attendant definitions, wherein L is benzene.

In certain embodiments, the present invention relates to any of the aforementioned methods and attendant definitions, wherein the catalyst is selected from the group consisting of

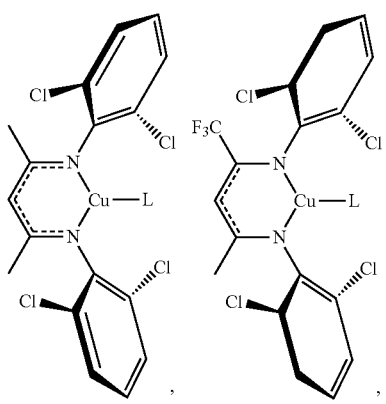

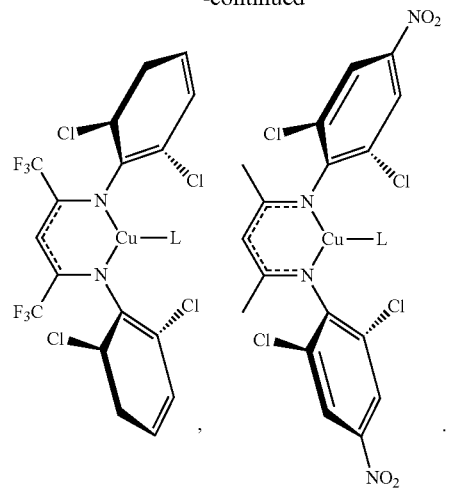

In certain embodiments, the present invention relates to any of the aforementioned methods and attendant definitions, wherein the metal-containing catalyst is represented by Formula IIa or its enantiomer:

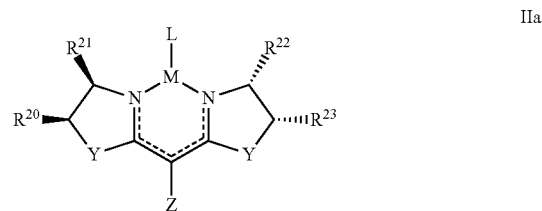

wherein, $R^{20}$ is hydrogen, alkyl, aryl or heteroaryl; $R^{21}$ is alkyl, aryl or heteroaryl; $R^{22}$ is hydrogen, alkyl, aryl or heteroaryl; $R^{23}$ is alkyl, aryl or heteroaryl; Y is O, S, $CH_2$ or $CH_2CH_2$; Z is hydrogen or cyano; L is absent or a Lewis base; and M is a transition metal.

In certain embodiments, the present invention relates to any of the aforementioned methods and attendant definitions, wherein $R^{20}$ is hydrogen.

In certain embodiments, the present invention relates to any of the aforementioned methods and attendant definitions, wherein $R^{20}$ is phenyl.

In certain embodiments, the present invention relates to any of the aforementioned methods and attendant definitions, wherein $R^{21}$ is phenyl.

In certain embodiments, the present invention relates to any of the aforementioned methods and attendant definitions, wherein $R^{22}$ is phenyl.

In certain embodiments, the present invention relates to any of the aforementioned methods and attendant definitions, wherein $R^{23}$ is hydrogen.

In certain embodiments, the present invention relates to any of the aforementioned methods and attendant definitions, wherein $R^{23}$ is phenyl.

In certain embodiments, the present invention relates to any of the aforementioned methods and attendant definitions, wherein Y is O.

In certain embodiments, the present invention relates to any of the aforementioned methods and attendant definitions, wherein Z is hydrogen.

In certain embodiments, the present invention relates to any of the aforementioned methods and attendant definitions, wherein Z is cyano.

In certain embodiments, the present invention relates to any of the aforementioned methods and attendant definitions, wherein M is copper.

In certain embodiments, the present invention relates to any of the aforementioned methods and attendant definitions, wherein L is absent.

In certain embodiments, the present invention relates to any of the aforementioned methods and attendant definitions, wherein L is solvent.

In certain embodiments, the present invention relates to any of the aforementioned methods and attendant definitions, wherein L is aromatic.

In certain embodiments, the present invention relates to any of the aforementioned methods and attendant definitions, wherein L is an olefin.

In certain embodiments, the present invention relates to any of the aforementioned methods and attendant definitions, wherein L is benzene.

In certain embodiments, the present invention relates to any of the aforementioned methods and attendant definitions, wherein the catalyst is selected from the group consisting of In certain embodiments, the present invention relates to any of the aforementioned methods and attendant definitions, wherein L is absent.

In certain embodiments, the present invention relates to any of the aforementioned methods and attendant definitions, wherein L is solvent.

In certain embodiments, the present invention relates to any of the aforementioned methods and attendant definitions, wherein L is aromatic.

In certain embodiments, the present invention relates to any of the aforementioned methods and attendant definitions, wherein L is an olefin.

In certain embodiments, the present invention relates to any of the aforementioned methods and attendant definitions, wherein L is alkyoxy.

In certain embodiments, the present invention relates to any of the aforementioned methods and attendant definitions, wherein L is —OtBu.

In certain embodiments, the present invention relates to any of the aforementioned methods and attendant definitions, wherein the metal-containing catalyst is

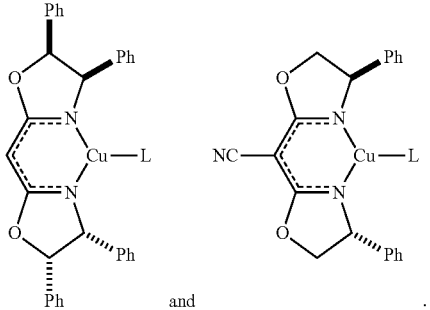

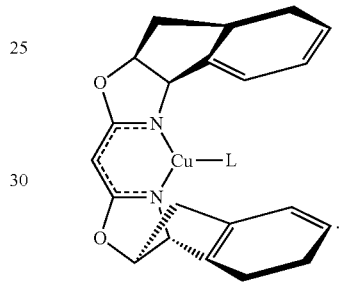

In certain embodiments, the present invention relates to any of the aforementioned methods and attendant definitions, wherein the metal-containing catalyst is represented by Formula IIb or its enantiomer:

In certain embodiments, the present invention relates to any of the aforementioned methods and attendant definitions, wherein the metal-containing catalyst is represented by Formula III or its enantiomer:

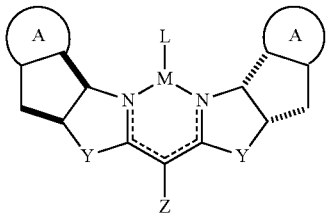

IIb

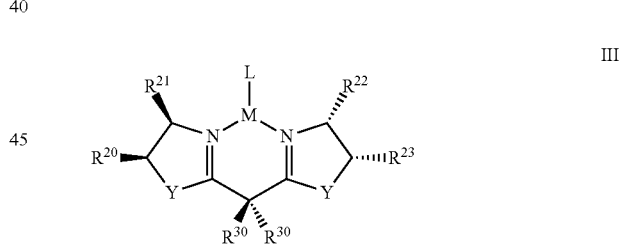

III wherein, A is aryl or heteroaryl; Y is O, S, $CH_2$ or $CH_2CH_2$; Z is hydrogen or cyano; L is absent or a Lewis base; and M is a transition metal.

In certain embodiments, the present invention relates to any of the aforementioned methods and attendant definitions, wherein A is phenyl.

In certain embodiments, the present invention relates to any of the aforementioned methods and attendant definitions, wherein Y is O.

In certain embodiments, the present invention relates to any of the aforementioned methods and attendant definitions, wherein Z is hydrogen.

In certain embodiments, the present invention relates to any of the aforementioned methods and attendant definitions, wherein M is copper.

wherein, $R^{20}$ is hydrogen, alkyl, aryl or heteroaryl; $R^{21}$ is alkyl, aryl or heteroaryl; $R^{22}$ is hydrogen, alkyl, aryl or heteroaryl; $R^{23}$ is alkyl, aryl or heteroaryl; $R^{30}$ is alkyl or both $R^{30}$ taken together are cycloalkyl; Y is O, S, $CH_2$ or $CH_2CH_2$; L is a Lewis base; and M is a transition metal.

In certain embodiments, the present invention relates to any of the aforementioned methods and attendant definitions, wherein $R^{20}$ is hydrogen.

In certain embodiments, the present invention relates to any of the aforementioned methods and attendant definitions, wherein $R^{21}$ is phenyl.

In certain embodiments, the present invention relates to any of the aforementioned methods and attendant definitions, wherein $R^{21}$ is t-butyl.

In certain embodiments, the present invention relates to any of the aforementioned methods and attendant definitions, wherein $R^{22}$ is phenyl.

In certain embodiments, the present invention relates to any of the aforementioned methods and attendant definitions, wherein $R^{22}$ is t-butyl.

In certain embodiments, the present invention relates to any of the aforementioned methods and attendant definitions, wherein $R^{23}$ is hydrogen.

In certain embodiments, the present invention relates to any of the aforementioned methods and attendant definitions, wherein $R^{30}$ is alkyl.

In certain embodiments, the present invention relates to any of the aforementioned methods and attendant definitions, wherein $R^{30}$ is methyl.

In certain embodiments, the present invention relates to any of the aforementioned methods and attendant definitions, wherein Y is O.

In certain embodiments, the present invention relates to any of the aforementioned methods and attendant definitions, wherein M is copper.

In certain embodiments, the present invention relates to any of the aforementioned methods and attendant definitions, wherein L is absent.

In certain embodiments, the present invention relates to any of the aforementioned methods and attendant definitions, wherein L is solvent.

In certain embodiments, the present invention relates to any of the aforementioned methods and attendant definitions, wherein L is aromatic.

In certain embodiments, the present invention relates to any of the aforementioned methods and attendant definitions, wherein L is an olefin.

In certain embodiments, the present invention relates to any of the aforementioned methods and attendant definitions, wherein L is NC(alkyl).

In certain embodiments, the present invention relates to any of the aforementioned methods and attendant definitions, wherein L is NC(methyl).

In certain embodiments, the present invention relates to any of the aforementioned methods and attendant definitions, wherein the catalyst is selected from the group consisting of

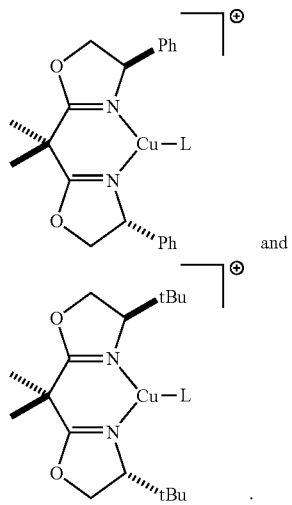

In certain embodiments, the present invention relates to any of the aforementioned methods and attendant definitions, wherein the metal-containing catalyst is represented by Formula IV:

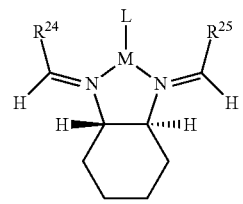

wherein $R^{24}$ is aryl or heteroaryl; $R^{25}$ is aryl or heteroaryl; L is a Lewis base; and M is a transition metal.

In certain embodiments, the present invention relates to any of the aforementioned methods and attendant definitions, wherein $R^{24}$ is phenyl optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

In certain embodiments, the present invention relates to any of the aforementioned methods and attendant definitions, wherein $R^{24}$ is a 2,6-disubstituted phenyl; and the substituents are selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

In certain embodiments, the present invention relates to any of the aforementioned methods and attendant definitions, wherein $R^{24}$ is a 2,6-dihalo phenyl.

In certain embodiments, the present invention relates to any of the aforementioned methods and attendant definitions, wherein $R^{25}$ is phenyl optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

In certain embodiments, the present invention relates to any of the aforementioned methods and attendant definitions, wherein $R^{25}$ is a 2,6-disubstituted phenyl; and the substituents are selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

In certain embodiments, the present invention relates to any of the aforementioned methods and attendant definitions, wherein $R^{25}$ is a 2,6-dihalo phenyl.

In certain embodiments, the present invention relates to any of the aforementioned methods and attendant definitions, wherein M is copper.

In certain embodiments, the present invention relates to any of the aforementioned methods and attendant definitions, wherein L is absent.

In certain embodiments, the present invention relates to any of the aforementioned methods and attendant definitions, wherein L is solvent.

In certain embodiments, the present invention relates to any of the aforementioned methods and attendant definitions, wherein L is aromatic.

In certain embodiments, the present invention relates to any of the aforementioned methods and attendant definitions, wherein L is an olefin.

In certain embodiments, the present invention relates to any of the aforementioned methods and attendant definitions, wherein L is NC(alkyl).

In certain embodiments, the present invention relates to any of the aforementioned methods and attendant definitions, wherein L is NC(methyl).

In certain embodiments, the present invention relates to any of the aforementioned methods and attendant definitions, wherein the catalyst is

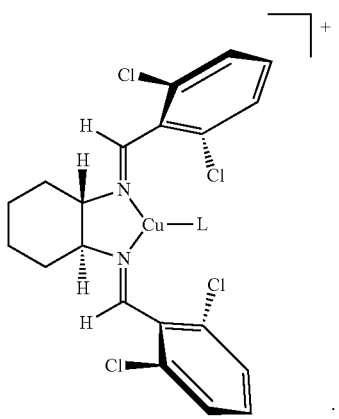

In certain embodiments, the present invention relates to any of the aforementioned methods and attendant definitions, wherein the product is a polyamine.

In certain embodiments, the present invention relates to any of the aforementioned methods and attendant definitions, wherein the reaction is run in neat substrate.

In certain embodiments, the present invention relates to any of the aforementioned methods and attendant definitions, wherein the reaction takes place in a solvent.

In certain embodiments, the present invention relates to any of the aforementioned methods and attendant definitions, wherein the solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol and propyl acetate In certain embodiments, the present invention relates to any of the aforementioned methods and attendant definitions, wherein the solvent is anisole.

In certain embodiments, the present invention relates to any of the aforementioned methods and attendant definitions, wherein the reaction is run at a temperature between about 50° C. and about 100° C.

In certain embodiments, the present invention relates to any of the aforementioned methods and attendant definitions, wherein the reaction is run at a temperature of about 80° C.

Catalyst Loading. A wide range of catalyst loadings can be used for the amination reactions described herein. In certain embodiments, the catalyst is present in less than about 70 mol % relative to the substrate. In certain embodiments, the catalyst is present in less than about 40 mol % relative to the substrate. In certain embodiments, the catalyst is present in less than about 20 mol % relative to the substrate. In certain embodiments, the catalyst is present in less than about 10 mol % relative to the substrate. In certain embodiments, the catalyst is present in less than about 5 mol % relative to the substrate. In certain embodiments, the catalyst is present in less than about 2.5 mol % relative to the substrate. In certain embodiments, the catalyst is present in less than about 1 mol % relative to the substrate.

Yields. In certain embodiments, the present invention relates to any of the aforementioned methods and attendant definitions, wherein the product is formed in a yield of at least about 10%. In certain embodiments, the present invention relates to any of the aforementioned methods and attendant definitions, wherein the product is formed in a yield of at least about 20%. In certain embodiments, the present invention relates to any of the aforementioned methods and attendant definitions, wherein the product is formed in a yield of at least about 30%. In certain embodiments, the present invention relates to any of the aforementioned methods and attendant definitions, wherein the product is formed in a yield of at least about 40%. In certain embodiments, the present invention relates to any of the aforementioned methods and attendant definitions, wherein the product is formed in a yield of at least about 50%. In certain embodiments, the present invention relates to any of the aforementioned methods and attendant definitions, wherein the product is formed in a yield of at least about 60%. In certain embodiments, the present invention relates to any of the aforementioned methods and attendant definitions, wherein the product is formed in a yield of at least about 70%. In certain embodiments, the present invention relates to any of the aforementioned methods and attendant definitions, wherein the product is formed in a yield of at least about 80%. In certain embodiments, the present invention relates to any of the aforementioned methods and attendant definitions, wherein the product is formed in a yield of at least about 90%. In certain embodiments, the present invention relates to any of the aforementioned methods and attendant definitions, wherein the product is formed in a yield of at least about 95%.

VII. REACTION CONDITIONS

The amination reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely effect the substrate, the amine, the catalyst, or the product. For example, the reaction temperature influences the speed of the reaction, as well as the stability of the reactants, products, and catalyst. The reactions will usually be run at temperatures in the range of about −78° C. to about 200° C., in the range about 0° C. to about 100° C., or in the range about 50° C. to about 100° C.

In general, the amination reactions of the present invention are carried out in a liquid reaction medium. The reactions may be run without addition of solvent. Alternatively, the reactions may be run in an inert solvent, preferably one in which the reaction ingredients, including the catalyst, are substantially soluble. In some embodiments, the reactions can be run in a combinations of two or more solvents.

The most environmentally friendly process will use little or no solvent as process conditions allow. It is possible to run the reaction in some cases without any solvent (e.g., morpholine, t-butylperoxide, ethylbenzene). In these cases, the reaction components form a liquid mixture at or above room temperature. (Caution—lack of reaction solvent may cause an exotherm when catalyst is added to mixture.)

In certain embodiments, the substrate itself may be used as a solvent. For instance, high yields of ethylbenzene amination have been demonstrated using ethylbenzene as a solvent. Separation of the product from solvent is facilitated by the significant difference in chemical properties of the substrate/solvent as compared to the aminated product.

An ideal solvent for the process does not undergo any reaction during the catalytic process except possibly weak, reversible binding to copper catalyst. Solvents that do not have C—H bonds on the strength of benzyl and allylic C—H bonds (e.g., 88 kcal/mol and lower) may be appropriate for the amination reaction. For instance, benzene (C—H bond strength=112.9 kcal/mol) is an appropriate solvent.

Provided that there is a suitable difference in the strength and kinetic availability of the substrate C—H bond for functionalization, linear hydrocarbons such as hexane and heptane may prove useful solvents. More polar solvents such as ethers may be employed.

Ideally, the process employs one of the Class 3 solvents representing the least toxicity and environmental impact. Class 3 solvents include acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol and propyl acetate. Of these, anisole is particularly promising. It has a C—H bond strength ($OCH_3$) of 11 kcal/mol greater than ethylbenzene. With a boiling point of 154° C., it is not particularly volatile. Separations of amine products are straightforward from solvent. Other promising solvents include tert-butylmethyl ether (MTBE), ethyl acetate, ethyl ether, heptane, methyl acetate, methyl ethyl ketone, pentane, and propyl acetate. All of these solvents possess C—H bonds whose weakest C—H bond strengths are about 8-10 kcal/mol higher than a benzylic or allylic C—H bond targeted in this C—H amination reaction.

The invention also contemplates reaction in a biphasic mixture of solvents, in an emulsion or suspension, or reaction in a lipid vesicle or bilayer. In certain embodiments, it may be preferred to perform the amination reactions in the solid phase.

In certain embodiments it is preferable to perform the reactions under an inert atmosphere of a gas such as nitrogen or argon.

The methods of the present invention can be conducted in continuous, semi-continuous or batch fashion and may involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal-ligand complex catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the catalyst can be immobilized or incorporated into a polymer or other insoluble matrix by, for example, derivativation with one or more of substituents of the ligand. The immobilized ligands can be complexed with the desired metal to form the catalyst. The catalyst, particularly an "aged" catalyst, is easily recovered after the reaction as, for instance, by filtration or centrifugation.

In addition, since formal reductive elimination of the oxidized takes place within the coordination sphere of a single metal center, control over enantioselectivity may be levied with the selection of appropriate chiral ligands.

VIII. SELECTED INDUSTRIAL APPLICATIONS

The amination reactions described herein have commercial potential. For example, it is believed that no other system allows for "normal" organic amines in C—H amination—amines with protecting groups must be utilized along with more expensive oxidants. The use of "throw-away" protecting groups and expensive oxidants which currently represents the state-of-the art for C—H amination significantly impacts the cost and environmental impact of C—H amination.

In addition, a tremendous range of amines are commercially available and amenable to this technology, whereas only a few such azides are commercially available—they need to be prepared as intermediates.

Further, the direct use of amines removes a step from the overall synthesis. The process is thus less expensive and more environmentally friendly, especially with thee of hydrogen peroxide in optimized systems.

Importantly, the disclosed methods also substantially reduce the hazards associated with the amination process, especially upon scale up. Many industrial users are unwilling to use azides, which require special production facilities, though they would be interested in processes directly involving amines or ammonia.

IX. DEFINITIONS

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

For purposes of this invention, the chemical elements are identified in accordance with the Periodic Table of the Elements, CAS version, Handbook of Chemistry and Physics, 67th Ed., 1986-87, inside cover.

A "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The term "reaction product" or "product" means a compound which results from the reaction of the catalyst and substrate. In general, the term "reaction product" will be used herein to refer to a stable, isolable compound, and not to unstable intermediates or transition states.

The term "catalytic amount" is recognized in the art and means a substoichiometric amount relative to a reactant. As used herein, a catalytic amount means from 0.0001 to 90 mole percent relative to a reactant, more preferably from 0.001 to 50 mole percent, still more preferably from 0.01 to 10 mole percent, and even more preferably from 0.1 to 5 mole percent relative to a reactant.

As discussed more fully herein, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% Enantiomeric Excess $A(ee) = $ (% Enantiomer $A$) – (% Enantiomer $B$)

where A and B are the enantiomers formed. Additional terms that are used in conjunction with enatioselectivity include "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantimerically-enriched unreacted substrate. Kinetic resolution is usually achieved by the use of sufficient reagent to react with only one reactant enantiomer (i.e., one-half mole of reagent per mole of racemic substrate). Examples of catalytic reactions which have been used for kinetic resolution of racemic reactants include the Sharpless epoxidation and the Noyori hydrogenation.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

The term "alkyl" refers to the radical of saturated aliphatic groups, including straight-chain alkyl groups (e.g., methyl, ethyl, propyl, butyl, pentyl, hexyl, heptyl, octyl), branched-chain alkyl groups (e.g., i-propyl, i-butyl, t-butyl), cycloalkyl (alicyclic) groups (e.g., cyclopropyl, cyclobutyl, cyclopentyl, cyclohexyl), alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 of fewer. Likewise, preferred cycloalkyls have from 4-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aryl or heteroaryl group).

The terms "alkenyl" and "alkynyl" refer to unsaturated aliphatic groups analogous in length and possible substitution to the alkyls described above, but which contain at least one double or triple carbon-carbon bond, respectively.

The term "Me$_2$NN" refers to a moiety represented by the general formula:

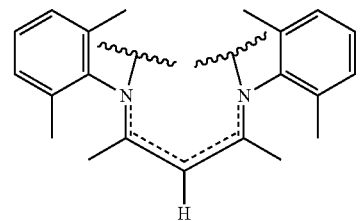

The term "Cl$_2$NN" refers to a moiety represented by the general formula:

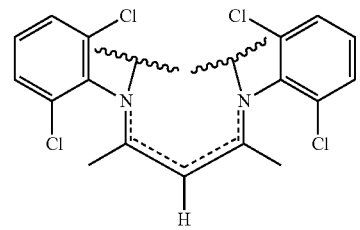

The term "halogen" designates —F, —Cl, —Br or —I; the term "thiol" means —SH; the term "hydroxyl" means —OH;

and the term "organometallic" refers to a metallic atom (such as mercury, zinc, lead, magnesium or lithium) or a metalloid (such as silicon, arsenic or selenium) which is bonded directly to a carbon atom, such as a diphenylmethylsilyl group.

The terms "amine" and "amino" are art-recognized and refer to both unsubstituted and substituted amines, e.g., a moiety that can be represented by the general formula:

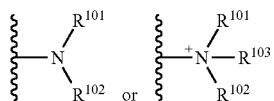

wherein $R^{101}$, $R^{102}$ and $R^{103}$ each independently represent hydrogen, alkyl, alkenyl, alkynyl, aryl, heteroaryl, —$(CH_2)_m$—$R^{200}$, wherein m is 1-10 and $R^{200}$ represents a group permitted by the rules of valence, such as hydrogen, alkyl, alkenyl, alkynyl, aryl, and heteroaryl.

The term "amino" also includes "acylamino," which is art-recognized and refers to a moiety that can be represented by the general formula:

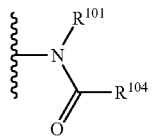

wherein $R^{101}$ is as defined above, and $R^{104}$ represents hydrogen, alkyl, alkenyl, alkynyl, aryl, heteroaryl or —$(CH_2)_m$—$R^{200}$, wherein m and $R^{200}$ are defined above.

The term "amido" is art-recognized as an amino-substituted carbonyl and includes a moiety that can be represented by the general formula:

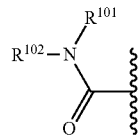

wherein $R^{101}$ and $R^{102}$ are as defined above. Preferred embodiments of the amide will not include those which are unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R^{200}$, wherein m and $R^{200}$ are defined above. Representative alkylthio groups include methylthio and ethylthio.

The term "carbonyl" is art-recognized and includes such moieties as can be represented by the general formula:

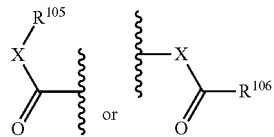

wherein X is a bond or represents an oxygen or a sulfur, and $R^{105}$ represents a hydrogen, alkyl, alkenyl, alkynyl, aryl, heteroaryl or —$(CH_2)_m R^{200}$, wherein m is 1-10 and $R^{200}$ are defined above, or a pharmaceutically acceptable salt, and $R^{106}$ represents hydrogen, alkyl, alkenyl, alkynyl, aryl, heteroaryl or —$(CH_2)_m R^{200}$, wherein m and $R^{200}$ are defined above. Where X is an oxygen and $R^{105}$ or $R^{106}$ is not hydrogen, the formula represents an "ester". Where X is an oxygen, and $R^{105}$ is as defined above, the moiety is referred to herein as a carboxyl group, and particularly when $R^{105}$ is a hydrogen, the formula represents a "carboxylic acid". Where X is an oxygen, and $R^{106}$ is hydrogen, the formula represents a "formate". In general, where the oxygen atom of the above formula is replaced by sulfur, the formula represents a "thiolcarbonyl" group. Where X is a sulfur and $R^{105}$ or $R^{106}$ is not hydrogen, the formula represents a "thiolester." Where X is a sulfur and $R^{105}$ is hydrogen, the formula represents a "thiolcarboxylic acid." Where X is a sulfur and $R^{106}$ is hydrogen, the formula represents a "thiolformate." On the other hand, where X is a bond, and $R^{105}$ is not hydrogen, the above formula represents a "ketone" group. Where X is a bond, and $R^{106}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, t-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —$(CH_2)_m$—$R^{200}$, where m and $R^{200}$ are as defined above.

The term "sulfonate" is art-recognized and includes a moiety that can be represented by the general formula:

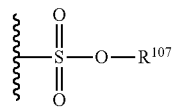

in which $R^{107}$ is an electron pair, hydrogen, alkyl, alkenyl, alkynyl, aryl, heteroaryl or —$(CH_2)_m R^{200}$, wherein m and $R^{200}$ are defined above.

The term "sulfonylamino" is art-recognized and includes a moiety that can be represented by the general formula:

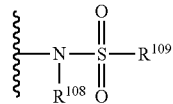

in which $R^{108}$ and $R^{109}$ independently represents hydrogen, alkyl, alkenyl, alkynyl, aryl, heteroaryl or —$(CH_2)_m R^{200}$, wherein m and $R^{200}$ are defined above.

The term "sulfamoyl" is art-recognized and includes a moiety that can be represented by the general formula:

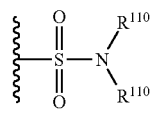

wherein $R^{110}$ independently for each occurrence represents hydrogen, alkyl, alkenyl, alkynyl, aryl, heteroaryl or —$(CH_2)_m R^{200}$, wherein m and $R^{200}$ are defined above.

The term "sulfonyl", as used herein, refers to a moiety that can be represented by the general formula:

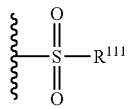

wherein $R^{111}$ represents hydrogen, alkyl, alkenyl, alkynyl, aryl, heteroaryl or —$(CH_2)_m R^{200}$, wherein m and $R^{200}$ are defined above.

The term "sulfoxido" as used herein, refers to a moiety that can be represented by the general formula:

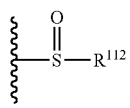

wherein $R^{112}$ represents hydrogen, alkyl, alkenyl, alkynyl, aryl, heteroaryl or —$(CH_2)_m R^{200}$, wherein m and $R^{200}$ are defined above.

The term "aryl" as used herein includes 4-, 5-, 6- and 7-membered single-ring aromatic groups which may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, —$(CH_2)_m$—$R^{200}$, fluoroalkyl, trifluoromethyl, cyano, or the like.

The term "heterocyclyl" or "heterocyclic" refer to 4 to 10-membered ring structures, more preferably 5 to 7 membered rings, which ring structures include one to four heteroatoms (i.e., univalent groups formed by removing a hydrogen atom from any ring atom of a heterocyclic compound). Heterocyclic compounds include thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —$(CH_2)_m$—$R^{200}$ (m and $R^{200}$ as defined above), fluoroalkyl, trifluoromethyl, cyano, or the like.

The term "carbocyclic" is art-recognized and refers to an aromatic or non-aromatic ring in which each atom of the ring is carbon.

The terms "polycyclyl" or "polycyclic" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above for aryl.

The term "heteroatom" as used herein means an atom of any element other than carbon or hydrogen. Preferred heteroatoms are nitrogen, oxygen, sulfur, phosphorus and selenium.

The terms ortho, meta and para apply to 1,2-, 1,3- and 1,4-disubstituted benzenes, respectively. For example, the names 1,2-dimethylbenzene and ortho-dimethylbenzene are synonymous.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

As used herein, a "reactive C—H bond" is a C—H bond which has an adjacent moiety which stabilizes any radical character that develops on the carbon of the C—H bond during the amination reaction. In certain embodiments, the reactive C—H bond may have a lower bond dissociation energy than an average C—H bond (e.g., 438 kJ/mol in methane). In certain embodiments, the reactive C—H bond has an adjacent heteroatom or $sp^2$-hybridized carbon. In other embodiments, the reactive C—H bond has three adjacent alkyl groups (e.g., the C—H is part of a tert-butyl moiety). In yet other embodiments, the reactive C—H bond is an aldehyde C—H bond.

As used herein, a "reactive N—H" bond is a N—H bond on ammonia, a primary amine, a secondary amine, or a N—H bond of an organic amide $RC(O)NH_2$ or $RC(O)NHR'$.

EXEMPLIFICATION

The invention now being generally described, it will be more readily understood by reference to the following examples, which are included merely for purposes of illustration of certain aspects and embodiments of the present invention, and are not intended to limit the invention.

Examples 1-6 related to C—H bond amination with $\{[Cl_2NN]Cu\}_2$(benzene) as a catalyst. Examples 1-4 show the amination reaction using primary amines; and examples 5 and 6 show the amination reaction of secondary amines. Examples 7-9 relate to catalytic C—H bond amination using chiral bis(oxazoline) copper(I) catalysts.

Example 1

Preparation of [Cl₂NN]Cu(benzene)

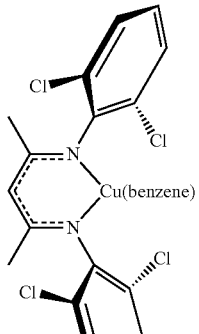

[Cl₂NN]Cu(benzene)

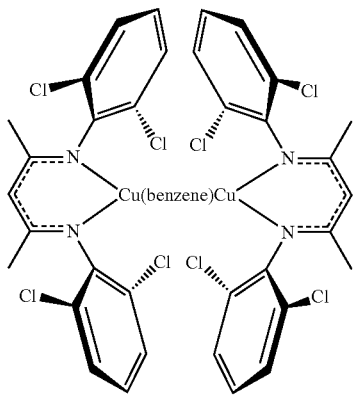

{[Cl₂NN]Cu}₂(benzene)

[Cl₂NN]Cu(benzene) forms when {[Cl₂NN]Cu}₂(benzene) is dissolved in benzene. The arene solvent is labile.

Example 2

Preparation of PhCH(NHMes)Me

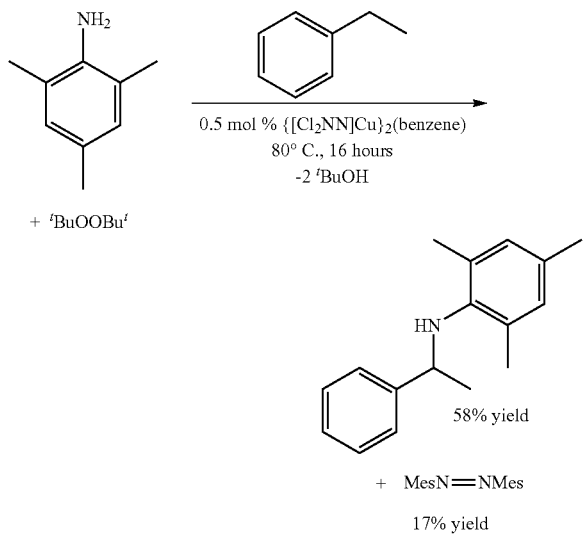

Into a pressure vessel 2,4,6-trimethylaniline (100 mg, 104 μL, 0.741 mmol), tert-butyl peroxide (108 mg, 136 μL, 0.741 mmol), and 1,2,4,5-tetrachlorobenzene (160 mg, 0.741 mmol) was added and diluted to 19 mL with ethylbenzne. To this stirring solution was added 1 mL of a stock solution of {[Cl₂NN]Cu}₂(benzene) in ethylbenzene (0.00371 M, 0.0185 mmol, 18.1 mg diluted to 5 mL with ethylbenzene). The pressure vessel was sealed and heated to 80° C. for 18 hr. The catalyst was separated by exposing the mixture to air and filtering through celite. The solution was analyzed by ¹H NMR and GC/MS to determine the yield and consumption of starting materials. 58% yield (¹H NMR, 1,2,4,5-tetrachlorobenzene standard). ¹H NMR (benzene-d₆): δ 7.105 (m, 7, Ar—H), δ 4.154 (m, 1, $C_{Bz}$—H), δ 2.907 (br, 1, N—H), δ 2.142 (s, 3, Ar-p-CH₃), δ 2.040 (s, 6, Ar-o-CH₃), δ 1.333 (d, 3, CH₃); GC/MS m/z=240 (CI mode, [M]+1).

A byproduct of the reaction is a diazine (MesN=NMes). ¹H NMR (benzene-d₆): δ 6.740 (s, 4, Ar—H), δ 2.462 (s, 12, Ar-o-CH₃), δ 2.117 (s, 6, Ar-p-CH₃); GC/MS m/z=267 (CI mode, [M]+1).

Example 3

Preparation of PhCH(NHAr$^F$)Me (Ar$^F$= 3,5-(CF₃)₂C₆H₃)

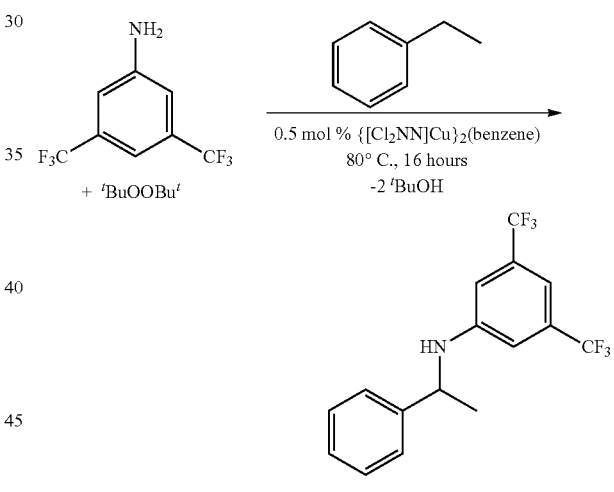

92% yield
sole product

Into a pressure vessel 3,5-bis(trifluoromethyl)aniline (169 mg, 115 μL, 0.741 mmol), tert-butyl peroxide (108 mg, 136 μL, 0.741 mmol), and 1,2,4,5-tetrachlorobenzene (160 mg, 0.741 mmol) was added and diluted to 19 mL with ethylbenzne. To this stirring solution was added 1 mL of a stock solution of {[Cl₂NN]Cu}₂(benzene) in ethylbenzene (0.00371 M, 0.0185 mmol, 18.1 mg diluted to 5 mL with ethylbenzene). The pressure vessel was sealed and heated to 80° C. for 18 hr. The catalyst was separated by exposing the mixture to air and filtering through celite. The solution was analyzed by ¹H NMR and GC/MS to determine the yield and consumption of starting materials. 92% yield (¹H NMR, 1,2,4,5-tetrachlorobenzene standard). ¹H NMR (benzene-d₆): δ 7.027 (m, 8, Ph-H and Ar—H), δ 3.854 (qnt, 1, $C_{Bz}$—H), δ 3.511 (br, 1, N—H), δ 1.002 (d, 3, CH₃); GC/MS m/z=334 (CI mode, [M]+1])

Example 4

Preparation of PhCH(CH$_3$)NHC$_6$H$_2$(2,4-Br, 6-F)

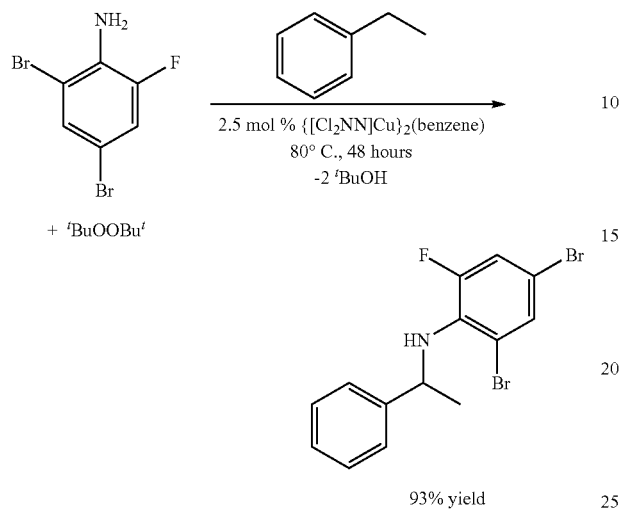

93% yield

Into a pressure vessel 2,4-dibromo-6-fluoroaniline (199 mg, 0.741 mmol), tert-butyl peroxide (108 mg, 136 μL, 0.741 mmol), and 1,2,4,5-tetrachlorobenzene (160 mg, 0.741 mmol) was added and diluted to 19 mL with ethylbenzne. To this stirring solution was added 1 mL of a stock solution of {[Cl$_2$NN]Cu}$_2$(benzene) in ethylbenzene (0.00371 M, 0.0185 mmol, 18.1 mg diluted to 5 mL with ethylbenzene). The pressure vessel was sealed and heated to 80° C. for 48 hr. The catalyst was separated by exposing the mixture to air and filtering through Celite. After removing ethylbenzene under vacuum, the solution was analyzed by $^1$H NMR and GC/MS to determine the yield and consumption of starting materials. Isolated yield: 93% (90% pure by $^1$H NMR). $^1$H NMR (CDCl$_3$): δ 7.25 (m, 5, Ph-H), δ 7.17 (t, 1, Ar—H), δ 6.96 (d, 1, Ar—H), δ 4.90 (qnt, 1, C$_{Bz}$—H), δ 4.27 (d, 1, N—H), δ 1.51 (d, 3, CH$_3$); GC/MS m/z=373.8 (CI mode).

Example 5

Preparation of PhCH(CH$_3$)NMePh

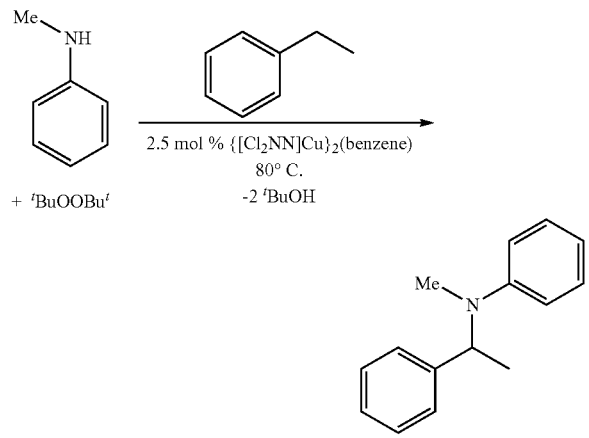

Into a pressure vessel HNMePh (79.4 mg, 80 μL, 0.741 mmol), tert-butyl peroxide (108 mg, 136 μL, 0.741 mmol), and 1,2,4,5-tetrachlorobenzene (160 mg, 0.741 mmol) was added and diluted to 19 mL with ethylbenzne To this stirring solution was added 1 mL of a stock solution of {[Cl$_2$NN]Cu}$_2$(benzene) in ethylbenzene (0.00371 M, 0.0185 mmol, 18.1 mg diluted to 5 mL with ethylbenzene). The pressure vessel was sealed and heated to 80° C. for 48 hr. The catalyst was separated by exposing the mixture to air and filtering through celite. The solution was analyzed by GC/MS to determine the consumption of the amine. After 24 hours, 89% conversion and after 48 hours, 99% conversion was obtained (GC/MS-EI mode, 1,2,4,5-tetrachlorobenzene standard). Major product (PhCH(CH$_3$)NMePh) GC/MS m/z=211.9 (CI mode). Minor Product (ca. 5%) (PhC(CH$_3$)(NMePh)$_2$) GC/MS m/z=316.0 (CI mode).

Example 6

Preparation of PhCH(CH$_3$)NC$_4$H$_8$O

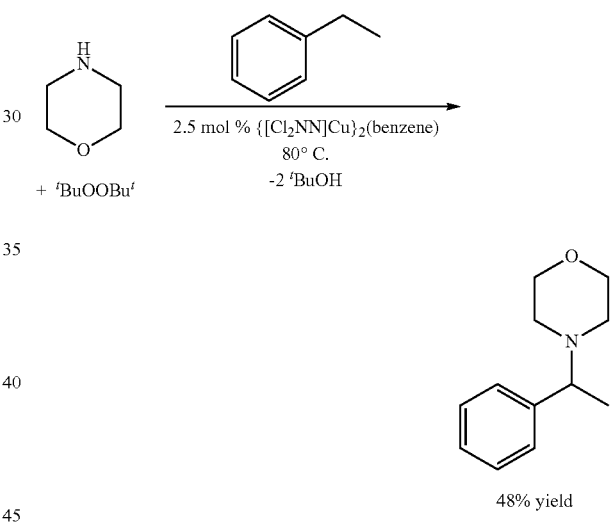

48% yield

Into a pressure vessel morpholine (64.5 mg, 65 μL, 0.741 mmol), tert-butyl peroxide (108 mg, 136 μL, 0.741 mmol), and 1,2,4,5-tetrachlorobenzene (160 mg, 0.741 mmol) was added and diluted to 19 mL with ethylbenzne To this stirring solution was added 1 mL of a stock solution of {[Cl$_2$NN]Cu}$_2$(benzene) in ethylbenzene (0.00371 M, 0.0185 mmol, 18.1 mg diluted to 5 mL with ethylbenzene). The pressure vessel was sealed and heated to 80° C. for 20 hr. The catalyst was separated by exposing the mixture to air and filtering through celite. Ethylbenzene was removed under vacuum and the resulting oil was analyzed by $^1$H NMR to estimate the yield. 48% yield ($^1$H NMR, 1,2,4,5-tetrachlorobenzene standard). $^1$H NMR (CDCl$_3$): δ 7.25 (m, 5, Ph-H), δ 3.67 (t, 4, morpholine OC—H), δ 3.28 (qrt, 1, C$_{Bz}$—H), δ 1.33 (d, 1, CH$_3$) δ 0.91 (t, 4, morpholine NC—H); GC/MS m/z=191.9 (CI mode). No other C—H functionalized product was observed by GC/MS.

Example 7

Preparation of PhCH(NHMes)Me

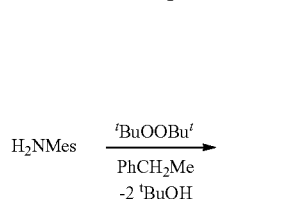

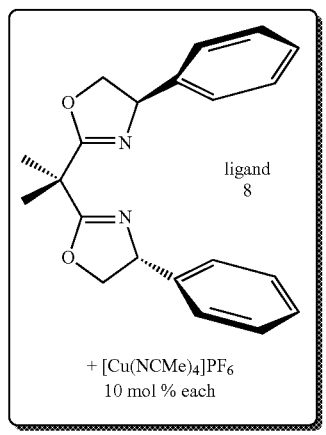

To a solution of 31 μL (30 mg; 0.222 mmol) of mesitylamine, 41 μL (32 mg; 0.222 mmol) t-butyl peroxide, 5 mL (neat) ethylbenzene was added 991 μL of a 0.0224M (0.022 mmol) solution of (S,S)-2,2'-isopropylidenebis(4-phenyl-2-oxazoline) (ligand 8) and tetrakis(acetonitrile) copper(I) hexafluorophosphate. The reaction mixture was allowed sealed in a pressure vessel and allowed to react at 80° C. for 18 hours. 56% yield ($^1$H NMR yield with 1,2,4,5-tetrachlorobenzene as standard) $^1$H NMR (benzene-$d_6$, RT): δ 7.105 (m, 7, Ar—H), 4.159 (m, 1, $C_{Bz}$—H), 2.907 (br, 1, N—H), 2.142 (s, 3, p-CH$_3$), 2.040 (s, 6, o-CH$_3$), 1.341 (d, 3, CH$_3$); m/z=240 (CI mode, [M]+1).

A byproduct of the reaction is a diazine (MesN═NMes). $^1$H NMR (benzene-$d_6$): δ 6.742 (s, 4, Ar—H), 2.461 (s, 12, o-CH$_3$), 2.116 (s, 6, p-CH$_3$); m/z=267 (CI mode, [M]+1).

Example 8

Preparation of PhCH(NHAr$^F$)Me (Ar$^F$=3,5-(CF$_3$)$_2$C$_6$H$_3$)

To a solution of 35 μL (51 mg; 0.222 mmol) of 3,5-bis(trifluoromethyl)aniline, 41 μL (32 mg; 0.222 mmol) t-butyl peroxide, 5 mL (neat) ethylbenzene was added 991 μL of a 0.0224M (0.022 mmol) solution of (S,S)-2,2'-isopropylidenebis(4-phenyl-2-oxazoline) (ligand 8) and tetrakis(acetonitrile)copper(I) hexafluorophosphate. The reaction mixture was allowed sealed in a pressure vessel and allowed to react at 80° C. for 40 hours. 50% yield ($^1$H NMR yield with 1,2,4,5-tetrachlorobenzene as standard) $^1$H (benzene-$d_6$, RT): δ 7.038 (m, 8, Ar—H), 3.883 (qnt, 1, $C_{Bz}$—H), 3.597 (br, 1, N—H), 1.029 (d, 3, CH$_3$); m/z=334 (CI mode, [M]+1).

Example 9

Preparation of PhCH(NHAr$^F$)Me (Ar$^F$=3,5-(CF$_3$)$_2$C$_6$H$_3$)

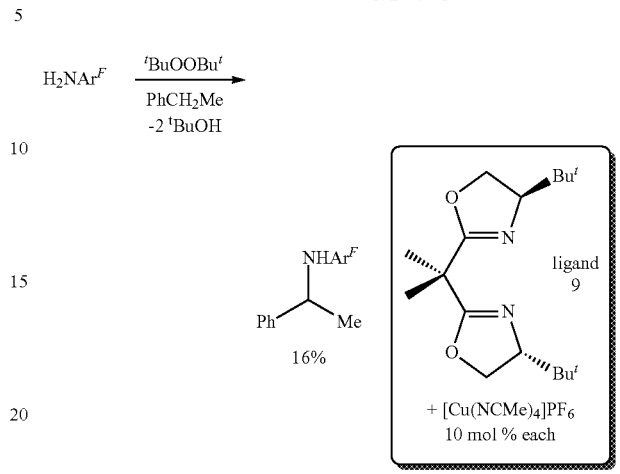

To a solution of 35 μL (51 mg; 0.222 mmol) of 3,5-bis(trifluoromethyl)aniline, 41 μL (32 mg; 0.222 mmol) t-butyl peroxide, 5 mL (neat) ethylbenzene was added 977 μL of a 0.0227M (0.022 mmol) solution of (S,S)-2,2'-Isopropylidene-bis(4-tert-butyl-2-oxazoline) (ligand 9) and tetrakis(acetonitrile)copper(I) hexafluorophosphate. The reaction mixture was allowed sealed in a pressure vessel and allowed to react at 80° C. for 40 hours. 16% yield ($^1$H NMR yield with 1,2,4,5-tetrachlorobenzene as standard) $^1$H (benzene-$d_6$; RT): δ 7.038 (m, 8, Ar—H), 3.883 (qnt, 1, $C_{Bz}$—H), 3.597 (br, 1, N—H), 1.029 (d, 3, CH$_3$); m/z=334 (CI mode, [M]+1).

Example 10

Catalytic C—H Bond Aminations using [IndBox]Cu Catalyst

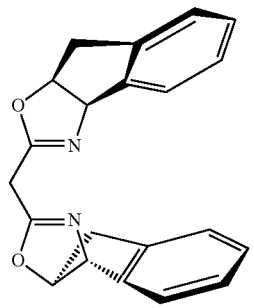

Figure 20:
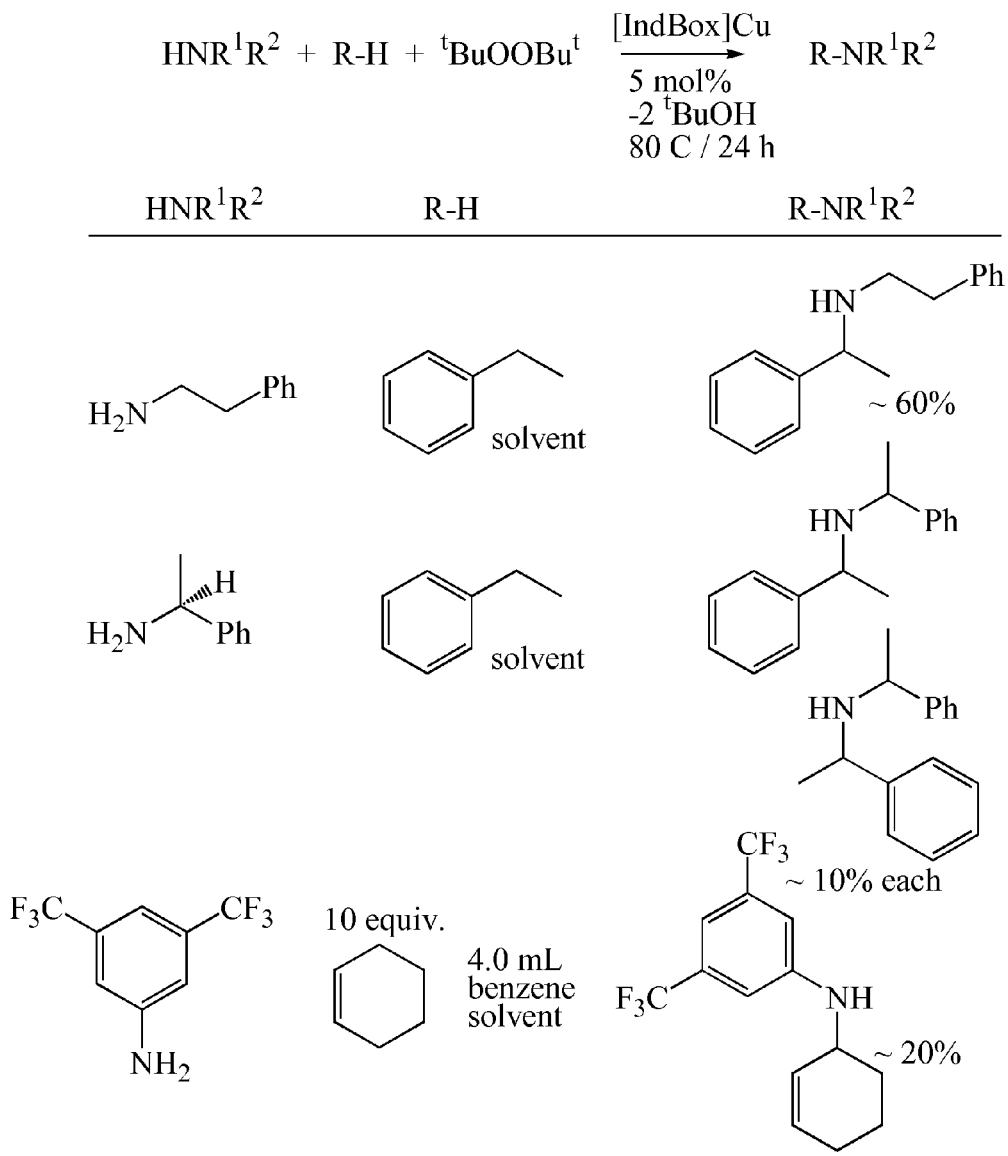
FIGS. 20 and 21 depict selected results of aminations using the [IndBox]Cu catalyst, at 5.0 mol % and 0.9 mol %, respectively.
Figure 21:
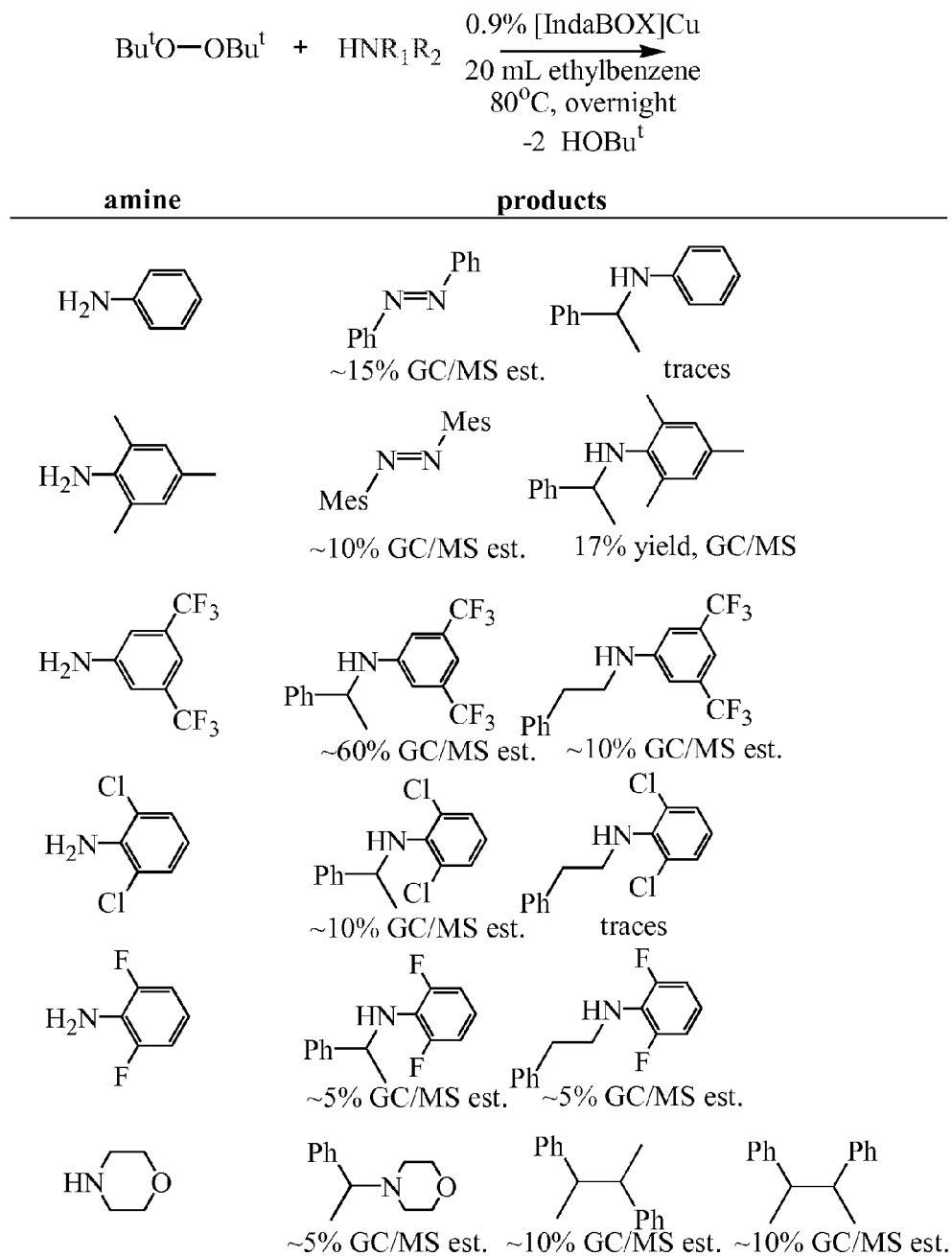

The IndBox catalyst ([3aR-[2(3'aR*,8'aS*),3'aβ,8'aβ]]-(+)-2,2'-methylenebis[3a,8a-dihydro-8H-indeno[1,2]oxazole]) was used to aminated ethylbenzene. Following the standard protocols described above, a 5 mol % or 0.9 mol % solution of the above catalyst was generated by addition of 5 mol % or 0.9 mol % IndBox and 5 mol % or 0.89 mol % CuOBu$^t$ to a solution of ethylbenzene (20 mL). Then approx. 1 mmol amine HNR$^1$R$^2$ and $^t$BuOOBu$^t$ were added in a 1:1 ratio. The solution was heated at 80° C. in a sealed tube for 24 hr and the products analyzed by GC/MS. Results are depicted in FIGS. 20 and 21).

Example 11

Preparation of PhCH(CH$_3$)NHMes

Figure 22:
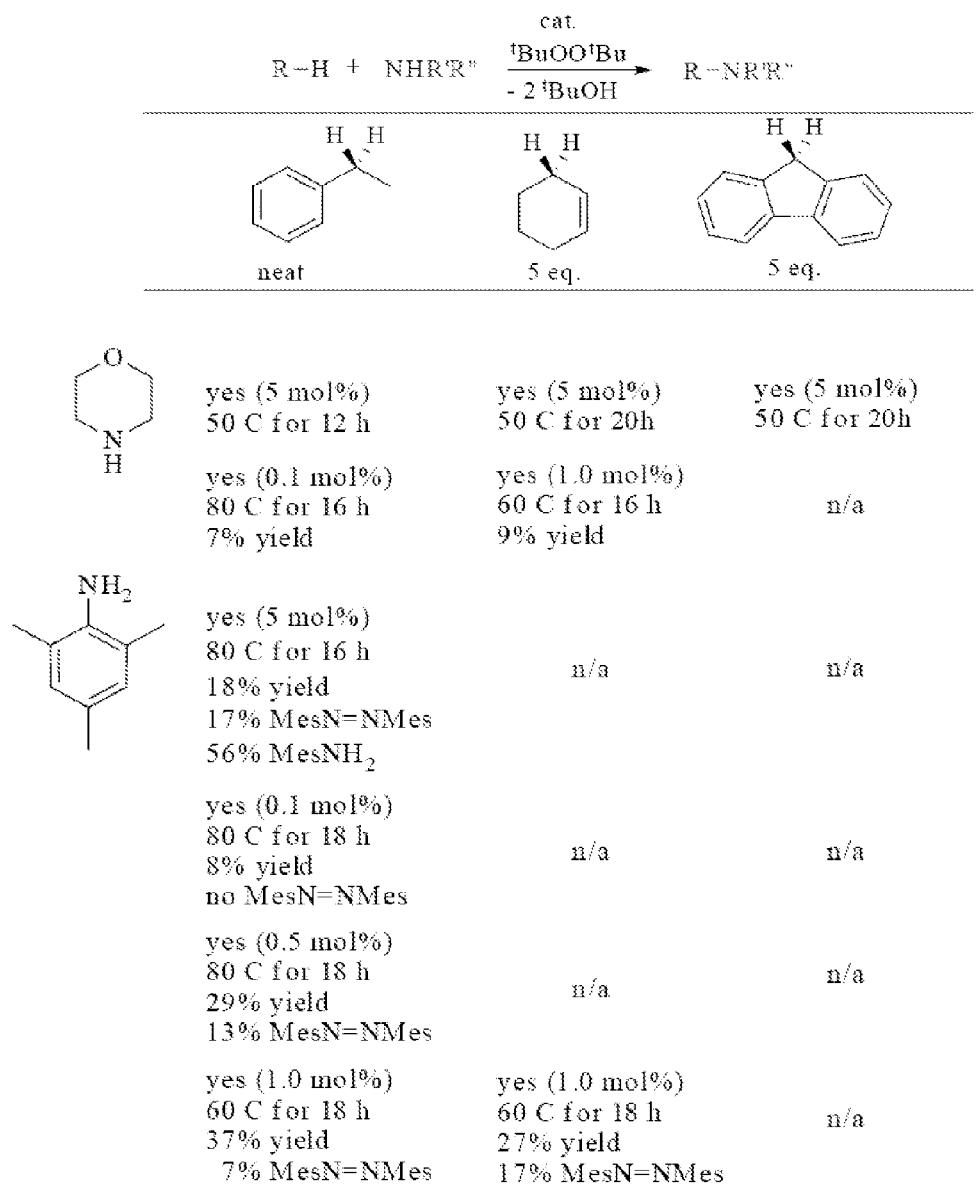
FIGS. 22 and 23 depict selected results of aminations using the [Cl$_2$NN$_{F6}$]Cu catalyst. Some of the aminations with ethylbenzene are described in detail in Examples 11 and 12. For the reactions of cyclohexene and fluorene, which were used in a small excess relative to the amine substrate (ca. 1 mmol), benzene (ca. 4 mL) was used as a solvent.
Figure 23:
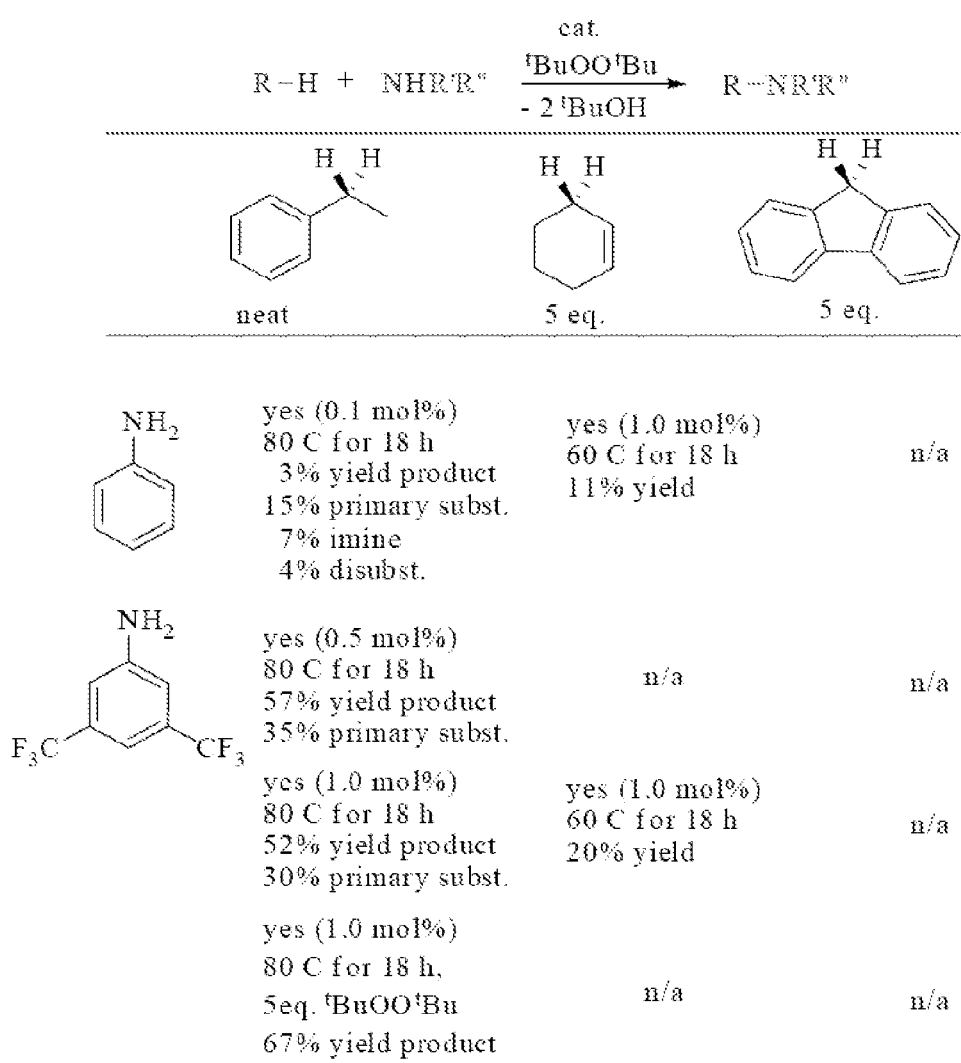

To a solution of 104 μL, (100 mg; 0.741 mmol) of mesitylamine, 136 μL, (108 mg; 0.741 mmol) t-butyl peroxide, 20 mL (neat) ethylbenzene was added the appropriate amount of {[Cl$_2$NN$_{F6}$Cu]}$_2$(C$_6$H$_6$) from a stock solution in benzene. The reaction mixture was allowed to react inside a sealed pressure vessel and allowed to react at the specified temperature and time. Yields were determined via $^1$H NMR using 1,2,4,5-tetrachlorobenzene as a standard. See FIGS. 22 and 23. $^1$H NMR (benzene-d$_6$, RT): δ 7.105 (m, 7, Ar—H), 4.159 (m, 1, C$_{Bz}$—H), 2.907 (br, 1, N—H), 2.142 (s, 3, p-CH$_3$), 2.040 (s, 6, o-CH$_3$), 1.341 (d, 3, CH$_3$); m/z=240 (CI mode); byproduct diazene MesN=NMes $^1$H NMR (benzene-d$_6$): δ 6.742 (s, 4, Ar—H), 2.461 (s, 12, o-CH$_3$), 2.116 (s, 6, p-CH$_3$); m/z=267 (CI mode).

Example 12

Preparation of PhCH(CH$_3$)NHAr$^F$ (Ar$^F$=3,5-(CF$_3$)$_2$C$_6$H$_3$)

To a solution of 115 μL, (170 mg; 0.741 mmol) of 3,5-bis(trifluoromethyl)aniline, 136 μL, (108 mg; 0.741 mmol) t-butyl peroxide, 20 mL (neat) ethylbenzene the appropriate amount of {[Cl$_2$NN$_{F6}$Cu]}$_2$(C$_6$H$_6$) from a stock solution in benzene. The reaction mixture was allowed to react inside a sealed pressure vessel and allowed to react at the specified temperature and time. Yields were determined via $^1$H NMR using 1,2,4,5-tetrachlorobenzene as a standard. See FIGS. 22 and 23. $^1$H (benzene-d$_6$, RT): δ 7.038 (m, 8, Ar—H), 3.883 (qnt, 1, C$_{Bz}$—H), 3.597 (br, 1, N—H), 1.029 (d, 3, CH$_3$); m/z=334 (CI mode).

Example 13

Catalytic C—H Amidation with [Cl$_2$NN]Cu and [Cl$_2$NN$_{F6}$]Cu Catalysts

Figure 24:
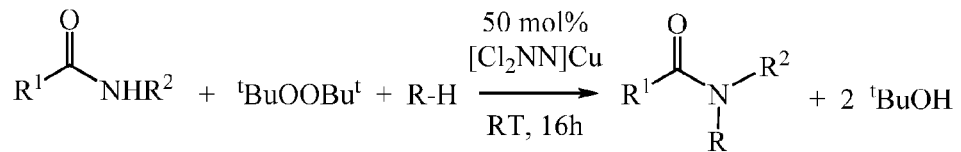
FIG. 24 depicts selected results of amidations with [Cl$_2$NN]Cu as the catalyst.

Both the [Cl$_2$NN]Cu and [Cl$_2$NN$_{F6}$]Cu catalysts were employed in amidation catalysis using organic amides as substrates (see FIGS. 24 and 25). High catalyst loadings (e.g., >10%) were required for the [Cl$_2$NN]Cu catalyst system because the organic amide can displace the β-diketiminate ligand from the copper center in the following acid/base reaction. The loss of [Cl$_2$NN]Cu and formation of H[Cl$_2$NN] has been verified by $^1$H NMR analysis in benzene-d$_6$ employing the organic amides benzamide (R=Ph, R$^1$=H), pyrrolidinone, and pivalamide (R=$^t$Bu, R$^1$=H).

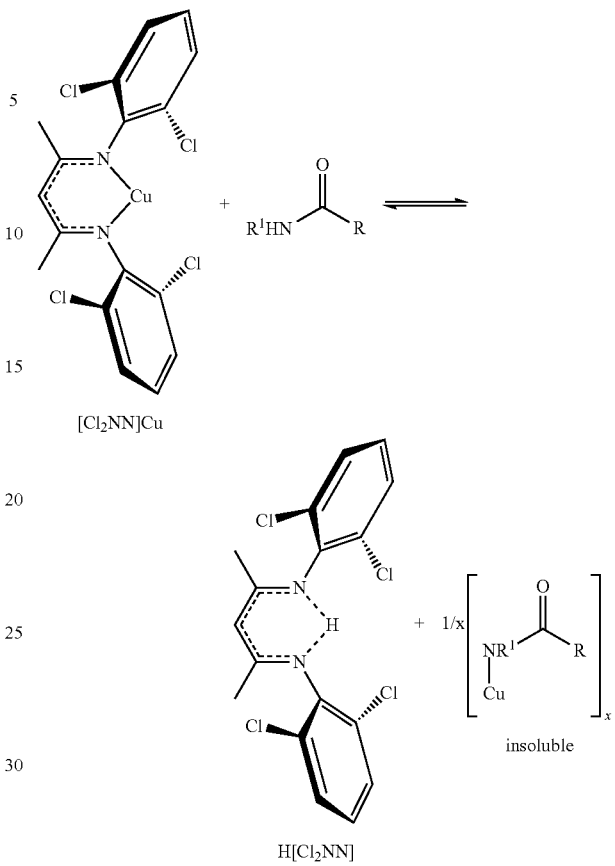

This displacement reaction does not take place when the [Cl$_2$NN$_{F6}$]Cu catalyst is used. The electron-withdrawing CF$_3$ groups on the backbone of the β-diketiminate make the [Cl$_2$NN$_{F6}$] ligand less basic and therefore less susceptible to displacement via acid/base chemistry.

The reactions described in FIGS. 24 and 25 typically employed 1 mmol organic amide with 1 equiv. $^t$BuOOBu$^t$ in neat R—H substrate (ca. 20 mL) using the specified catalyst, catalyst loading, temperature and time. In the case of 3,4-dihydro-2H-pyran, 1 equiv. of the dihydropyran was used without any additional solvent. Yields are estimated based on GC/MS and/or NMR analysis.

Example 14

Synthesis and Reactions of the [IndBox]Cu Catalyst

It has been found that the [IndBox]Cu catalyst may be conveniently prepared in situ from 1 equiv. IndBox bis(oxazoline) ligand and CuOBu$^t$. It appears that this catalyst performs similarly to the [Cl$_2$NN]Cu catalyst discussed above. For instance, clean amination of ethylbenzene and cyclohexene with H$_2$NAr$^F$ takes place. Complete conversion of H$_2$NAr$^F$ to the amination product occurs in ethylbenzene, though the reaction is a bit more sluggish employing 10 equiv. cyclohexene in benzene which goes to approximately 50% conversion after 16 h. This system also allows for low (20-50%) conversion of the primary alkylamines to the respective secondary amination products. Though low, we are encouraged by the 12% ee observed in the amination of ethylbenzene with [IndBox]Cu at 80° C.

Example 15

Synthesis and Characterization of the [Cl$_2$NN$_{F6}$]Cu Catalyst

The [Cl$_2$NN$_{F6}$]Cu catalyst can be prepared as outlined below (see FIG. 26A).

A. Preparation of 2,6-Cl$_2$C$_6$H$_3$N$_3$ ($^{C12}$ArN$_3$)

Following a literature procedure for the conversion of aromatic amines to azides (Barral, K.; Moorhouse, A. D.; Moses, J. E. *Org. Lett.* 2007, 9, 1809-1811), a solution of 2,6-dichloroaniline (6.41 g, 39.5 mmol) in 50 mL MeCN was cooled to 0° C. in an ice bath. Chilled (0° C.) tert-butylnitrite (6.10 g, 59.2 mmol) was added followed by chilled trimethylsilylazide (5.45 g, 47.4 mmol). The reaction mixture was allowed to stir for 3 hours at room temperature. The volatiles were removed in vacuo maintaining a temperature below 35° C. The resulting crude oil was purified via column chromatography using pentane and collecting the first yellow fraction to provide 67% yield (4.99 g; 26.5 mmol). $^1$H NMR (benzene-d$_6$): δ 6.689 (d, 2, m-Ar—H), 6.189 (t, 1, p-Ar—H); m/z (CI mode)=161 (M$^+$—N$_2$).

B. Preparation of $^{C12}$ArN═PMe$_3$

Under a nitrogen atmosphere a chilled (−35° C.) solution of 2,6-dichlorophenylazide ($^{C12}$ArN$_3$) (4.99 g, 26.5 mmol) in 10 mL of THF was added slowly to a chilled (−35° C.) solution trimethylphosphine (26.5 mL of a 1.0 M solution in THF, 26.5 mmol). Rapid gas evolution was observed. The yellow solution was allowed to stand for 20 minutes at room temperature. All volatiles were removed from the crude product in vacuo. The product was used as is for the following steps. $^1$H NMR (benzene-d$_6$): δ 7.264 (d, 2, m-Ar—H), 6.333 (t, 1, p-Ar—H), 1.000 (s, 9, Me); m/z (CI mode)=237 (M$^+$).

C. Thermal Synthesis of H[Cl$_2$NN$_{F6}$]

An aza-Wittig reaction similar to that reported by Sadighi (Laitar, D. S.; Mathison, C. J. N.; Davis, W. M.; Sadighi, J. P. *Inorg. Chem* 2003, 42, 7354-7356) was used to prepare the new fluorinated β-diketiminate ligand H[Cl$_2$NN$_{F6}$]. Under a nitrogen atmosphere, $^{C12}$ArN═PMe$_3$ (0.458 g, 1.94 mmol) in 3 mL toluene and 1,1,1,5,5,5-hexafluoropentadione (0.201 g, 0.966 mmol) in 3 mL of toluene were added together inside a glass pressure vessel. The pressure vessel was sealed and heated for 108 hours at 100° C. The brown reaction was concentrated to remove all volatiles. The brown remaining oil was purified via column chromatography using 30:1 hexane:toluene as the mobile phase. The first bright yellow fraction was collected. Crystallization from methanol at −20° C. afforded bright yellow crystals in 56% yield (269 mg; 0.543 mmol). $^1$H NMR (benzene-d$_6$): δ 11.50 (s, 1H, N—H) δ 6.83 (d, 4H, meta-Ar—H), δ 6.30 (t, 2H, para-Ar—H), δ 6.10 (s, 1, backbone-C—H); $^{13}$C NMR (benzene-d$_6$): δ 153.07, 152.76, 138.62, 131.18, 128.50, 127.98, 121.04, 118.19, 89.82; $^{19}$F NMR (C$_6$F$_6$ in C$_6$D$_6$): −69.7; m/z (CI mode)=497 (M$^+$).

D. Microwave Synthesis of H[Cl$_2$NN$_{F6}$]

Under a nitrogen atmosphere, $^{C12}$ArN═PMe$_3$ (0.620 g, 2.63 mmol) and 1,1,1,5,5,5-hexafluoropentadione (0.273 g, 1.31 mmol) were added together in 4 mL toluene were inside a microwave pressure vessel. The microwave vessel was sealed. The microwave heated the reaction mixture for 5 hours at 150° C., 100 Watts, and 275 psi. All volatiles were removed from the crude product in vacuo. The crude product was purified via column chromatography using silica and hexanes:toluene (30:1) and a bright yellow oil was collected as the first compound off the column. Crystallization from pentane at −35° C. afforded bright yellow crystals in 42% yield (273 mg; 0.551 mmol). Characterization identical to the thermal synthesis of H[Cl$_2$NN$_{F6}$].

E. Preparation of [Cl$_2$NN$_{F6}$]Cu

Under a nitrogen atmosphere, H[Cl$_2$NN$_{F6}$] (2.38 g, 4.79 mmol) was added to a stirring solution of copper(I) tert-butoxide (0.786 g, 5.75 mmol) in benzene (6 mL) and pentane (10 mL). The reaction mixture was allowed to stir for 3 hours at room temperature. All volatiles were removed under vacuo and the remaining solid was washed with cold pentane to afford an orange solid in 75% yield (2.15 g; 1.79 mmol). $^1$H NMR (benzene-d$_6$): δ 6.993 (d, 4H, meta-Ar—H), δ 6.401 (t, 2H, para-Ar—H), δ 6.095 (s, 1.00, backbone-C—H); $^{19}$F NMR (C$_6$F$_6$ in C$_6$D$_6$): −67.5.

F. Preparation of [Cl$_2$NN$_{F6}$]CuOBu$^t$

Under a nitrogen atmosphere, a chilled (−35° C.) solution tert-butylperoxide (0.141 g, 0.967 mmol) in 2 mL benzene was added to a chilled solution of [Cl$_2$NN$_{F6}$]Cu (taken as {[Cl$_2$NN$_{F6}$]Cu}$_2$(benzene): 0.135 g, 0.113 mmol) in 3 mL pentane. The reaction mixture was allowed to stir at room temperature for 90 minutes and changed color from orange/yellow to purple/maroon. All volatiles were removed under vacuo and the remaining solid was taken up in 20 mL of pentane and filtered through Celite and concentrated for crystallization at −35° C. to afford red crystals in 34% yield (0.050 g, 0.0791 mmol). The product was characterized by single-crystal X-ray diffraction.

Example 16

Preparation of {[Cl$_2$NN]Cu}$_2$(benzene)$_{0.8}$

A solution of KO$^t$Bu (3.53 g, 31.6 mmol, ca. 20 mL THF) was added to a slurry of CuI (5.99 g, 31.6 mmol, in ca. 80 mL THF) and stirred overnight. The solution started milky white and developed a slight gray tint over time. The reaction was filtered over Celite. To the filtrate was added benzene (28 mL, 316 mmol) and a solution of H[Cl$_2$NN] (12.25 g, 31.57 mmol, in ca. 25 mL THF). The mixture was stirred for 3 hours and stripped to ¼ of its volume (30-50 mL) and the precipitate was collected on a frit and rinsed with 3×40 mL of pentane to give 11.50 g (80% yield) of a pale yellow powder, 98% pure by $^1$H NMR. $^1$H NMR (benzene-d$_6$): δ 7.10 (d, 3.48, meta-Ar—H), δ 6.98 (t, 1.97, para-Ar—H), δ 4.83 (s, 1.00, backbone-C—H), and δ 1.71 (s, 5.32, CH$_3$). $^1$H NMR (acetonitrile-d$_3$): δ 7.37 (overlap, 5.57, meta-Ar—H and 0.4 eq. benzene), δ 6.98 (t, 1.98, para-Ar—H), δ 4.81 (s, 1.00, backbone-C—H), and δ 1.69 (s, 5.56, CH$_3$). Calculated elemental analysis: C, 48.30; H, 3.21; N, 5.28; experimental elemental analysis (average of three runs): C, 48.29; H, 3.07; N, 5.66.

If significant excess ligand is found, purification can be obtained by calculating the amount of free ligand in the sample and adding the exact amount of Cu—OBu$^t$ to the sample with about the same amount of THF and benzene as used above. Isolation of the product is the same as above.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A method of amination or amidation, comprising the step of:

combining a substrate, comprising a reactive C—H bond, and an amine or amide, comprising a reactive N—H bond, in the presence of an oxidizing agent and a metal-containing catalyst, wherein the oxidizing agent is a peroxide represented by:

$R^6$—O—O—$R^6$ wherein $R^6$ is independently for each occurrence hydrogen, alkyl, alkenyl, alkynyl, aryl, heteroaryl, aralkyl or heteroaralkyl, and the metal-containing catalyst is a transition metal-containing catalyst, thereby forming a product with a covalent bond between the carbon of the reactive C—H bond and the nitrogen of the reactive N—H bond;

the substrate is represented by:

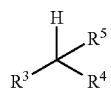

wherein the reactive C—H bond is H—$C(R^3)(R^4)(R^5)$;

$R^3$ is alkenyl, alkynyl, aryl, heteroaryl, aralkyl, heteroaralkyl, carbocyclyl, heterocyclyl, polycyclyl, carbonyl, ester or ether;

$R^4$ is hydrogen, alkyl, alkenyl, alkynyl, aryl, heteroaryl, aralkyl, heteroaralkyl, carbocyclyl, heterocyclyl, polycyclyl, carbonyl, ester or ether;

$R^5$ is hydrogen, alkyl, alkenyl, alkynyl, aryl, heteroaryl, aralkyl, heteroaralkyl, carbocyclyl, heterocyclyl, polycyclyl, carbonyl, ester or ether; and the substrate is optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano; or the substrate is a cyclopropane, cyclobutane, cyclopentane, cyclohexane, indane, 2-oxoindane, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactone, lactam, azetidinone, pyrrolidinone, sultam, or sultone; and the substrate is optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano;

the amine or amide is represented by:

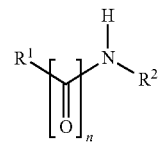

wherein $R^1$ is hydrogen, alkyl, alkenyl, alkynyl, aryl, heteroaryl, aralkyl or heteroaralkyl;

$R^2$ is hydrogen, alkyl, alkenyl, alkynyl, aryl, heteroaryl, aralkyl or heteroaralkyl; or $R^1$ and $R^2$ taken together with the atoms to which they are bound, form a five, six or seven membered ring which contains 0-2 heteroatoms and is optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano;

n is 0 or 1;

the metal-containing catalyst is selected from the group consisting of Formula I and its enantiomer, Formula IIa and its enantiomer, Formula IIb and its enantiomer, Formula III and its enantiomer, and Formula IV and its enantiomer;

Formula I is represented by:

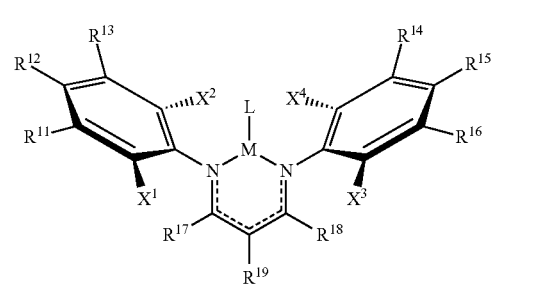

wherein $R^{11}$ to $R^{19}$ are independently selected from the group consisting of hydrogen, alkyl, aryl, aralkyl, halogen, cyano, nitro and trifluoromethyl;

$X^1$ to $X^4$ are independently selected from the group consisting of hydrogen, halogen and perhaloalkyl;

L is absent or a Lewis base;

M is copper;

Formula IIa is represented by:

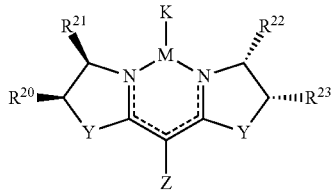

IIa wherein
R$^{20}$ is hydrogen, alkyl, aryl or heteroaryl;
R$^{21}$ is alkyl, aryl or heteroaryl;
R$^{22}$ is hydrogen, alkyl, aryl or heteroaryl;
R$^{23}$ is alkyl, aryl or heteroaryl;
Y is O, S, CH$_2$ or CH$_2$CH$_2$;
Z is hydrogen or cyano;
L is absent or a Lewis base;
M is copper;
Formula IIb is represented by:

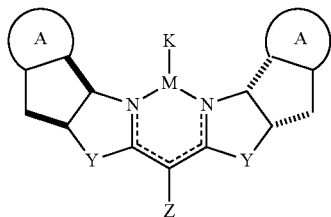

IIb wherein
A is aryl or heteroaryl;
Y is O, S, CH$_2$ or CH$_2$CH$_2$;
Z is hydrogen or cyano;
L is absent or a Lewis base;
M is copper;
Formula III is represented by:

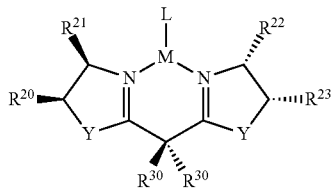

III wherein
R$^{20}$ is hydrogen, alkyl, aryl or heteroaryl;
R$^{21}$ is alkyl, aryl or heteroaryl;
R$^{22}$ is hydrogen, alkyl, aryl or heteroaryl;
R$^{23}$ is alkyl, aryl or heteroaryl;
R$^{30}$ is alkyl or both R$^{30}$ taken together are cycloalkyl;
Y is O, S, CH$_2$ or CH$_2$CH$_2$;
L is a Lewis base;
M is copper;
Formula IV is represented by:

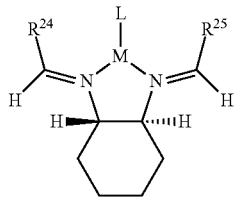

IV wherein
R$^{24}$ is aryl or heteroaryl;
R$^{25}$ is aryl or heteroaryl;

L is a Lewis base; and
M is copper.

2. The method of claim 1, wherein the substrate comprising a reactive C—H bond is represented by:

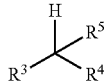

wherein
the reactive C—H bond is H—C(R$^3$)(R$^4$)(R$^5$);
R$^3$ is alkyl, alkenyl, alkynyl, aryl, heteroaryl, aralkyl, heteroaralkyl, carbocyclyl, heterocyclyl, polycyclyl, carbonyl, ester or ether;
R$^4$ is hydrogen, alkyl, alkenyl, alkynyl, aryl, heteroaryl, aralkyl, heteroaralkyl, carbocyclyl, heterocyclyl, polycyclyl, carbonyl, ester or ether;
R$^5$ is hydrogen, alkyl, alkenyl, alkynyl, aryl, heteroaryl, aralkyl, heteroaralkyl, carbocyclyl, heterocyclyl, polycyclyl, carbonyl, ester or ether; and
the substrate is optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

3. The method of claim 1, wherein the substrate is a cyclopropane, cyclobutane, cyclopentane, cyclohexane, indane, 2-oxoindane, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactone, lactam, azetidinone, pyrrolidinone, sultam, or sultone; and the substrate is optionally substituted with 1-3 substituents selected from the group consisting of halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano.

4. The method of claim 1, wherein the amine or amide is selected from the group consisting of

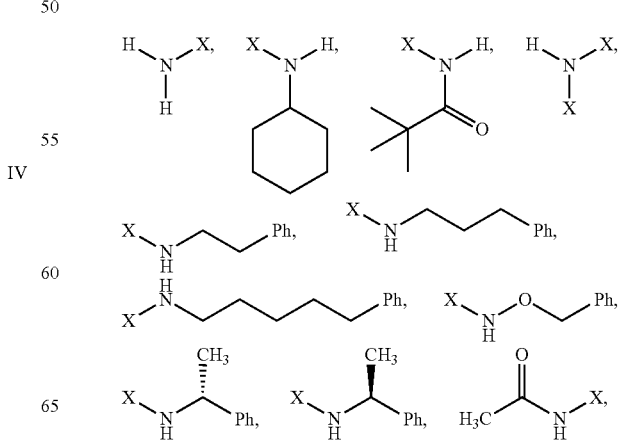

-continued

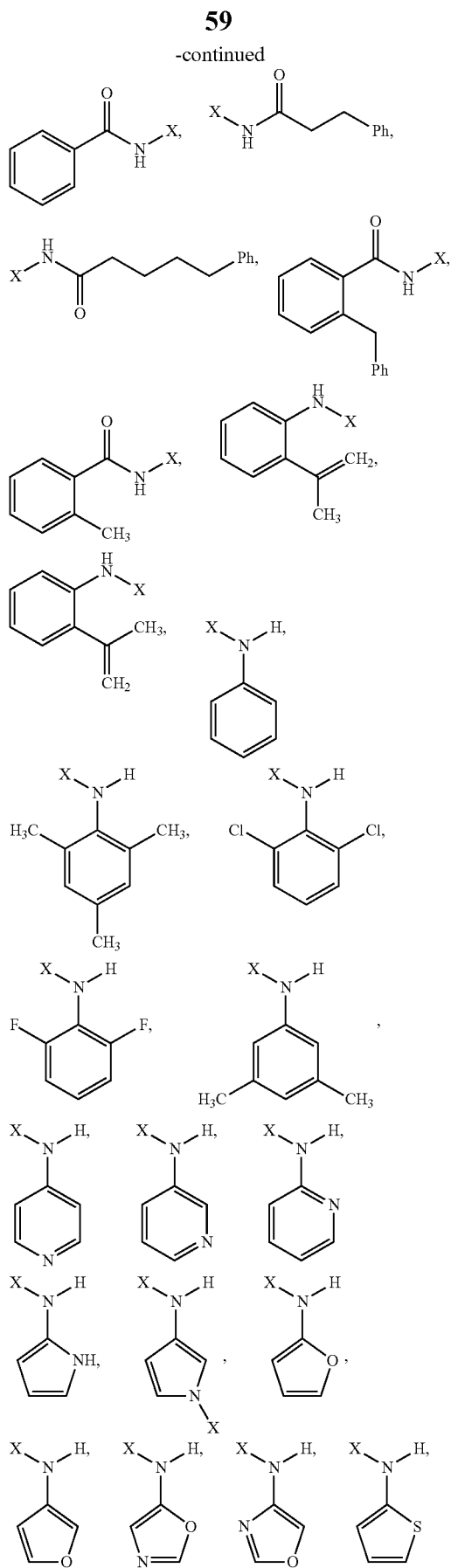

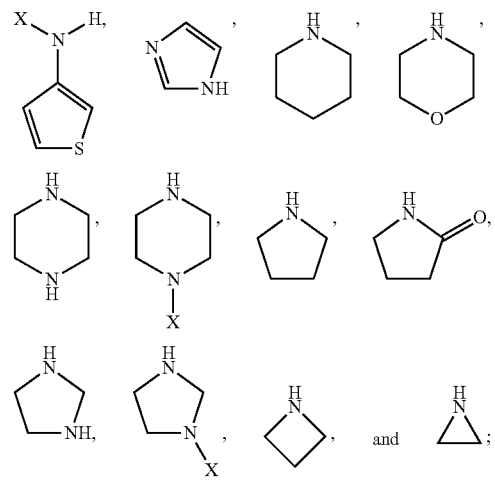

and X is hydrogen, alkyl, fluoroalkyl, aryl, aralkyl, heteroaryl, heteroaralkyl, silyl, carbonyl, ester, thioester, sulfonyl, sulfonate, or amide.

5. The method of claim 1, wherein $R^6$ is alkyl.

6. The method of claim 1, wherein the transition metal is Cu(I) or Cu(II).

7. The method of claim 1, wherein the metal-containing catalyst is represented by Formula I or its enantiomer.

8. The method of claim 7, wherein the catalyst is selected from the group consisting of

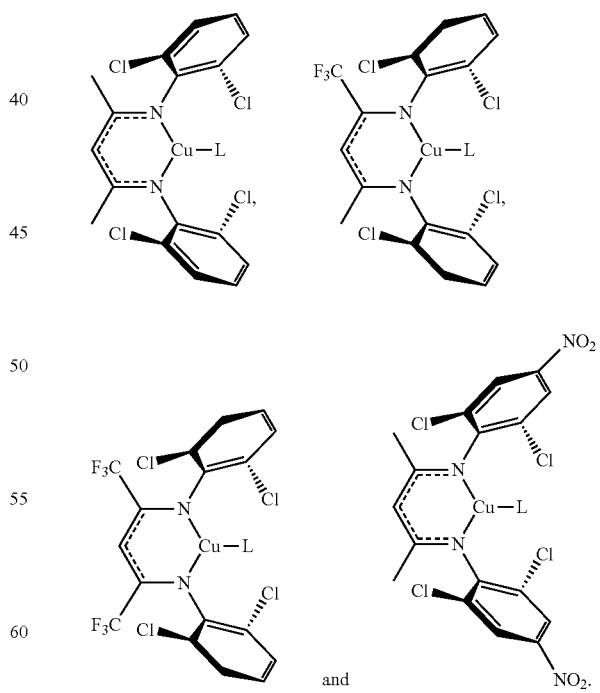

9. The method of claim 1, wherein the metal-containing catalyst is represented by Formula IIa or its enantiomer.

10. The method of claim 9, wherein the catalyst is selected from the group consisting of

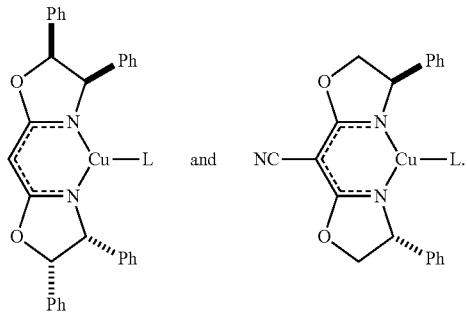

11. The method of claim 1, wherein the metal-containing catalyst is represented by Formula IIb or its enantiomer.

12. The method of claim 11, wherein the metal-containing catalyst is

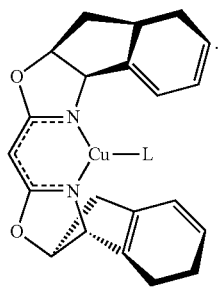

13. The method of claim 1, wherein the metal-containing catalyst is represented by Formula III or its enantiomer.

14. The method of claim 13, wherein the catalyst is selected from the group consisting of

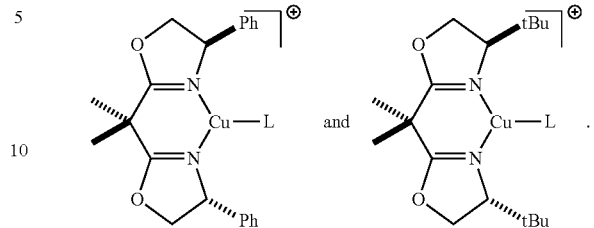

15. The method of claim 1, wherein the metal-containing catalyst is represented by Formula IV or its enantiomer.

16. The method of claim 15, wherein the catalyst is

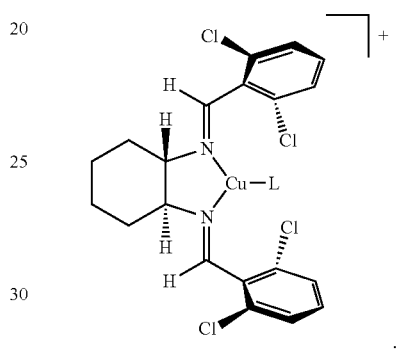

17. The method of claim 1, wherein the reaction is run in neat substrate.

18. The method of claim 1, wherein the reaction is run at a temperature from about 50° C. to about 100° C.

* * * * *

UNITED STATES PATENT AND TRADEMARK OFFICE
CERTIFICATE OF CORRECTION

PATENT NO. : 8,895,781 B2  
APPLICATION NO. : 13/061021  
DATED : November 25, 2014  
INVENTOR(S) : Warren Page 1 of 1

It is certified that error appears in the above-identified patent and that said Letters Patent is hereby corrected as shown below:

In the Claims:

Column 57, claim 1, line 3 - 10, replace

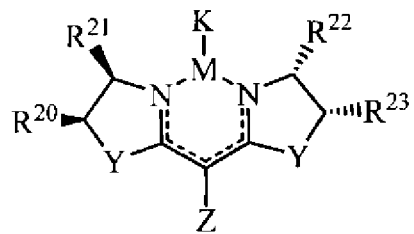  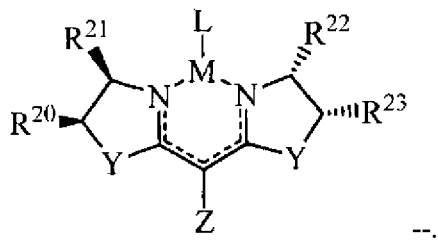

with --   --.

Column 57, claim 1, line 21 - 29, replace

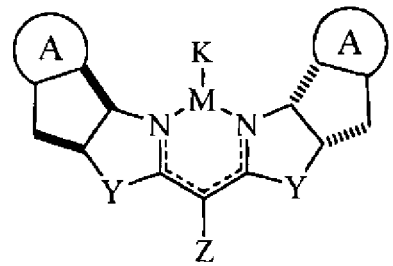  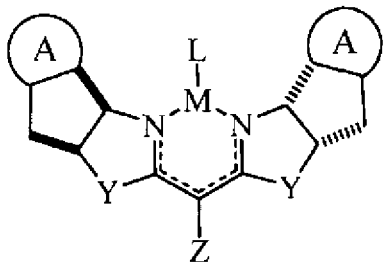

with --   --.

Signed and Sealed this  
Twenty-fourth Day of March, 2015

Michelle K. Lee  
*Director of the United States Patent and Trademark Office*